US012655484B2

(12) United States Patent
Cheishvili et al.

(10) Patent No.: US 12,655,484 B2
(45) Date of Patent: Jun. 16, 2026

(54) DNA METHYLATION MARKERS FOR NONINVASIVE DETECTION OF CANCER AND USES THEREOF

(71) Applicant: HKG EPITHERAPEUTICS LIMITED, Pierrefonds (CA)

(72) Inventors: David Cheishvili, Pierrefonds (CA); Hui Li, Hong Kong (CN); Chi Fat Wong, Hong Kong (CN)

(73) Assignee: EpiMedTechGlobal (EMTG), Singapore (SG)

( * ) Notice: Subject to any disclaimer, the term of this patent is extended or adjusted under 35 U.S.C. 154(b) by 1293 days.

(21) Appl. No.: 17/253,406

(22) PCT Filed: Jul. 9, 2019

(86) PCT No.: PCT/IB2019/055855
§ 371 (c)(1),
(2) Date: Dec. 17, 2020

(87) PCT Pub. No.: WO2020/012367
PCT Pub. Date: Jan. 16, 2020

(65) Prior Publication Data
US 2021/0171617 A1     Jun. 10, 2021

Related U.S. Application Data

(60) Provisional application No. 62/695,429, filed on Jul. 9, 2018.

(51) Int. Cl.
*C12Q 1/6886* (2018.01)
*G16B 30/00* (2019.01)

(52) U.S. Cl.
CPC ........... *C12Q 1/6886* (2013.01); *G16B 30/00* (2019.02); *C12Q 2600/154* (2013.01)

(58) Field of Classification Search
None
See application file for complete search history.

(56) References Cited

U.S. PATENT DOCUMENTS

2017/0175205 A1* 6/2017 Toung ................... G16B 40/00
2020/0263256 A1* 8/2020 Zhang .................. C12Q 1/6886

FOREIGN PATENT DOCUMENTS

CN      107541565      1/2018
CN      109680060      4/2019
(Continued)

OTHER PUBLICATIONS

Li, X., Liu, Y., Salz, T., Hansen, K. D., & Feinberg, A. (2016). Whole-genome analysis of the methylome and hydroxymethylome in normal and malignant lung and liver. Genome research, 26(12), 1730-1741. (Year: 2016).*
(Continued)

*Primary Examiner* — Kaitlyn L Minchella
*Assistant Examiner* — Noah A. Auger
(74) *Attorney, Agent, or Firm* — DECODE LEGAL

(57) ABSTRACT

A "binary-categorical differentiation (BCD)" method for finding a combination of a small number (2-10) of exquisite DNA methylation positions in the human genome (CG IDs) for detecting cancer in DNA in biological material derived from a patient such as plasma, saliva, urine, feces, tissue biopsy, tissue swabs and tissue smears (such as pap smears) and distinguish it from other tissue cell free DNA and blood cells DNA. Another method for detecting tissue of origin of tumor DNA uses a combination of small number of unique DNA methylation positions in the human genome (CG IDs). Various novel combinations of CG IDs derived from tumor DNA for detecting with high specificity and sensitivity a. hepatocellular carcinoma (HCC), b. lung cancer, c. prostate cancer, d. breast cancer, e. colorectal cancer, f. pancreatic cancer, g. brain cancer (glioblastoma), h. gastric cancer i.
(Continued)

Normal tissues          Adjacent liver          HCC ovarian cancer, j. cervical cancer k. head and neck squamous cell carcinoma (HNSC), l. esophageal cancer m. bladder cancer, n. renal cancer, o. testicular cancer, p. common solid tumors, q. blood cancers, r. acute myeloid leukemia (AML), s. melanoma by measuring the DNA methylation of a combination of specific CG IDs and deriving a "methylation score". Kits for predicting cancer using CG IDs using multiplexed next generation sequencing methylation assays, pyrosequencing assays and methylation specific PCR from a small volume of plasma. Various methods using plasma, urine, feces, tissue biopsy or tissue swabs help lead to prediction of cancer in persons with no other clinical evidence for cancer.

6 Claims, 55 Drawing Sheets

Specification includes a Sequence Listing.

(56) References Cited

FOREIGN PATENT DOCUMENTS

| EP | 3239302 | A1 | 11/2017 | | |
|----|---------|----|---------|----|----|
| JP | 2008245635 | A | 10/2008 | | |
| JP | 2015514150 | | 5/2015 | | |
| JP | 2017060474 | A | 3/2017 | | |
| JP | 2021-532735 | | 12/2021 | | |
| WO | 1997045560 | A1 | 12/1997 | | |
| WO | 2017048932 | | 3/2017 | | |
| WO | WO-2017048932 | A1 * | 3/2017 | .......... | C12Q 1/6886 |
| WO | 2017129716 | A1 | 8/2017 | | |
| WO | 2017143296 | | 8/2017 | | |
| WO | 2017201606 | | 11/2017 | | |
| WO | 2017201606 | A1 | 11/2017 | | |
| WO | 2018005668 | | 1/2018 | | |
| WO | 2018009696 | | 1/2018 | | |
| WO | 2018009702 | | 1/2018 | | |
| WO | 2018009703 | | 1/2018 | | |
| WO | 2018009709 | | 1/2018 | | |
| WO | WO-2018161031 | A1 * | 9/2018 | .......... | C12Q 1/6886 |

OTHER PUBLICATIONS

Lee, E. J., Luo, J., Wilson, J. M., & Shi, H. (2013). Analyzing the cancer methylome through targeted bisulfite sequencing. Cancer letters, 340(2), 171-178. (Year: 2013).*

Vrba, L., & Futscher, B. W. (2018). A suite of DNA methylation markers that can detect most common human cancers. Epigenetics, 13(1), 61-72. (Year: 2018).*

The Cancer Genome Atlas Research Network (2017). Comprehensive and integrative genomic characterization of hepatocellular carcinoma. Cell, 169(7), 1327-1341. (Year: 2017).*

Illumina. (2014). Infinium® HumanMethylation450 BeadChip. chrome-extension://efaidnbmnnnibpcajpcglclefindmkaj/https://www.illumina.com/documents/products/datasheets/datasheet_humanmethylation450.pdf (Year: 2014).*

Lam, K., Pan, K., Linnekamp, J. F., Medema, J. P., & Kandimalla, R. (2016). DNA methylation based biomarkers in colorectal cancer: a systematic review. Biochimica et Biophysica Acta (BBA)—Reviews on Cancer, 1866(1), 106-120. (Year: 2016).*

Kang, S., Li, Q., Chen, Q., Zhou, Y., Park, S., Lee, G., . . . & Zhou, X. J. (2017). CancerLocator: non-invasive cancer diagnosis and tissue-of-origin prediction using methylation profiles of cell-free DNA. Genome biology, 18, 1-12. (Year: 2017).*

"Infinium HumanMethylation450K V1.2 Product Files." Illumina. com, May 23, 2013, support.illumina.com/downloads/infinium_humanmethylation450_product_files.html. (Year: 2013).*

Li, Yang, International Search Report and Written Opinion, International PCT Patent Application PCT/IB2019/055855, Feb. 21, 2020.

Stefansson, O. A., Moran, S., Gomez, A., Sayols, S., Arribas-Jorba, C., Sandoval, J., . . . , Esteller, M. (2014), A DNA methylation-based definition of biologically distinct breast cancer subtypes. Mol Oncol. doi:10.1016/j.molonc.2014.10.012.

Aguirre-Ghiso, J. A. (2007). Models, mechanisms and clinical evidence for cancer dormancy, Nat Rev Cancer, (11), 834-846. doi:10.1038/nrc2256.

Xu, R. H., Wei, W., Krawczyk, M., Wang, W., Luo, H., Flagg, K., . . . , Zhang, K. (2017), Circulating tumour DNA methylation markers for diagnosis and prognosis of hepatocellular carcinoma. Nat Mater, 16(11), 1155-1161. doi:10.1038/nmat4997.

Ehrlich, M. (2002). DNA methylation in cancer: too much, but also too little. Oncogene, 21(35), 5400-5413.

Ramzy, II, Omran, D. A., Hamad, O., Shaker, O., & Abboud, A. (2011). Evaluation of serum LINE-1 hypomethylation as a prognostic marker for hepatocellular carcinoma. Arab J Gastroenterol, 12(3), 139-142. doi:10.1016/j.ajg.2011.07.002.

Feil R, Charlton J, Bird A P, Walter J, Reik W. Methylation analysis on individual chromosomes: improved protocol for pisulphite genomic sequencing. Nucleic Acids Res. Feb. 25, 1994;22(4):695-6.

Grigg G, Clark S. Sequencing 5-methylcytosine residues in genomic DNA, Bioessays, Jun. 1994; 16(6):431-6, 431.

Zhai, R., Zhao, Y., Su, L., Cassidy, L., Liu, G., & Christiani, D. C. (2012), Genome-wide DNA methylation profiling of cell-free serum DNA in esophageal adenocarcinoma and Barrett esophagus. Neoplasia, 14(1), 29-33.

El-Serag, H. B. (2011). Hepatocellular carcinoma. N Engl J Med, 365(12), 1118-1127, doi:10.1056/NEJMra1001683.

Baylin, S. B., Esteller, M., Rountree, M. R., Bachman, K. E., Schuebel, K., & Herman, J.G. (2001). Aberrant patterns of DNA methylation, chromatin formation and gene expression in cancer. Hum Mol Genet, 10(7), 687-692.

Issa, J. P., Vertino, P. M., Wu, J., Sazawal, S., Celano, P., Nelkin, B. D., . . . Baylin, S. B. (1993). Increased cytosine DNA-methyltransferase activity during colon cancer progression. J Natl Cancer Inst, 85(15), 1235-1240.

Valente, S., Liu, Y., Schnekenburger, M., Zwergel, C., Cosconati, S., Gros, C., . . . , Mai, A. (2014). Selective non-nucleoside inhibitors of human DNA methyltransferases active in cancer including in cancer stem cells. J Med Chem, 57(3), 701-713. doi:10.1021/jm4012627.

Warton, K., & Samimi, G. (2015), Methylation of cell-free circulating DNA in the diagnosis of cancer. Front Mol Biosci, 2, 13. doi:10.3389/fmolb.2015.00013.

Dominguez-Vigil, I. G., Moreno-Martinez, A. K., Wang, J. Y., Roehrl, M. H. A., & Barrera-Saldana, H. A. (2018). The dawn of the liquid biopsy in the fight against cancer. Oncotarget, 9(2), 2912-2922. doi:10.18632/oncotarget.23131.

Martin V, Ribieras S, Song-Wang X, Rio M C, Dante R. Genomic sequencing indicates a correlation between DNA hypomethylation in the 5' region of the pS2 gene and its expression in human breast cancer cell lines, Gene, 1995, May 19;157(1-2):261-4.

Radpour, R., Barekati, Z., Kohler, C., Lv, Q., Burki, N., Diesch, C., . . . , Zhong, X. Y. (2011). Hypermethylation of tumor suppressor genes involved in critical regulatory pathways for developing a blood-based test in breast cancer. PLoS One, 6(1), e16080. doi:10.1371/journal.pone.0016080.

Breitbach, S., Tug, S., Helmig, S., Zahn, D., Kubiak, T., Michal, M., . . . , Simon, P. (2014), Direct quantification of cell-free, circulating DNA from unpurified plasma. PLOS One, 9(3), e87838. doi:10.1371/journal.pone.0087838.

Tan, C. H., Low, S. C., & Thng, C. H. (2011), APASL and AASLD Consensus Guidelines on Imaging Diagnosis of Hepatocellular Carcinoma: A Review. Int J Hepatol, 2011, 519783. doi:10.4061/2011/519783.

Luczak, M. W., & Jagodzinski, P. P. (2006), The role of DNA methylation in cancer 25 development. Folia Histochem Cytobiol, 44(3), 143-154.

Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method, Hum Mol Genet. Mar. 1997; 6(3):387-95.

(56)　　　　　References Cited

OTHER PUBLICATIONS

Chan, K. C., Jiang, P., Chan, C. W., Sun, K., Wong, J., Hui, E. P., . . . Lo, Y. M. (2013), Noninvasive detection of cancer-associated genome-wide hypomethylation and copy number aberrations by plasma DNA bisulfite sequencing. Proc Natl Acad 10 Sci U S A, 110(47), 18761-18768. doi:10.1073/pnas.1313995110.

Flores, A., & Marrero, J. A. (2014). Emerging trends in hepatocellular carcinoma: focus on diagnosis and therapeutics. Clin Med Insights Oncol, 8, 71-76, 20 doi:10.4137/CMO.S9926.

Roy, R. et al., 2021, "DNA methylation signatures reveal that distinct combinations of transcription factors specify human immune cell epigenetic identity." Immunity, Nov. 9, 2021 vol. 54, pp. 2465-2480, https://doi.org/10.1016/j.immuni.2021.10.001.

Chater-Diehl, E. et al. "Anatomy of DNA methylation signatures: Emerging insights and applications." The American Journal of Human Genetics, Aug. 5, 2021, vol. 108, No. 8, pp. 1359-1366, https://doi.org/10.1016/j.ajhg.2021.06.015.

Plos One, 2013, vol. 8, Issue 12, e82302.

Clinical Epigenetics, 2017, vol. 9, 8.

Takamasa, Takahashi et al., Estimation of the Fraction of Cancer Cells in a Tumor DNA Sample Using DNA Methylation, PLOS One, Dec. 2013, vol. 8, Issue 12, 1-10.

Feber Andrew et al., UroMark—a urinary biomarker assay for the detection of bladder cancer, Clinical Genetics (2017), 1-10.

Min-Ae Song et al., Elucidating the Landscape of Aberrant DNA Methylation in Hepatocellular Carcinoma, PLOS One, Feb. 2013, vol. 8, Issue 2, 1-12.

Datasheet: Epigenetics, Infinium HumanMethylation450 Beadchip, The ideal solution for affordable, large sample-size genome-wide DNA methylation studies, illumina.

Bennelli, Matteo et al., Genome Analysis, Tumor purity quantification by clonal DNA methylation signatures, Bioinformatics 34(10), Jan. 2018, 1642-1649.

European Patent Office, Extended European Search Report (EESR), Jun. 14, 2022.

Gastronenterology, 2013, vol. 145, No. 6, pp. 1424-1435, p. 1435. el-25.

Hepatology, 2012, vol. 55, No. 6, p. 1799-1808.

Genome Medicine, May 30, 2018, vol. 10, Article No. 42, p. 1-11.

Briefings in Bioinformatics, 2016, vol. 19, No. 1 (2018), p. 101-108.

Hepatogastroenterology, Nov. 2005, vol. 52, No. 66, pp. 1854-1857.

FEBS Open Bio, May 2018, vol. 8, No. 7, pp. 1093-1103.

* cited by examiner ctDNA markers for HCC from Sun Yat Sen University Cancer hospital Normal tissues        Adjacent liver        HCC

HKG-epiLiver: Discovery

A

|  | Source | N | Purpose |
|---|---|---|---|
| Normals | GSE61258 | 79 | Detect |
| HCC | TCGA | 66 | Detect |
| HCC | TCGA | 10 | Spec |
| Other Cancers | TCGA | 80 | Spec |

B     "Detect"

Normal          HCC

C     "Spec"

HCC     8 different Cancer types

HKG-epi Liver-detect: Validation GSE76269

A

B

| sensitivity | 0.96 |
|---|---|
| specificity | 1 |
| accuracy | 0.97 |
| AUC | 0.98 |

C

HKG-epiLiver: Summary

HKG-epiLung: Discovery

A

|              | Source    | N  | Description |
|--------------|-----------|----|-------------|
| Normals      | GSE61258  | 10 | Detect  |
| Lung cancer  | TCGA      | 10 | Detect  |
| Lung cancer  | TCGA      | 10 | Spec        |
| Other Cancers | TCGA     | 80 | Spec        |

"Detect"

"Spec"

B

C

HKG-epiProstate: Discovery

A

|  | Source | N | Purpose |
|---|---|---|---|
| Normals | GSE52955 | 5 | Detect |
| PRAD | TCGA | 10 | Detect |
| PRAD | TCGA | 10 | Spec |
| Other Cancers | TCGA | 80 | Spec |

B        "Detect"

C        "Spec"

HKG-epiProstate: Summary

HKG-epiBreast: Discovery

A

|  | Source | N | Purpose |
|---|---|---|---|
| Normals | GSE60185 | 17 | Detect |
| Breast Cancer | TCGA | 10 | Detect |
| Breast Cancer | TCGA | 10 | Spec |
| Other Cancers | TCGA | 80 | Spec |

B                "Detect"                C                "Spec"

HKG-epiBreast: Summary

| sensitivity | 0.87 |
| --- | --- |
| specificity | 0.89 |
| accuracy | 0.91 |
| AUC | 0.94 |

HKG-epiCRC: Discovery

A

|  | Source | N | Description |
|---|---|---|---|
| Normals | GSE32146 | 25 | Detect |
| CRC | TCGA | 50 | Detect |
| CRC | TCGA | 10 | Spec |
| Other Cancers | TCGA | 80 | Spec |

B    "Detect"                    C    "Spec"

HKG-epiCRC: Summary

HKG-epiPancreas: Discovery

A

|  | Source | N | Description |
|---|---|---|---|
| Healthy | GSE53051 | 12 | Detect |
| PANC | TCGA | 20 | Detect |
| PANC | TCGA | 20 | Spec |
| Other Cancers | TCGA | 100 | Spec |

"Detect"

B

"Spec"

C

HKG-epiPancreas: Summary

A

B

C

| sensitivity | 0.86 |
|---|---|
| specificity | 0.93 |
| accuracy | 0.98 |
| AUC | 0.93 |

HKG-epiBrain(glioma): Discovery

A

| | Source | N | Description |
|---|---|---|---|
| Healthy | GSE65820 | 6 | Detect |
| Brain | TCGA | 10 | Detect |
| Brain | TCGA | 10 | Spec |
| Other Cancers | TCGA | 110 | Spec |

B

"Detect-Spec"

HKG-epiBrain (glioma): Summary

HKG-epiStomach-detect: Discovery

A

|  | Source | N | Purpose |
|---|---|---|---|
| Stomach Cancer | TCGA | 7 | Spec |
| Other Cancers | TCGA | 100 | Spec |
| Normals | GSE99553 | 14 | Detect |
| Stomach Cancer | TCGA | 20 | Detect |

B

"Detect"

C

"Spec"

HKG-epiOvarian: Discovery

A

|  | Source | N | Description |
|---|---|---|---|
| Healthy | GSE65820 | 5 | Detect |
| Ovarian | TCGA | 10 | Detect |
| Ovarian | TCGA | 10 | Spec |
| Other Cancers | TCGA | 110 | Spec |

B     "Detect"

C     "Spec"

HKG-epiOvarian: Summary

HKG-epiCervix: Discovery

A

|  | Source | N | Purpose |
|---|---|---|---|
| Normals | GSE46306 | 20 | Detect |
| Cervix | TCGA | 10 | Detect |
| Cervix | TCGA | 10 | Spec |
| Other Cancers | TCGA | 80 | Spec |

B    "Detect"

C    "Spec"

HKG-epiCervix: Summary

HKG-epiHNSC: Discovery

A

|  | Source | N | Description |
|---|---|---|---|
| Healthy | GSE75537 | 10 | Detect |
| HNSC | TCGA | 20 | Detect |
| HNSC Cancer | TCGA | 20 | Spec |
| Other Cancers | TCGA | 190 | Spec |
| Normal Blood | GSE40279 | 10 | Spec |

B

Detect

C

Spec

HKG-epiHNC: Summary

A

B

C

| sensitivity | 0.88 |
|---|---|
| specificity | 0.86 |
| accuracy | 0.94 |
| AUC | 0.92 |

HKG-epiEsophageal cancer: Discovery

A

|  | Source | N | Purpose |
|---|---|---|---|
| Normals | GSE52826 | 6 | Detect |
| Esopagheal Cancer | TCGA | 10 | Detect |
| Non-esophageal Cancers | TCGA | 190 | Spec |
| Healthy blood | GSE40279 | 10 | Spec |
| Esophageal Cancer | TCGA | 20 | Spec |

B

Detect

C

Spec

HKG-epiEsophageal cancer: Summary

HKG-epiBladder: Discovery

A

| | Source | N | Description |
|---|---|---|---|
| Healthy tissue | GSE52955 | 5 | detect |
| Bladder Cancer | TCGA | 10 | detect |
| Bladder Cancer | TCGA | 10 | spec |
| Other Cancers | TCGA | 180 | spec |

B          "Detect"

C          "Spec"

HKG-epiBladder: Summary

HKG-epiKidney: Discovery

A

|  | Source | N | Purpose |
|---|---|---|---|
| Other cancers | TCGA | 180 | Detect-Spec |
| Healthy Blood | GSE40279 | 10 | Detect-Spec |
| Normal Kidney | GSE52955 | 6 | Detect-Spec |
| Kidney | TCGA | 30 | Detect-Spec |

B

"Detect-Spec"

HKG-epiKidney: Summary

HKG-epiTestis: Discovery

A

|  | Source | N | Purpose |
|---|---|---|---|
| Other cancers and blood | GSE46306 | 180 | Detect-Spec |
| Testis | TCGA | 10 | Detect-Spec |

B

"Detect-Spec"

HKG-epiTestis: Summary sensitivity   0.96
specificity   0.97
accuracy      0.99
AUC           0.98

HKG epiPanCancer Discovery

A

|  | Source | N | Purpose |
|---|---|---|---|
| Healthy Blood | GSE40279 | 10 | Detect |
| TCGA_cancers | TCGA | 170 | Detect |

B

HK-epiPancancer Summary

A

B

C

| sensitivity | 0.95 |
|---|---|
| specificity | 0.99 |
| accuracy | 0.96 |
| AUC | 0.99 |

Pan-cancer markers: 13 localizations, controls: 968 healthy blood control

HKG-epiMelanoma: Discovery

A

|  | Source | N | Purpose |
|---|---|---|---|
| Melanoma (SKCM) | TCGA | 10 | Detect-Spec |
| Other cancers and blood | TCGA | 220 | Detect-Spec |

B

"Detect-Spec"

HKG-epiMelanoma: Summary

| sensitivity | 0.98 |
|---|---|
| specificity | 0.95 |
| accuracy | 0.94 |
| AUC | 0.95 |

Figure 41

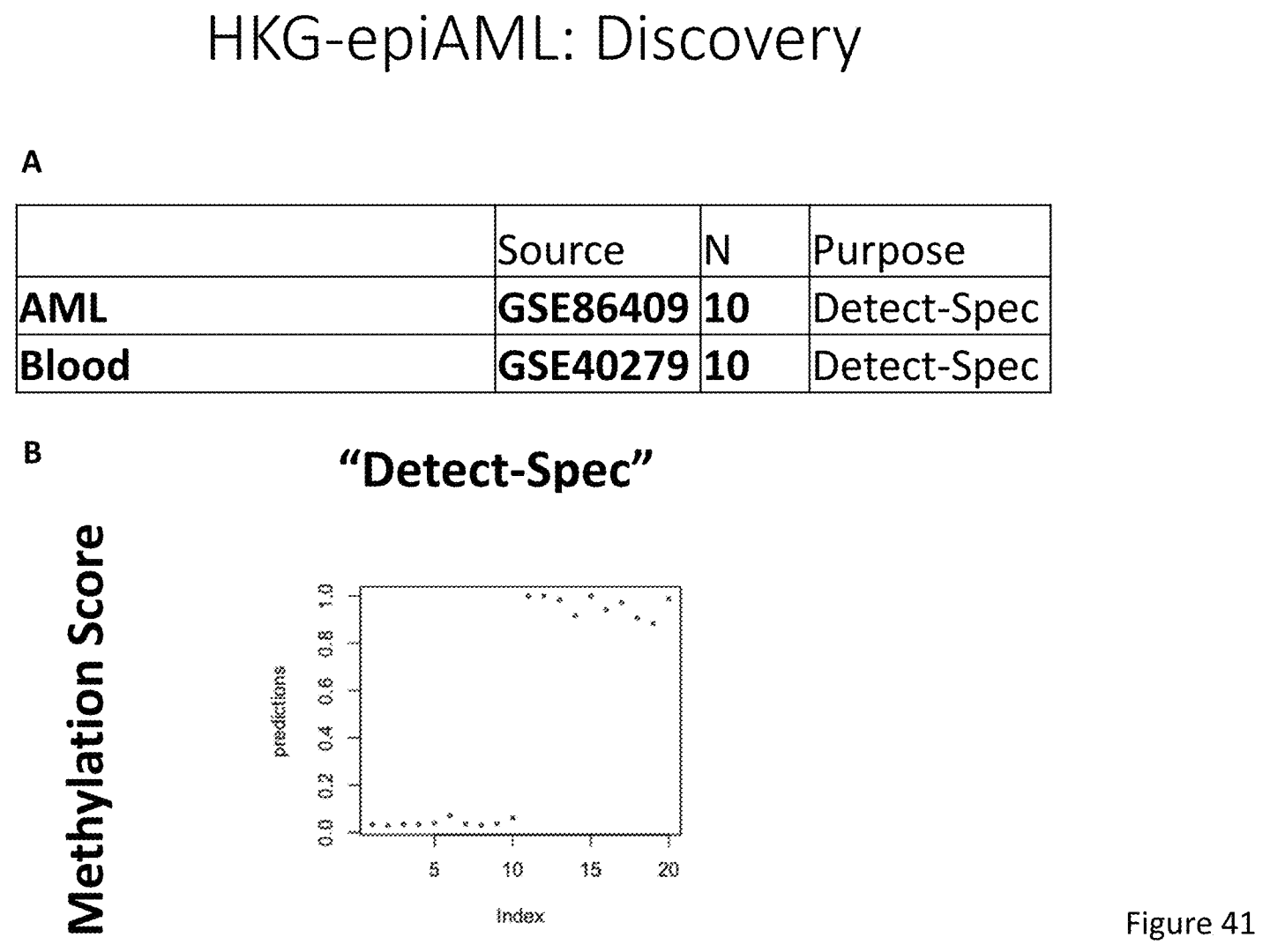

HKG-epiAML: Discovery

A

| | Source | N | Purpose |
|---|---|---|---|
| AML | GSE86409 | 10 | Detect-Spec |
| Blood | GSE40279 | 10 | Detect-Spec |

B

"Detect-Spec"

Methylation Score

HKG-epiAML: Summary

BCD validation on healthy plasma

Bioinformatics workflow

DNA METHYLATION MARKERS FOR NONINVASIVE DETECTION OF CANCER AND USES THEREOF

FIELD OF THE INVENTION

The present invention relates to DNA methylation signatures in human DNA, particularly in the field of molecular diagnostics.

SEQUENCE LISTING

The instant application contains a Sequence Listing which has been submitted electronically in ASCII format and is hereby incorporated by reference in its entirety. Said ASCII copy, created on Jan. 16, 2025, is named P5198US00 Sequence listing.txt and is 10,750 bytes in size.

BACKGROUND OF THE INVENTION

Cancer has become a major killer of humans. Early detection of cancer can significantly improve cure rates and reduce the horrific personal and financial cost to the patients their families and the health care system. For example, Hepatocellular Carcinoma (HCC) is the fifth most common cancer world-wide (EI-Serag, 2011). It is particularly prevalent in Asia, and its occurrence is highest in areas where hepatitis B is prevalent, indicating a possible causal relationship (Flores & Marrero, 2014). Follow up of high-risk populations such as chronic hepatitis patients and early diagnosis of transitions from chronic hepatitis to HCC would improve cure rates. The survival rate of hepatocellular carcinoma is currently extremely low because it is almost always diagnosed at the late stages. Liver cancer could be effectively treated with cure rates of >80% if diagnosed early. Advances in imaging have improved noninvasive detection of HCC (Tan, Low, & Thng, 2011; Valente et al., 2014). However, current diagnostic methods, which include imaging and immunoassays with single proteins such as alpha-fetoprotein often fail to diagnose HCC early (Flores & Marrero, 2014). These challenges are not limited to HCC but common to other cancers as well. For example, early detection of breast cancer and colorectal cancer could dramatically reduce morbidity and mortality and the cost to the public health system and insurance companies. Moreover, certain cancers such as pancreatic cancers are detected almost invariably late resulting in virtually certain mortality. Advances in imaging have improved early detection of cancers, however high-resolution imaging such as MRI is expensive, requires highly trained personnel and is unavailable in many locations. It has not evolved yet to a method of screening of wide populations. To have an impact on reducing morbidity and mortality from cancer it is necessary to develop a noninvasive, robust but nevertheless low-cost method that could be used in wide geographic areas for routine screening of the population. The main challenge is that solid tumors hide in internal organs and evolve long before they exhibit clinical symptoms. It is however possible to obtain tumor material noninvasively.

It is widely established by now that tumor DNA is shed into the system and could be found in plasma (Warton & Samimi, 2015) and possibly other secreted body fluids such as urine and saliva, as well as feces. By measuring molecular characteristics of tumor DNA, it is possible to determine that the DNA found in body fluids originated in the tumor (Zhai et al., 2012). Although tumor cells develop mutations that could distinguish tumor DNA from normal cells DNA, the number of possible mutations is vast and common mutations don't occur in all tumors (Dominguez-Vigil, Moreno-Martinez, Wang, Roehrl, & Barrera-Saldana, 2018).

DNA methylation, a covalent modification of DNA, which is a primary mechanism of epigenetic regulation of genome function is ubiquitously altered in tumors (Aguirre-Ghiso, 2007; Baylin et al., 2001; Ehrlich, 2002; Issa et al., 1993). DNA methylation profiles of tumors are potentially robust tools for tumor classification, prognosis and prediction of response to chemotherapy (Stefansson et al., 2014). The major drawback for using tumor DNA methylation in early diagnosis is that it requires invasive procedures and anatomical visualization of the suspected tumor. Circulating tumor cells are a noninvasive source of tumor DNA and are used for measuring DNA methylation in tumor suppressor genes (Radpour et al., 2011). Hypomethylation of HCC DNA is detectable in patients' blood (Ramzy, Omran, Hamad, Shaker, & Abboud, 2011) and genome wide bisulfite sequencing was recently applied to detect hypomethylated DNA in plasma from HCC patients (Chan et al., 2013). However, this source is limited, particularly at early stages of cancer and the DNA methylation profiles are confounded by host DNA methylation profiles. Genome wide bisulfite sequencing is a relatively costly procedure and requires significant bioinformatics analysis which makes it unfeasible as a screening tool. The challenge is therefore to delineate a small number of CGs that could robustly differentiate tumor DNA from nontumor DNA and develop a high throughput low cost assay that will enable the screening of wide populations in broad and diverse geographic areas. More recently several groups have performed comparative analysis of genome wide DNA methylation maps of cancer and normal DNA and blood DNA (Zhai et al., 2012). However, the main challenge with these approaches is that they have not taken into account cell free DNA from other tissues that is found in blood at different levels that are unanticipated a priori. Contaminating DNA from another tissue that has a similar methylation profile as the cancer tissue could lead to false positives. In addition, past approaches have quantitatively compared DNA methylation in normal and cancer tissues. This quantitative difference is diluted when tumor DNA is mixed with different and unknown amounts of DNA from other untransformed tissues, which can cause false negatives. These deficiencies in current methods necessitate a different approach that is disclosed in the present inventive subject matter.

Further publications dealing with the use of systems and methods for detecting cancer are: Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. 1997 March; 6(3):387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. 1995 May 19; 157(1-2):261-4; WO 97 46705, WO 95 15373 and WO 45560. Aguirre-Ghiso, J. A. (2007). Models, mechanisms and clinical evidence for cancer dormancy. *Nat Rev Cancer,* 7(11), 834-846. doi:10.1038/nrc2256

Baylin, S. B., Esteller, M., Rountree, M. R., Bachman, K. E., Schuebel, K., & Herman, J. G. (2001). Aberrant patterns of DNA methylation, chromatin formation and gene expression in cancer. Hum Mol Genet, 10(J), 687-692.

Breitbach, S., Tug, S., Helmig, S., Zahn, D., Kubiak, T., Michal, M., . . . Simon, P. (2014). Direct quantification of cell-free, circulating DNA from unpurified plasma. PLoS One, 9(3), e87838. doi:10.1371/journal.pone.0087838

Chan, K. C., Jiang, P., Chan, C. W., Sun, K., Wong, J., Hui, E. P., . . . Lo, Y. M. (2013). Noninvasive detection of cancer-associated genome-wide hypomethylation and copy number aberrations by plasma DNA bisulfite sequencing. Proc Natl Acad Set USA, 110(47), 18761-18768. doi: 10.1073/pnas,1313995110

Dominguez-Vigil, I. G., Moreno-Martinez, A. K., Wang, J. Y., Roehrl, M. H. A., & Barrera-Saldana, H. A. (2018). The dawn of the liquid biopsy in the fight against cancer. Oncotarget, 9(2), 2912-2922. doi:10.18632/oncotarget.23131

Ehrlich, M. (2002). DNA methylation in cancer: too much, but also too little. Oncogene, 27(35), 5400-5413.

EI-Serag, H. B. (2011). Hepatocellular carcinoma. NEnglIJMed, 365(12), 1118-1127. doi:10.1056/NEJMral001683

Flores, A., & Marrero, J. A. (2014). Emerging trends in hepatocellular carcinoma: focus on diagnosis and therapeutics. Clin Med Insights Oncol, 8, 71-76. doi:10.4137/CMO.S9926

Issa, J. P., Vertino, P. M., Wu, J., Sazawal, S., Celano, P., Nelkin, B. D., . . . Baylin, S. B. (1993). Increased cytosine DNA-methyltransferase activity during colon cancer progression. J Natl Cancer Inst, 55(15), 1235-1240.

Luczak, M. W., & Jagodzinski, P. P. (2006). The role of DNA methylation in cancer development. Folia Histochem Cytobiol, 44(3), 143-154.

Radpour, R., Barekati, Z., Kohler, C., Lv, Q., Burki, N., Diesch, C., . . . Zhong, X. Y. (2011). Hypermethylation of tumor suppressor genes involved in critical regulatory pathways for developing a blood-based test in breast cancer. PLoS One, 6(1), e16080. doi:10.1371/journal.pone.001608C.

Ramzy, II, Omran, D. A., Hamad, O., Shaker, O., & Abboud, A. (2011). Evaluation of serum LINE-1 hypomethylation as a prognostic marker for hepatocellular carcinoma. Arab J Gastroenterol, 12(3), 139-142. doi:10.1016/j.ajg.2011.07.002

Stefansson, O. A., Moran, S., Gomez, A., Sayols, S., Arribas-Jorba, C., Sandoval, I, . . . Esteller, M. (2014). ADNA methylation-based definition of biologically distinct breast cancer subtypes. Mol Oncol, doi:10.1016/j.molonc.2014.10.012

Tan, C. H., Low, S. C., & Thng, C. H. (2011). APASL and AASLD Consensus Guidelines on Imaging Diagnosis of Hepatocellular Carcinoma: A Review. IntJ Hepatol, 2011, 519783. doi:10.4061/2011/519783

Valente, S., Liu, Y., Schnekenburger, M., Zwergel, C., Cosconati, S., Gros, C., . . . Mai, A. (2014). Selective non-nucleoside inhibitors of human DNA methyltransferases active in cancer including in cancer stem cells. J Med Chem, 57(3), 701-713. doi:10.1021/jm4012627

Warton, K., & Samimi, G. (2015). Methylation of cell-free circulating DNA in the diagnosis of cancer. Front Mol Biosci, 2, 13. doi:10.3389/fmolb.2015.00013

Xu, R. H., Wei, W., Krawczyk, M., Wang, W., Luo, H., Flagg, K., . . . Zhang, K. (2017). Circulating tumour DNA methylation markers for diagnosis and prognosis of hepatocellular carcinoma. Nat Mater, 76(11), 1155-1161. doi: 10.1038/nmat4997

Zhai, R., Zhao, Y., Su, L., Cassidy, L., Liu, G., & Christiani, D. C. (2012). Genome-wide DNA methylation profiling of cell-free serum DNA in esophageal adenocarcinoma and Barrett esophagus. Neoplasia, 14(1), 29-33.

SUMMARY OF THE INVENTION

Embodiments of the claimed subject matter show that cancer is associated with a set of "categorically" distinct DNA methylation signatures that are different from any normal tissue and blood cell DNA methylation profiles. These sites create a binary differentiation between cancer and other tissues, whereby these sites are only methylated in cancer and fully unmethylated in other cancers. Thus, it is possible using deep next generation sequencing to detect even a few molecules of cancer cells on the background of normal cell DNA profile of methylation. Embodiments of the inventive subject matter enable detection of cell free tumor DNA even on a high background of cell free DNA from other tissues and are thus particularly suitable for early detection of cancer using cell free (CF) DNA extracted from body fluids, for example saliva, plasma, urine, feces etc. Embodiments also allow for early detection of cancer in tissue smears such as pup smears as well as biopsies and needle biopsies. Previous analyses in the prior art only compared normal and cancer cells from the same tissue and blood and derived sites that are quantitatively different in their DNA methylation level (Xu et al., 2017). However, sites discovered by such prior art analyses can't detect CF tumor DNA when it is mixed with other tissue CF DNA (see FIG. 2 for ctDNA markers for HCC from Sun Yat Sen University Cancer hospital). One embodiment of the present claimed subject matter reveals a unique set of sites that are unmethylated in all tissues but methylated in specific cancers. Another embodiment reveals a method to discover categorically distinct methylation sites in cancers, other tissues and other diseases called the "binary-categorical differentiation (BCD) method" using different sources of genome wide DNA methylation data derived by next generation sequencing, MeDIP arrays, MeDIP sequencing, and the like. One embodiment reveals a combination of "Categorical" DNA methylation sites for detection of a. hepatocellular carcinoma (HCC), b. lung cancer, c. prostate cancer, d. breast cancer, e. colorectal cancer, f. head and neck squamous cell carcinoma (HNSC). g. pancreatic cancer, h. brain cancer (glioblastoma), i. gastric cancer j. ovarian cancer, k. cervical cancer, I. esophageal carcinoma m. bladder cancer, n. renal cancer, o. testicular cancer, p. common solid tumors, q. blood cancer profiles in a discovery set of genome wide data. Another embodiment also reveals a combination of "Categorical" DNA methylation sites that differentiate tumors by their tissue of origin. This embodiment differentiates the assay from prior art methods for detecting methylated CF DNA which have low tissue specificity. Embodiments validate the polygenic DNA methylation assays for detection of cancer in DNA methylation data from hundreds of patients as well as the tissue of origins of the tumors with high sensitivity and specificity. The present invention discloses a method that accurately measures DNA methylation in a polygenic set of CG IDs in hundreds of people concurrently, by sequential amplification with target specific primers followed by barcoding primers and multiplexed sequencing in a single next generation Miseq sequencing reaction, data extraction and quantification of methylation from a small volume of body fluids such as plasma, saliva or urine. Another embodiments of the inventive subject matter also discloses measurement of methylation of the said DNA methylation CG IDs using pyrosequencing assays or methylation specific PCR. Another embodiment discloses the calculation of either a "categorical" or a polygenic weighted methylation score that differentiates people with cancer from healthy people. Another embodiment discloses a novel process leading from plasma, urine, feces, tissue biopsy or tissue swabs to prediction of cancer in a person with no other clinical evidence for cancer. Another embodiment could be used by any person skilled in the art to detect cancer as well as other diseases that involve cell death and release of CF DNA such Alzheimer disease and other neurodegenerative diseases for neurons, heart disease for heart muscle cells. The DNA methylation markers (CG IDs) described in the embodiments will be utilized for a. noninvasive early detection of cancer in otherwise "healthy" people through routine "checkup"; b. monitoring "high risk" people such as chronic hepatitis patients who are at high risk for HCC or smokers who are at high risk for lung feces, urine and tissues of any cancer or diseased tissue using any method for methylation analysis that are available to those skilled in the art such as for example next generation bisulfite sequencing, Illumina Epic microarrays, capture sequencing, methylated DNA Immunoprecipitation (MeDIP) methylation specific PCR and any methylation measurements that becomes available.

Embodiments also disclose the potential for discovery of new "polygenic" categorical DNA methylation markers for other cancers and diseases using any method available to people skilled in the art for genome wide sequencing such as next generation bisulfite sequencing, MeDip sequencing, ion torrent sequencing, Epic microarrays etc. followed by binary-categorical differentiation (BCD) method of analysis for discovering specific and sensitive markers that will be used for noninvasive detection of disease.

Embodiments of the present inventive subject matter include:

In a first aspect, embodiments provide polygenic DNA methylation markers of cancer in cell free DNA in body fluids such as plasma for early detection of cancer, said polygenic DNA methylation markers set being derived using "binary-categorical differentiation (BCD) analysis" as disclosed herein on genome wide DNA methylation derived by mapping methods such as Illumina 450K or EPIC arrays, genome wide bisulfite sequencing, methylated DNA Immunoprecipitation (MeDIP) sequencing or hybridization with oligonucleotide arrays.

In other embodiments, the polygenic DNA methylation markers are a combination of CG IDs in the list below (or a short subset of this list such as the example listed below Table 1) for early detection of Liver cancer hepatocellular carcinoma (HCC) using plasma CF DNA or other body fluid CF DNA.

TABLE 1

| Liver_detect | | | | | |
|---|---|---|---|---|---|
| cg00370303 | cg10900437 | cg02012576 | cg16460359 | cg04035559 | cg17419241 |
| cg00931619 | cg11223367 | cg03768777 | cg16977570 | cg04085025 | cg18607529 |
| cg05040544 | cg19289599 | cg06233293 | cg24804544 | cg26523670 | cg09992116 |
| cg05739190 | cg24599205 | | | | | cancer; c. monitoring response to therapy in patients undergoing cancer treatment to detect recurrence or metastasis.

Embodiments demonstrate the utility detecting cancer of unknown samples using polygenic or categorical scores based on the DNA methylation measurement methods disclosed herein. The disclosed embodiments could be used by any person skilled in the art to detect cancer in body fluids, Subset for detect:
cg02012576, cg03768777, cg24804544, cg05739190

In other embodiments, the polygenic DNA methylation markers are a combination of CG IDs in the list below or a short subset of this list (as shown in the example shown below Table 2) for specifying the origin of the cancer as HCC and discriminating from other 10 common solid tumor cancers using plasma CF DNA or other body fluid DNA.

TABLE 2

| Liver_spec | | | | | |
|---|---|---|---|---|---|
| cg12137206 | cg14126493 | cg06105778 | cg22076972 | cg13341720 | cg03705926 |
| cg09363194 | cg07036412 | cg02702614 | cg10181419 | cg05876864 | cg11068343 |
| cg17167468 | cg15375239 | cg00026222 | cg17283781 | cg16147221 | cg26386472 |
| cg14570307 | cg06207432 | cg07610192 | cg03422204 | cg11684022 | cg23693289 |
| cg21107197 | cg04920951 | cg20385508 | cg25296314 | cg20707679 | cg26703661 |
| cg00456086 | cg05009389 | cg19388016 | cg08460435 | cg04739306 | cg04221886 |
| cg26797073 | cg04109768 | cg05337743 | cg00483503 | cg18668780 | cg10604002 |
| cg27650175 | cg05684891 | cg26026416 | cg00177496 | cg14221460 | cg16551483 |
| cg13438961 | cg24432073 | cg21059834 | cg23305567 | cg04809136 | cg21105227 |

7

8

Subset for specificity:
cg14126493
In other embodiments, the polygenic DNA methylation markers are a combination of CG IDs in the list below or a short subset of this list (such as the example listed below Table 3) for early detection of lung cancer using plasma CF DNA or other body fluid CF DNA.

TABLE 3

| Lung_detect | | | | | |
| --- | --- | --- | --- | --- | --- |
| cg04223424 | cg06530490 | cg08944430 | cg09463882 | cg11017065 | cg12405785 |
| cg16405026 | cg21410080 | cg23141355 | cg25024074 | | |

Subset for detect:
cg04223424, cg23141355
In other embodiments, the polygenic DNA methylation markers are a combination of CG IDs in the list below or a short subset of this list (as shown in the example listed below Table 4) for specifying the origin of the cancer as lung cancer and discriminating from other 10 common solid tumor cancers using plasma CF DNA or other body fluid DNA.

TABLE 4

| Lung_spec | | | | | |
| --- | --- | --- | --- | --- | --- |
| cg05917792 | cg02682457 | cg23407396 | cg23601095 | cg23141355 | cg15386964 |
| cg02578368 | cg24631970 | cg27487839 | cg16405026 | | |
| cg23141355 | cg06530490 | cg04223424 | cg25470077 | cg07138603 | cg23460835 |
| cg20678442 | cg15436096 | | | | |

Subset for spec:
cg05917732, cg25470077
In other embodiments, the polygenic DNA methylation markers are a combination of CG IDs in the list below (or a short subset of this list such as the example listed below Table 5) for early detection of prostate cancer as well as for specifying the origin of the cancer as prostate cancer and discriminating from other 16 common solid tumor cancers using plasma CF DNA or other body fluid CF DNA.

TABLE 5

| Subset for detect spec: |
| --- |
| cg14283569 |

[it is a subset of the 4 listed in the table above]
In other embodiments, the polygenic DNA methylation markers are a combination of CG IDs in the list below or a short subset of this list (such as the example listed below Table 6) for early detection of breast cancer using plasma CF DNA or other body fluid CF DNA.

TABLE 6

| Breast_detect | | | | | |
| --- | --- | --- | --- | --- | --- |
| cg13031251 | cg19595750 | cg16842053 | cg18565473 | cg09734791 | cg25694349 |
| cg09695735 | cg03637878 | cg26261793 | cg18800085 | cg16132520 | cg05617413 |
| cg17228900 | cg06945936 | cg08406370 | cg24427504 | cg26937500 | cg11297107 |
| cg02215070 | cg14140647 | cg05377226 | cg07070305 | cg24899571 | cg07844931 |

Subset for detect:

cgl3031251, cg09734791, cg09695735, cg03637878

In other embodiments, the polygenic DNA methylation markers are a combination of CG IDs in the list below or a short subset of this list (as shown in the example listed below Table 7) for specifying the origin of the cancer as breast cancer and discriminating from other 10 common solid tumor cancers using plasma CF DNA or other body fluid DNA.

TABLE 7

| Breast_Spec | | | | |
| --- | --- | --- | --- | --- |
| cg00467244 | cg04194674 | cg06879394 | cg10720997 | cg19966212 |
| cg00722320 | cg04751811 | cg06998282 | cg11498607 | cg24525457 |

TABLE 7-continued

| Breast_Spec | | | | |
| --- | --- | --- | --- | --- |
| cg01308827 | cg06282270 | cg08066035 | cg14862207 | cg26228266 |
| cg03113878 | cg06405186 | cg08296680 | cg17945153 | cg20180843 |

Subset for spec:

cg03113878, cg20180843

In other embodiments, the polygenic DNA methylation markers are a combination of CG IDs in the list below or a short subset of this list (such as the example listed below Table 8) for early detection of colorectal cancer (CRC) as well as for specifying the origin of the cancer as colorectal cancer and discriminating from other 16 common solid tumor cancers using plasma CF DNA or other body fluid CF DNA.

TABLE 8

| CRC_detect_spec | | | | | |
| --- | --- | --- | --- | --- | --- |
| cg08808128 | cg03788131 | cg09854653 | cg21627760 | cg08169901 | cg07494047 |
| cg01566242 | cgl3788592 | cg24102266 | cgl7716617 | cgl6733654 | |

Subset for detect-spec cg09854653, cg01566242

In other embodiments, the polygenic DNA methylation markers are a combination of CG IDs in the list below or a short subset of this list (such as the example listed below Table 9) for early detection of pancreatic cancer using plasma CF DNA or other body fluid CF DNA.

TABLE 9

| Pancreas_detect | | | | | |
| --- | --- | --- | --- | --- | --- |
| cg11017065 | cg23833588 | cg25024074 | cg21277995 | cg22286978 | cg06241792 |
| cg11591516 | cg10096177 | cg12035092 | cg03611007 | cg17996329 | cg13807970 |
| cg16678602 | cg15386964 | cg01423964 | cg07900968 | cg19118812 | cg06728579 |
| cg16232979 | cg08406370 | | | | |

Subset for detect:

cg25024074, cgl5386964, cgl6232979

In other embodiments, the polygenic DNA methylation markers are a combination of CG IDs in the list below or a short subset of this list (as shown in the example listed below Table 10) for specifying the origin of the cancer as pancreatic cancer and discriminating from other 10 common solid tumor cancers using plasma CF DNA or other body fluid DNA.

TABLE 10

| Pancreas_Spec | | | | | |
| --- | --- | --- | --- | --- | --- |
| cg01237565 | cg08182975 | cg15323936 | cg19102272 | cg01311909 | cg26927232 |
| cg22290704 | cg15832577 | cg29983577 | cg26466027 | cg09796911 | cg15850155 |
| cg15510118 | cg25591377 | cg16165258 | cg25595541 | cg18151519 | cg19749445 |
| cg14870128 | cgl3441142 | | | | |

Subset for spec:

cg01237565, cg08182975, cg20983577, cg25591377

In other embodiments, the polygenic DNA methylation markers are a combination of CG IDs in the list below or a short subset of this list (such as the example listed below Table 11) for early detection of brain cancer (glioblastoma) as well as for specifying the origin of the cancer as brain cancer (glioblastoma) and discriminating from other 10 common solid tumor cancers using plasma CF DNA or other body fluid CF DNA.

TABLE 11

| Brain_detect-spec | | | | | |
|---|---|---|---|---|---|
| cg06887260 | cg19116006 | cg10938374 | cg03663746 | cg25568243 | cg27449131 |
| cg24917627 | cg04134305 | cg09797645 | cg02892595 | cg13231951 | cg26269703 |
| cg09183941 | cg16842053 | cg26551897 | cg26988692 | cg07849581 | cg25026703 |
| cg06798642 | cg22963915 | cg04245373 | cg25533556 | cg24917627 | cg27659841 |
| cg04692993 | cg06045408 | cg06887260 | cg11345323 | cg17167076 | cg17526812 |
| cg19929355 | cg22513169 | cg22865720 | | | |

Subset for spec-detect
cg19929355

In other embodiments, the polygenic DNA methylation markers are a combination of CG IDs in the list below or a short subset of this list (such as the example listed below Table 12) for early detection of stomach (gastric) cancer using plasma CF DNA or other body fluid CF DNA.

TABLE 12

| Stomach_detect | | | | | |
|---|---|---|---|---|---|
| cg04125371 | cg05377226 | cg05611779 | cg06241792 | cg07900968 | cg09734791 |
| cg11017065 | cg12510981 | cg13807970 | cg15760257 | cg18323466 | cg19118812 |
| cg19419279 | cg19769760 | cg20334243 | cg26261793 | | |

Subset for detect:
cg05611779, cg09734791, cg15760257

In other embodiments, the polygenic DNA methylation markers are a combination of CG IDs in the list below or a short subset of this list (as shown in the example shown below Table 13) for specifying the origin of the cancer as gastric cancer and discriminating from other 10 common solid tumor cancers using plasma CF DNA or other body fluid DNA.

TABLE 13

| Stomach_Spec | | | | | |
|---|---|---|---|---|---|
| cg17187167 | cg07350470 | cg05000488 | cg25612145 | cg09851120 | cg00904726 |
| cg04911739 | cg18192294 | cg11861709 | cg19452853 | cg02706110 | cg03768513 |
| cg05611779 | cg06981182 | cg06118999 | cg04812509 | cg10131095 | cg05339066 |
| cg19235339 | | | | | |

Subset for spec:
cg05611779, cg19235339

In other embodiments, the polygenic DNA methylation markers are a combination of CG IDs in the list below or a short subset of this list (such as the example shown below Table 14) for early detection of ovarian cancer using plasma CF DNA or other body fluid CF DNA.

TABLE 14

| Ovarian_detect | | | | | |
|---|---|---|---|---|---|
| cg24339193 | cg04008429 | cg06849719 | cg22694153 | cg11252337 | cg15804105 |
| cg12479674 | cg06961071 | cg21210985 | cg01556502 | cg02537149 | cg23983315 |
| cg03597143 | cg27209395 | | | | |

Subset for detect:
cg24339193, cg22694153, cg11252337, cg21210985

In other embodiments, the polygenic DNA methylation markers are a combination of CG IDs in the list below or a short subset of this list (as shown in the example listed below Table 15) for specifying the origin of the cancer as ovarian cancer and discriminating from other 10 common solid tumor cancers using plasma CF DNA or other body fluid DNA.

TABLE 15

| Ovarian_spec | | | | | |
|---|---|---|---|---|---|
| cg00895834 | cg01159194 | cg01961086 | cg02649698 | cg03345116 | cg03456771 |
| cg09392827 | cg10178270 | cg10581012 | cg13459217 | cg15701612 | cg17130982 |
| cg05901462 | cg07068768 | cg08389588 | cg09173621 | cg19276014 | cg19846609 |
| cg18476766 | cg19129687 | | | | |

Subset for spec:
cg07068768, cgl9846609
In other embodiments, the polygenic DNA methylation markers are a combination of CG IDs in the list below or a short subset of this list (such as the example shown below Table 16) for early detection of cervical cancer using plasma CF DNA or other body fluid CF DNA.

TABLE 16

| Cervix_detect | | | | | |
|---|---|---|---|---|---|
| cg00578154 | cgl3644629 | cg01423964 | cg15745619 | cg04522671 | cg21621906 |
| cg00757182 | cgl4962363 | cg01601746 | cg17228900 | cg07126167 | cg22806837 |
| cg08134106 | cg22922289 | cg09260640 | cg24625128 | cgl1259628 | cg27420520 |
| cg08535260 | cg23141355 | cg09734791 | cg25024074 | | |

Subset for detect:
cg00757182, cgO1601746
In other embodiments, the polygenic DNA methylation markers are a combination of CG IDs in the list below or a short subset of this list (as shown in the example listed below Table 17) for specifying the origin of the cancer as cervical cancer and discriminating from other 10 common solid tumor cancers using plasma CF DNA or other body fluid DNA.

TABLE 17

| Cervix_spec | | | | | |
|---|---|---|---|---|---|
| cg00829990 | cg02401399 | cg04996219 | cg07066594 | cg07195011 | cg07576142 |
| cg09260640 | cgl2961842 | cg13668618 | cg18543270 | | |

Subset for spec:
cg07066594, cg09260640, cgl2961842
In other embodiments, the polygenic DNA methylation markers are a combination of CG IDs in the list below or a short subset of this list (such as the example listed below Table 18) for early detection of head and neck squamous cell carcinoma (HNSC) carcinoma using plasma CF DNA or other body fluid CF DNA.

TABLE 18

| HNSC_detect | | | | | |
|---|---|---|---|---|---|
| cg01613638 | cg02776314 | cg03280624 | cg04524120 | cg05151803 | cg07746323 |
| cg07900968 | cg08406370 | cg11108676 | cg12083965 | cg15397448 | cg17428324 |
| cg18403606 | cg20334243 | cg26770917 | cg27009208 | cg27420520 | |

Subset for detect:
cg07900968, cg20334243, cg27420520
In other embodiments, the polygenic DNA methylation markers are a combination of CG IDs in the list below or a short subset of this list (as shown in the example listed below Table 19) for specifying the origin of the cancer as head and neck squamous cell carcinoma (HNSC) and discriminating from other 10 common solid tumor cancers using plasma CF DNA or other body fluid DNA.

TABLE 19

| HNSC_spec | | | | | |
|---|---|---|---|---|---|
| cg01217080 | cg03522799 | cg06672120 | cg09136346 | cg10155875 | cg18006328 |
| cg18443253 | cg19287220 | | | | |

Subset for spec:
cgl8006328, cgl9287220

In other embodiments, the polygenic DNA methylation markers are a combination of CG IDs in the list below or in a short subset of this list (such as the example listed below Table 20) for early detection of esophageal carcinoma using plasma CF DNA or other body fluid CF DNA.

TABLE 20

| Esophagus_detect | | | | | |
|---|---|---|---|---|---|
| cg03280624 | cg03735888 | cg06530490 | cg06963053 | cg08944430 | cg09734791 |
| cg11017065 | cg12035092 | cg18344922 | cg19118812 | cg20334243 | cg22128431 |
| cg23141355 | cg24740531 | cg27009208 | cg27420520 | | |

Subset for detect:
cg03280624, cg03735888, cg09734791, cg27420520

In one embodiment, the polygenic DNA methylation markers are a combination of CG IDs in the list below or a short subset of this list (as shown in the example listed below Table 21) for specifying the origin of the cancer as esophageal carcinoma and discriminating from other 10 common solid tumor cancers using plasma CF DNA or other body fluid DNA.

TABLE 21

| Esophagus_spec | | | | | |
|---|---|---|---|---|---|
| cg00532449 | cg02763101 | cg04743654 | cg08055087 | cg08932440 | cg09556952 |
| cg10608333 | cg12473285 | cg12966367 | cg17579667 | cg17949440 | cg18723937 |
| cg21554552 | cg22647407 | cg23286646 | cg23730575 | cg27569446 | |

Subset for spec:
cg09556952, cg12473285

In other embodiments, the polygenic DNA methylation markers are a combination of CG IDs in the list below or a short subset of this list (such as the example listed below Table 22) for early detection of bladder cancer using plasma CF DNA or other body fluid CF DNA.

TABLE 22

| Bladder_detect | | | | | |
|---|---|---|---|---|---|
| cg01423964 | cg04223424 | cg01556502 | cg23141355 | cg10723962 | cg09734791 |
| cg25024074 | cg21039778 | cg19113641 | cg04342821 | cg09008417 | cg05873285 |

Subset for detect:
cg04223424, cg10723962, cg25024074

In other embodiments, the polygenic DNA methylation markers are a combination of CG IDs in the list below or a short subset of this list (as shown in the example listed below Table 23) for specifying the origin of the cancer as bladder cancer and discriminating from other 10 common solid tumor cancers using plasma CF DNA or other body fluid DNA.

TABLE 23

Bladder_spec

| | | | | | |
|---|---|---|---|---|---|
| cg14773260 | cg08827322 | cg05085809 | cg13544006 | cg02293936 | cg10153335 |
| cg05039004 | cg14718568 | cg07790170 | cg12995090 | cg16495265 | cg01508045 |
| cg04933208 | cg03231163 | cg06708937 | cg00675569 | cg06312813 | cg14126688 |
| cg12984729 | cg02384661 | cg08307030 | cg26884027 | cg20540209 | cg04355159 |
| cg08857479 | cg23395715 | cg22006640 | cg26279336 | cg19898108 | cg17446010 |
| cg12911122 | | | | | |

Subset for spec:
cg13544006

In other embodiments, the polygenic DNA methylation markers are a combination of CG IDs in the list below or a short subset of this list (such as the example listed below Table 24) for early detection of renal (kidney) cancer for specifying the origin of the cancer as renal cancer and discriminating from other 10 common solid tumor cancers using plasma CF DNA or other body fluid CF DNA.

TABLE 24

Kidney_detect_spec

| | | | | | |
|---|---|---|---|---|---|
| cg08884571 | cg00011225 | cg14535274 | cg05507490 | cg10367244 | cg07190763 |
| cg02971546 | cg19990785 | cg03084949 | cg08765317 | cg02820958 | cg23946709 |
| cg26642667 | | | | | |

Subset for detect spec:
cg08884571, cg00011225, cg00011225

In other embodiments, the polygenic DNA methylation markers are a combination of CG IDs in the list below or a short subset of this list (such as shown in the example listed below Table 25) for early detection of testicular cancer for specifying the origin of the cancer as testicular cancer and discriminating from other 10 common solid tumor cancers using plasma CF DNA or other body fluid CF DNA.

TABLE 25

Testicular_detect_spec

| | | | | | |
|---|---|---|---|---|---|
| cg14531093 | cg11777290 | cg13283877 | cg03966099 | cg26939375 | cg26297530 |
| cg16157016 | cg14002772 | cg09890687 | cg05134918 | cg09719850 | cg06456125 |
| cg17978367 | cg20100671 | cg26627956 | cg19789755 | cg14393609 | cg21634331 |
| cg02039634 | cg25159927 | cg01895439 | | | |

Subset for detect and spec:
cg14531093, cg25159927

In other embodiments, the polygenic DNA methylation markers are a combination of CG IDs in the list below or a short subset of this list such (as shown in the example listed below Table 26) for early detection of one of 13 most common solid tumors using plasma CF DNA or other body fluid CF DNA.

TABLE 26

Pan-cancer_detect

| | | | | | |
|---|---|---|---|---|---|
| cg01423964 | cg04223424 | cg06530490 | cg06543087 | cg07900968 | cg08406370 |
| cg08848774 | cg09734791 | cg10723962 | cg11017065 | cg15759056 | cg15760257 |
| cg16405026 | cg17228900 | cg21277995 | cg22286978 | cg23141355 | cg24427504 |
| cg25024074 | cg27420520 | | | | |

Subset for detect:

cg10723962, cg15759056, cg24427504, cg25024074

In other embodiments, the polygenic DNA methylation markers are a combination of CG IDs delineated by the BCD method on genome wide DNA methylation data as shown in Table 27 (or a short subset of this combination as shown below Table 27) for early detection of blood cancers such as AML, CLL, etc. using white blood cells, plasma CF DNA or other body fluid CF DNA.

TABLE 27

| AML_detect-spec | | | | | |
|---|---|---|---|---|---|
| cg00594866 | cg05608159 | cg18658397 | cg18780412 | cg20430388 | cg22828045 |
| cg25375340 | | | | | |

Subset for detect-spec:

cg18658397, cg18780412, cg20439288, cg22828045, cg25375340

In other embodiments, the polygenic DNA methylation markers are a combination of CG IDs shown in the list below (or a short subset of this list shown in the example listed below Table 28) for early detection of Melanoma for specifying the origin of the cancer as melanoma and discriminating from other 16 common solid tumor cancers using plasma CF DNA or other body fluid CF DNA.

TABLE 28

| Melanoma_detect-spec | | | | | |
|---|---|---|---|---|---|
| cg00325866 | cg01228636 | cg04616691 | cg04824711 | cg05569109 | cg06019853 |
| cg08611163 | cg10830649 | cg12593303 | cg15307891 | cg18866529 | cg19530886 |
| cg19634213 | cg20146030 | cg21755725 | cg22280705 | cg24217704 | cg24678095 |
| cg26127345 | cg27084903 | | | | |

Subset for detect-spec:

cg15307891, cg18866529, cg27084903

In another aspect of the inventive subject matter, there is provided a kit and a process for detecting cancer, comprising means and reagents for detecting DNA methylation measurements of polygenic DNA methylation markers.

In one embodiment, a kit is provided for detecting hepatocellular carcinoma comprising means and reagents for DNA methylation measurements of the CG IDs of table 1 and 2.

In another embodiment, a kit is provided for detecting lung cancer comprising means and reagents for DNA methylation measurements of the CG IDs of table 3 and 4.

In another embodiment, a kit is provided for detecting prostate cancer comprising means and reagents for detecting DNA methylation measurements of the CG IDs of table 5.

In another embodiment, a kit is provided for detecting breast cancer comprising means and reagents for detecting DNA methylation measurements of the CG IDs of table 6 and 7.

In another embodiment, a kit is provided for detecting colorectal cancer comprising means and reagents for detecting DNA methylation measurements of the CG IDs of table 8.

In another embodiment, a kit is provided for detecting pancreatic cancer comprising means and reagents for detecting DNA methylation measurements of the CG IDs of table 9 and 10.

In yet another embodiment, a kit is provided for detecting brain cancer comprising means and reagents for detecting DNA methylation measurements of the CG IDs of table 11.

In another embodiment, a kit is provided for detecting gastric cancer comprising means and reagents for detecting DNA methylation measurements of the CG IDs of table 12 and 13.

In another embodiment, a kit is provided for detecting ovarian cancer comprising means and reagents for detecting DNA methylation measurements of the CG IDs of table 14 and 15.

In another embodiment, a kit is provided for detecting cervical cancer comprising means and reagents for detecting DNA methylation measurements of the CG IDs of table 16 and 17.

In another embodiment, a kit is provided for detecting head and neck squamous carcinoma (HNSC) comprising means and reagents for detecting DNA methylation measurements of the CG IDs of table 18 and 19.

In another embodiment, a kit is provided for detecting esophageal carcinoma comprising means and reagents for detecting DNA methylation measurements of the CG IDs of table 20 and 21.

In another embodiment, a kit is provided for detecting bladder cancer comprising means and reagents for detecting DNA methylation measurements of the CG IDs of table 22 and 23.

In another embodiment, a kit is provided for detecting renal cancer comprising means and reagents for detecting DNA methylation measurements of the CG IDs of table 24.

In another embodiment, a kit is provided for detecting testicular cancer comprising means and reagents for detecting DNA methylation measurements of the CG IDs of table 25

In other embodiments, a kit is provided for detecting one of 13 common cancers (bladder, brain, breast, cervical, colorectal, esophageal, HNSC, HCC (liver), lung, ovarian, pancreatic, prostate, stomach) comprising means and reagents for detecting DNA methylation measurements of the CG IDs of table 26.

In another embodiment, a kit is provided for detecting blood cancers such as AML and CLL comprising means and reagents for detecting DNA methylation measurements of the CG IDs detected by the BCD method that are specific for different subtypes of blood cancer Table 27

In another embodiment, a kit is provided for detecting melanoma comprising means and reagents for detecting DNA methylation measurements of the CG IDs of table 28.

In another embodiment, DNA pyrosequencing methylation assays are used for predicting HCC in body fluids such as plasma CF DNA by using CG IDs listed above, for example by using the below disclosed primers and standard conditions of pyrosequencing reactions:

```
cg02012576
Forward:
GGTAGTTAGGAAGTTTAGAGGTTGTAGTA
(SEQ ID NO: 3)

Reverse (biotinylated):
ACCACTACCCCAACCCAACCCTA
(SEQ ID NO: 1)

Sequence:
GGTTTTAGGATGTTTG
(SEQ ID NO: 2)

cg03768777 (VASH2)
Forward:
AGAATAATATTAGAGAATGGGATATGGAA
(SEQ ID NO: 4)

Reverse (biotinylated):
ACAACTCCAAAATCCTACCT
(SEQ ID NO: 5)

Sequence:
GAATGGGATATGGAATGA
(SEQ ID NO: 6)

cg05739190 (CCNJ)
Forward:
GTTTAGGAGTTGGGTTTTAGTTGAG
(SEQ ID NO: 7)

Reverse (biotinylated):
ACCCCACCCTAACTCCCTTACC
(SEQ ID NO: 8)

Sequence:
TGGGTTTTAGTTGAGG
(SEQ ID NO: 9)

cg24804544 (GRID2IP)
Forward(biotinylated):
GGGTAGGGGAGGGTTTTGAAATA
(SEQ ID NO: 10)

Reverse:
TAACCCCCCCTCCAACCTCATTC
(SEQ ID NO: 11)

Sequence:
CACCCAACTTCTCAAT
(SEQ ID NO: 12)
```

The specificity of the tissue of origin of the cancer is determined by measuring the DNA methylation of the following CGID cg02012576 (HPX)

```
Forward(biotinylated):
ATTTTTATGGGTATTAGTTTTAGGGAGAA
(SEQ ID NO: 13)

Reverse (biotinylated):
CCAAAACTATCCTATAACCTCTACAACTCA
(SEQ ID NO: 14)

Sequence:
ACCATTACCACCCCT
(SEQ ID NO: 15)
```

In another embodiment, a polygenic multiplexed amplicon bisulfite sequencing DNA methylation assay is used for predicting cancer in body fluids such as plasma CF DNA by using CG IDs listed above. For example, predicting prostate cancer using the below disclosed primers and standard conditions that involve bisulfite conversion, sequential amplification with target specific primers (PCR 1) followed by barcoding primers (PCR 2) and multiplexed sequencing in a single next generation MiSeq sequencer (Illumina), demultiplexing using Illumina software, data extraction and quantification of methylation using standard methods for methylation analysis such as Methylkit, followed by calculation of the weighted DNA methylation score and prediction of cancer from a small volume of body fluids such as plasma, saliva or urine.

The steps to detect prostate cancer the first PCR is performed as follows:

For CGID cg02879662

```
Forward primer:
5'ACACTCTTTCCCTACACgACgCTCTTCCgA

TCTNNNNNGGTAGGAGTTTTGGGAATTGG3'
(SEQ ID NO: 16)

Reverse primer:
5'gTgACTggAgTTCAgACgTgTgCTCT

TCCgATCTCCACCCCTACAATCCCTAA3'
(SEQ ID NO: 17)

For CGID cg16232979
Forward primer:
5'ACACTCTTTCCCTACACgACgCTCTTCCgAT

CTNNNNNYGGTTTYGGGTTTYGTATT3'
(SEQ ID NO: 18)

Reverse primer:
5'gTgACTggAgTTCAgACgTgTgCTCTTCCgA

TCTACRCAAAAATATAAATCRACRATC3'
(SEQ ID NO: 19)
```

To test that the cancer specifically originates in the prostate the first PCR is performed as follows:

```
For CGID: cg14041701 and cg14498227
Forward primer:
5'ACACTCTTTCCCTACACgACgCTCTTCCgATCTNNNNN

GTTTTGYGTTTYGGATTTGGGTT3' (SEQ ID NO: 20)

Reverse primer:
5'gTgACTggAgTTCAgACgTgTgCTCTTCCgATCTCATAAA

CAACACCTTTAAATAAACACTAAA3' (SEQ ID NO: 21)
```

To barcode the samples, use a second PCR reaction with the following primers:

```
Forward primer:
5'AATgATACggCgACCACCgAgATCT

ACACTCTTTCCCTACACgAC3' (SEQ ID NO: 22)

Barcoding primer (reverse):
5'CAAgCAgAAgACggCATACgAgATAGTCAT

CGgTgACTggAgTTCAgACgTg3' (SEQ ID NO: 23)

(red bases are the index; 200
variations of this index are used)
```

In other embodiments, Receiver operating characteristics (ROC) assays are used for detecting cancer by defining a threshold value between cancer and normal using weighted DNA methylation measurements of CG IDs. Samples above/below threshold will be classified as cancer. For example, CGIDs listed above for detecting HCC:

US 12,655,484 B2

23                                                    24

| cg02012576 | cg03768777 | cg05739190 | cg24804544. |

As used herein, the term "Hierarchical clustering" refers to a statistical method that builds a hierarchy of "clusters" based on how similar (close) or dissimilar (distant) are the clusters from each other as described for example in Kaufman, L.; Rousseeuw, P. J. (1990). Finding Groups in Data: An Introduction to Cluster Analysis (1 ed.). New York: John Wiley. ISBN 0-171-87876-6.

In another embodiment, hierarchical Clustering analysis assays are used for predicting cancer by using measurements of methylation of CG IDs listed above.

In another aspect of the inventive subject matter, methods for identifying DNA methylation markers for detecting cancer and other disease comprise the step of performing statistical analysis with the "binary-categorical differentiation (BCD)" method previously disclosed regarding DNA methylation measurements obtained from clinical samples.

In another embodiment, the method includes performing statistical analysis and the "binary-categorical differentiation (BCD)" method on DNA methylation measurements obtained from samples, with DNA methylation measurements obtained by performing Illumina Beadchip 450K or EPIC array of DNA extracted from at least one sample.

In another embodiment, the DNA methylation measurements are obtained by performing DNA pyrosequencing of DNA extracted from a sample followed by mass spectrometry based (Epityper™), PCR based methylation assays and targeted amplification of a region spanning the target CG IDs disclosed herein from bisulfite converted DNA followed by barcoding in a second set of amplification and indexed multiplexed sequencing on an Illumina next generation sequencer.

In other embodiments, the statistical analysis includes Receiver operating characteristics (ROC) assays.

In other embodiments, the statistical analysis includes hierarchical clustering analysis assays.

DEFINITIONS

As used herein, the term "CG" refers to a di-nucleotide sequence in DNA containing cytosine and guanosine bases. These di-nucleotide sequences could become methylated in human and other animals' DNA. The CG ID reveals its position in the human genome as defined by the Illumina 450K manifest (The annotation of the CGs listed herein is publicly available and installed as an R package IlluminaHumanMethylation450k.db IlluminaHumanMethylation450k.db: Illumina Human Methylation 450k annotation data. R package version 2.0.9.).

As used herein, the term "beta-value" refers to an estimation of methylation level at a CG ID position derived by normalization and quantification of Illumina 450K arrays using the ratio of intensities between methylated and unmethylated probes using the formula beta value=methylated C intensity/(methylated C intensity+unmethylated C intensity) between 0 and 1 with 0 being fully unmethylated and 1 being fully methylated.

As used herein, the term "penalized regression" refers to a statistical method aimed at identifying the smallest number of predictors required to predict an outcome out of a larger list of biomarkers as implemented for example in the R statistical package "penalized" as described in Goeman, J. J., LI penalized estimation in the Cox proportional hazards model. Biometrical Journal 52(1), 70-84.

As used herein, the term "clustering" refers to the grouping of a set of objects in such a way that objects in the same group (called a cluster) are more similar (in some sense or another) to each other than to those in other groups (clusters).

As used herein, the term "Receiver operating characteristics (ROC) assay" refers to a statistical method that creates a graphical plot that illustrates the performance of a predictor. The true positive rate of prediction is plotted against the false positive rate at various threshold settings for the predictor (i.e. different % of methylation) as described for example in Hanley, James A.; McNeil, Barbara J. (1982). "The Meaning and Use of the Area under a Receiver Operating Characteristic (ROC) Curve". Radiology 143 (1): 29-36.

As used herein, the term "multivariate or polygenic linear regression" refers to a statistical method that estimates the relationship between multiple "independent variables" or "predictors" such as percentage of methylation in CG IDs, and a "dependent variable" such as cancer. This method determines the "weight" or coefficient of each CG IDs in predicting the "outcome" (dependent variable such as cancer) when several "independent variables" such as CG IDs are included in the model.

Figure 8:
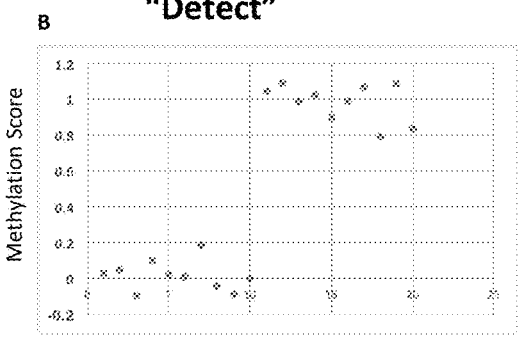
FIG. 8 is an illustration of a discovery of a polygenic DNA methylation marker for lung cancer. Illustration A of FIG. 8 is a table listing the source and number of patients whose methylation data was used for discovery of a set of CGIDs for detection of lung cancer disclosed in embodiments using the BCD method (Table 3) as well as CG IDs for determining the specific cancer tissue of origin (Table 4). Illustration B at the bottom left panel of FIG. 8 (Detect)
Figure 8:
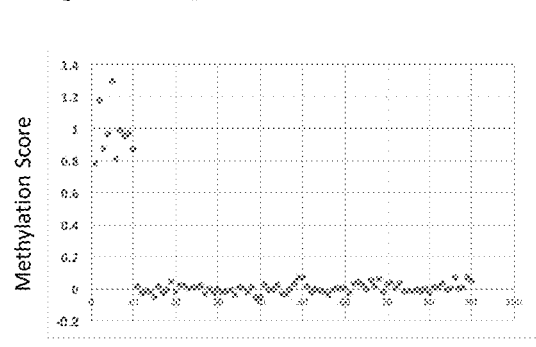

shows the combined methylation score for these CG IDs (Table 3) for each of the tested people listed from 1-20 (10 normal and 10 lung cancer). The polygenic score categorically differentiates between people with lung cancer and normal tissue. Illustration C at the bottom right panel of FIG. 8 shows the methylation score for the CGIDs (Table 4) detecting the specific tumor origin using data from people who have 8 different tumors (n=80). In these embodiments, the markers categorically differentiate between cancers from other origins and lung cancer.

Figure 9:
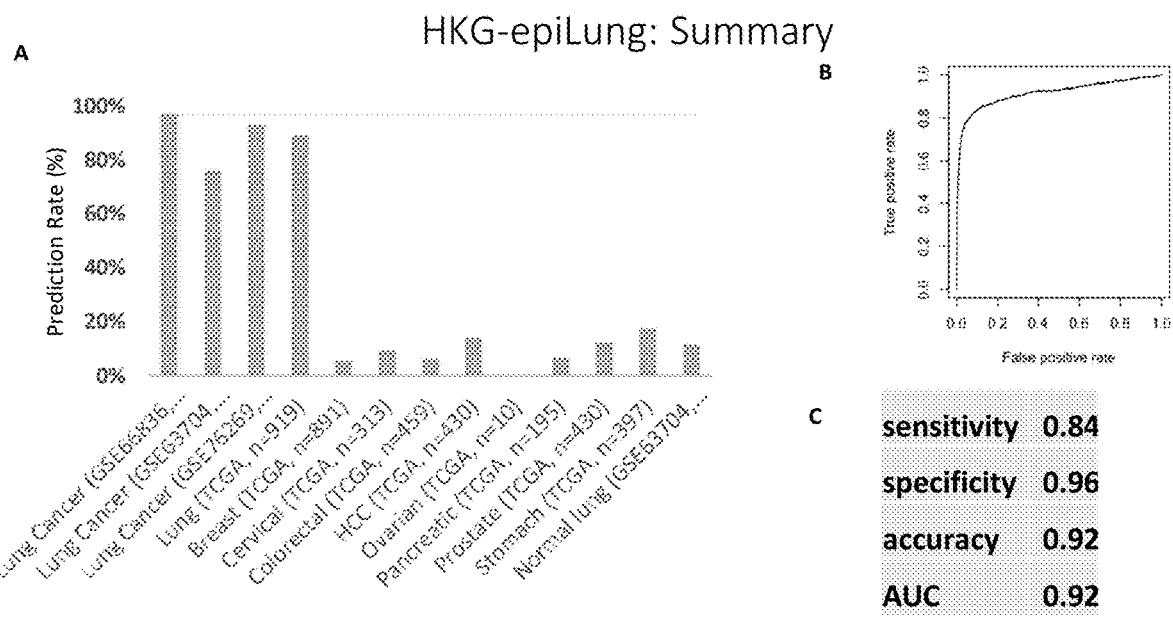

FIG. 9 is an illustration of the validation of the polygenic HKG-epiLung-detect and spec markers accuracy and specificity for HCC versus other cancers in TCGA methylation data (n=4166). Illustration A of FIG. 9 shows a detection rate of the HKG-epiLung detect/spec markers using DNA methylation data of patients with different cancers. Of note is the specificity for lung cancer. Illustration B of FIG. 9 shows a ROC plot of the HKG-Lung-detect markers specificity and sensitivity for lung cancer on 4166 patient DNA methylation data from TCGA. Illustration C of FIG. 9 shows a sensitivity and specificity to lung cancer versus cancers from other origins.

Figure 10:
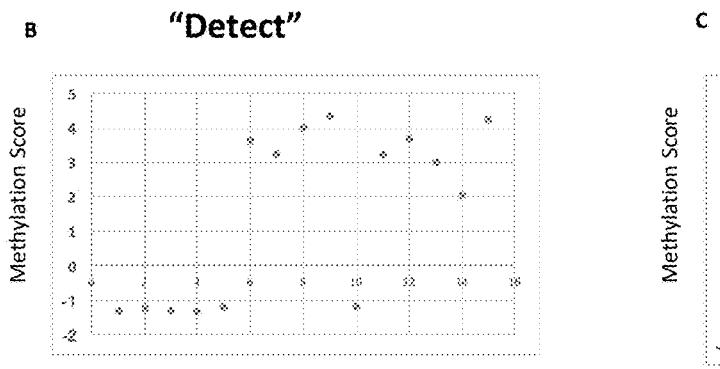
Figure 10:
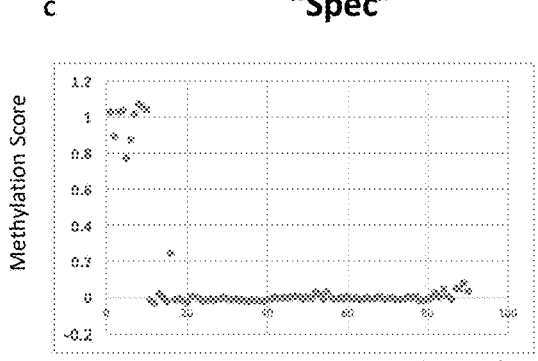

FIG. 10 is an illustration of the discovery of a polygenic DNA methylation marker for prostate cancer. Illustration A of FIG. 10 is a table listing the source and number of a patient whose methylation data was used for discovery of a set of CGIDs for detection of prostate cancer disclosed in embodiments using the BCD method (Table 5) and CGIDs for determining the specific cancer tissue of origin (Table 6). Illustration B at the bottom left panel of FIG. 10 (Detect) shows the combined methylation score for these CGIDs (Table 5) for each of the tested people listed from 1-15 (5 normal and 10 prostate cancer). The polygenic score categorically differentiates between people with prostate cancer and normal. Illustration C at the bottom right panel of FIG. 10 shows the methylation score for the CGs detecting the specific tumor tissue of origin (Table 6) using data from people who have 8 different tumors (n=80). In these embodiments, the markers categorically differentiate between cancers from other origins and prostate cancer.

Figure 11:
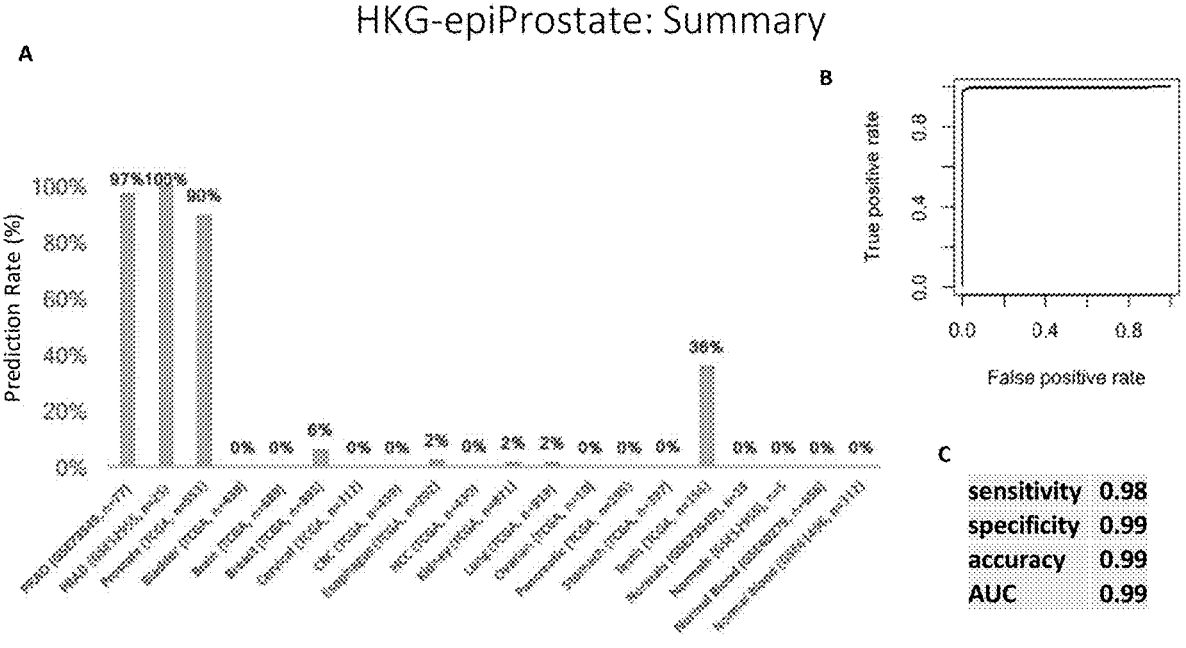

FIG. 11 is an illustration of a validation of the polygenic HKG-epiProstate-detect and spec markers accuracy and specificity for prostate versus other cancers in TCGA methylation data (n=4166). Illustration A of FIG. 11 shows the detection rate of the HKG-Prostate detect/spec markers using DNA methylation data from patients with different cancers. Of note is the specificity for prostate cancer. Illustration B of FIG. 11 is a ROC plot of the HKG-Prostate-detect markers specificity and sensitivity for lung cancer using DNA methylation data from 4166 patients in TCGA. Illustration C of FIG. 11 shows the sensitivity and specificity to prostate versus cancers from other origins.

Figure 12:
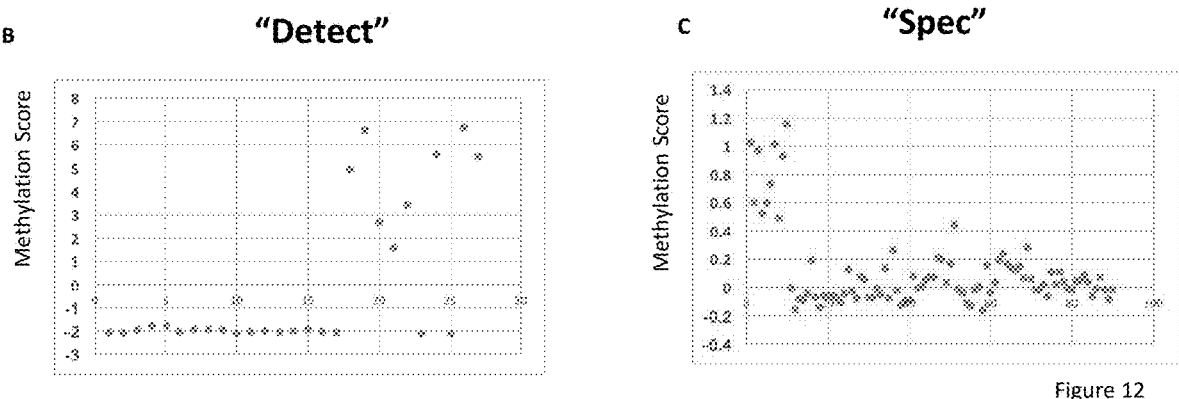

FIG. 12 is an illustration of a discovery of a polygenic DNA methylation marker for breast cancer. Illustration A of FIG. 12 is a table listing the source and number of patients whose methylation data was used for discovery of a set of CGs for detection of breast cancer disclosed in embodiments using the BCD method (Table 7) and CGIDs for determining the specific cancer of origin (Table 8). Illustration B at the bottom left panel of FIG. 12 (Detect) shows the combined methylation score for these CGIDs (Table 7) for each of the tested people listed from 1-27 (17 normal and 10 breast cancer). The polygenic score categorically differentiates between people with breast cancer and normal breast tissue. Illustration C at the bottom right panel of FIG. 12 shows the methylation score for the CGIDs detecting the specific origin of the tumor (Table 8) using data from people who have 8 different tumors (n=80). In these embodiments, the markers categorically differentiate between cancers from other origins and breast cancer.

Figure 13:
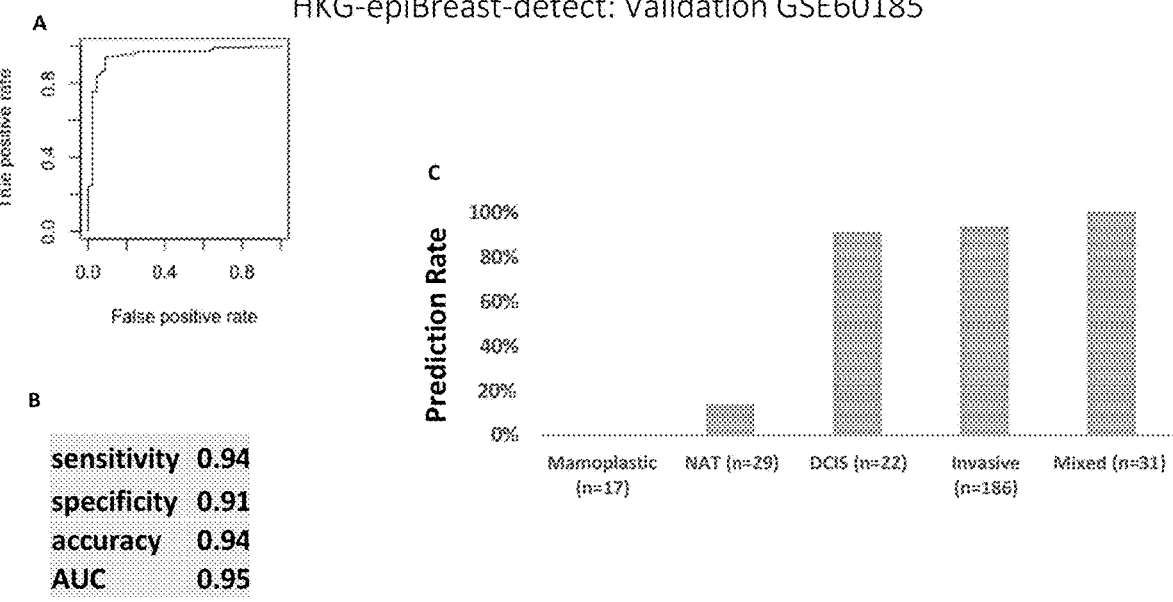

FIG. 13 is an illustration of a HKG-epiBreast-detect polygenic DNA methylation marker detect noninvasive as well as invasive breast cancer in validation cohort GSE60185 (n=285). Illustration A of FIG. 13 is a ROC plot showing area under the curve for the breast cancer polygenic DNA methylation marker using 239 breast cancer patient DNA methylation data, 17 mamoplastic surgery patients with no breast cancer and 29 adjacent tissues. The sensitivity, specificity and accuracy for all breast cancer are listed in B and the prediction rate of DCIS (ductal carcinoma in situ), invasive and mixed breast cancer samples are shown in Illustration C of FIG. 13. Of note is that the breast cancer markers detect even very early breast cancers (DCIS).

Figure 14:
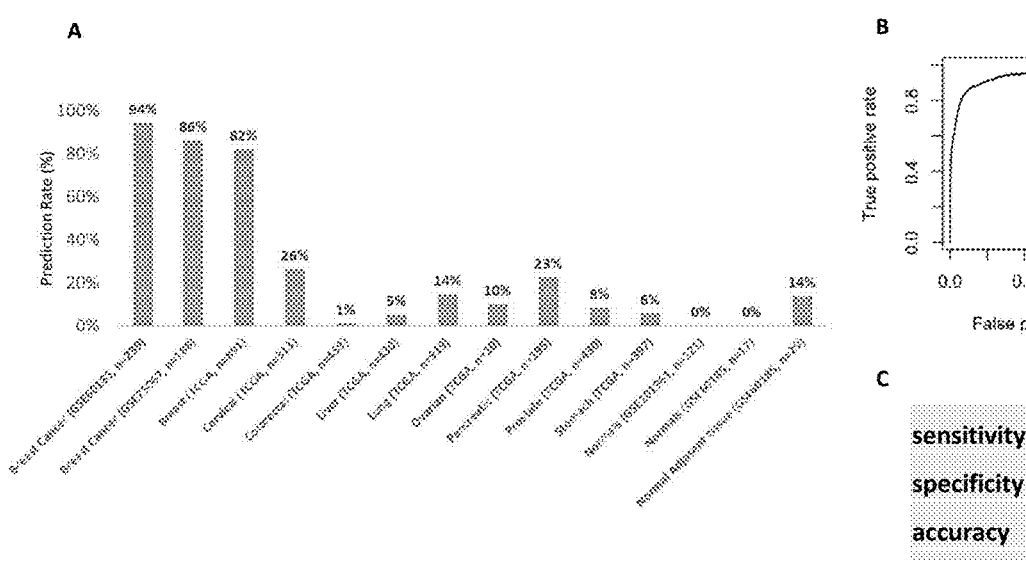
Figure 14:
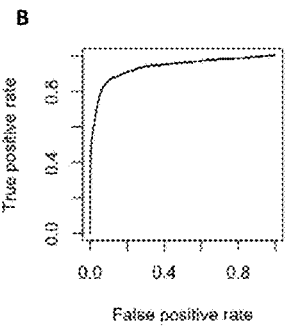

FIG. 14 is an illustration of a validation of the polygenic HKG-epiBreast-detect and spec markers accuracy and specificity for breast versus other cancers in TCGA methylation data (n=4166). Illustration A of FIG. 14 shows a detection rate of the HKG-epiBreast detect/spec markers in DNA methylation data from patients with different cancers. Of note is the specificity for breast cancer. Illustration B of FIG. 14 is a ROC plot of the HKG-Breast-detect markers specificity and sensitivity for detecting breast cancer using DNA methylation data from 4166 patients in TCGA. Illustration C of FIG. 14 shows the sensitivity and specificity to breast versus cancers from other origins.

Figure 15:
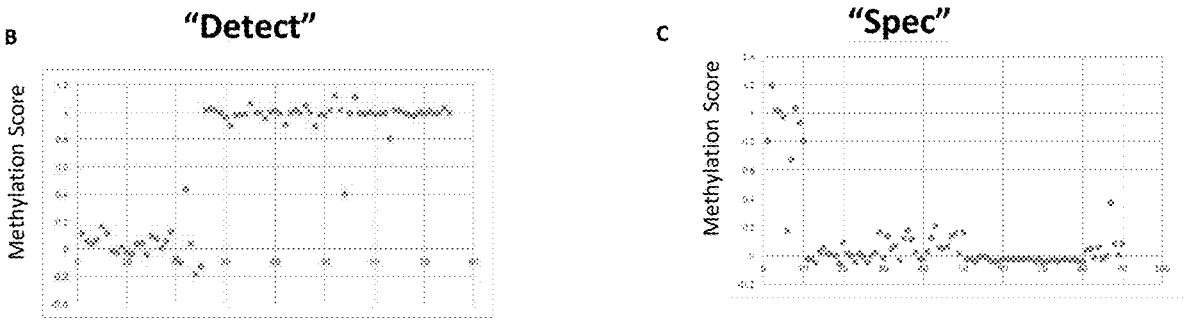

FIG. 15 is an illustration of a discovery of a polygenic DNA methylation marker for colorectal cancer (CRC). Illustration A of FIG. 15 is a table listing the source and number of patients whose methylation data was used for discovery of a set of CGIDs for detection of colorectal cancer disclosed in embodiments using the BCD method (Table 9) and CGIDs for determining the specific cancer of origin (Table 10). Illustration B at the bottom left panel of FIG. 15 (Detect) shows the combined methylation score for these CGIDs for each of the tested people listed from 1-75 (25 normal and 50 colorectal cancer). The polygenic score categorically differentiates between people with cancer and normal tissue. Illustration C at the bottom right panel of FIG. 15 shows the methylation score for the CGIDs detecting the specific origin of the tumor using DNA methylation data from people who have 8 different tumors (n=80). In these embodiments, the markers categorically differentiate between cancers from other origins and colorectal cancer.

Figure 16:
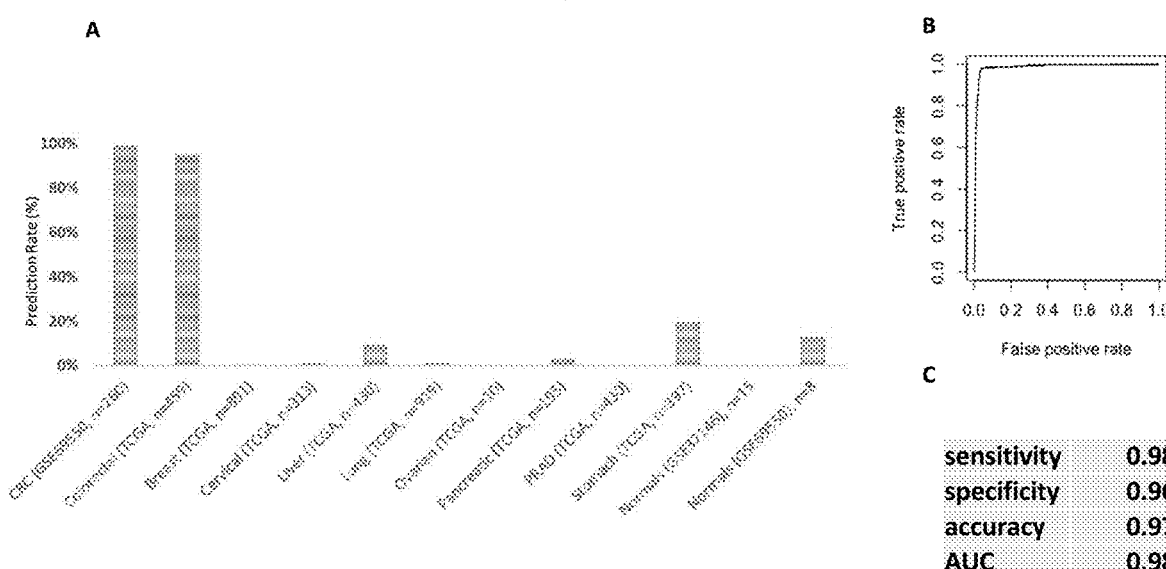

FIG. 16 is an illustration validation of the polygenic HKG-epiCRC-detect and spec markers accuracy and specificity for CRC versus other cancers using TCGA DNA methylation data set (n=4166). Illustration A of FIG. 16 is a detection rate of the HKGepiCRC detect/spec markers using DNA methylation data of patients with different cancers. Of note is the specificity for colorectal cancer. Illustration B of FIG. 16 is a ROC plot of the HKG-epiColon-detect markers specificity and sensitivity for colorectal cancer using DNA methylation data from 4166 patients in TCGA. Illustration C of FIG. 16 shows sensitivity and specificity to colorectal cancer versus cancers from other origins.

Figure 17:
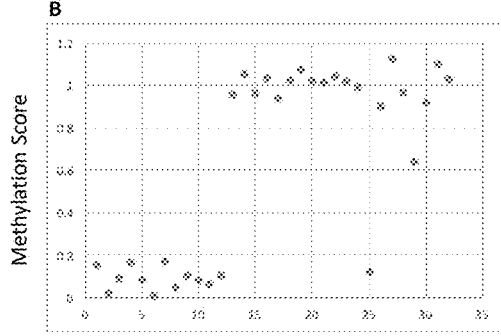
Figure 17:
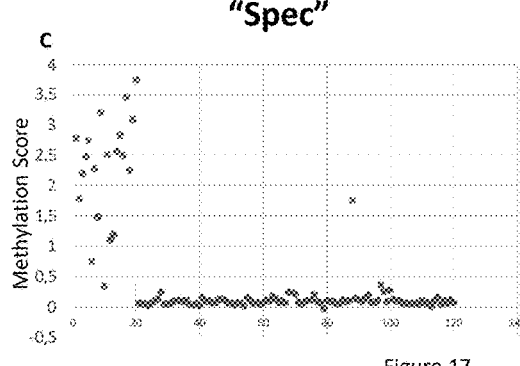

FIG. 17 illustrates a discovery of a polygenic DNA methylation marker for pancreatic cancer. Illustration A of FIG. 17 is a table listing the source and number of patients whose methylation data was used for discovery of a set of CGIDs for detection of pancreatic cancer disclosed in the present invention using the BCD method (Table 11) and CGIDs for determining the specific cancer of origin (Table 12). Illustration B at the bottom left panel of FIG. 17 (Detect) shows the combined methylation score for these CGIDs (Table 11) for each of the tested people listed from 1-32 (12 normal and 20 pancreatic cancer). The polygenic score categorically differentiates between people with pancreatic cancer and normal tissue. Illustration C at the bottom right panel of FIG. 17 shows the methylation score for the CGIDs detecting the specific origin of the tumor (Table 12) using data from people who have 10 different tumors (n=100). In these embodiments, the markers categorically differentiate between cancers from other origins and pancreatic cancer.

Figure 18:
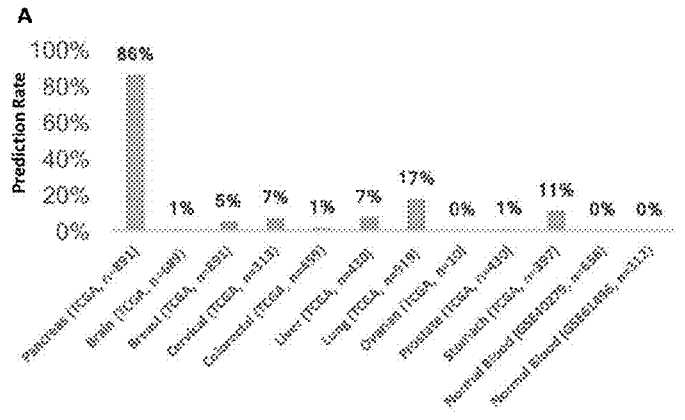
Figure 18:
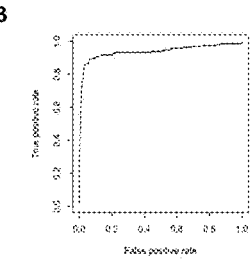

FIG. 18 is an illustration of a validation of the polygenic HKG-epiPancreas-detect and spec markers accuracy and specificity for pancreatic cancer versus other cancers in TCGA methylation data (n=4854). Illustration A of FIG. 18 is a detection rate of the HKG-epiPancreas detect/spec markers using DNA methylation data from patients with different cancers. Of note is the specificity for pancreatic cancer. Illustration B of FIG. 18 is a ROC plot of the HKG-epiPancreas-detect markers specificity and sensitivity for pancreatic cancer using DNA methylation data for 4854 patients in TCGA. Illustration C is the sensitivity and specificity to pancreatic cancer versus cancers from other origins.

Figure 19:
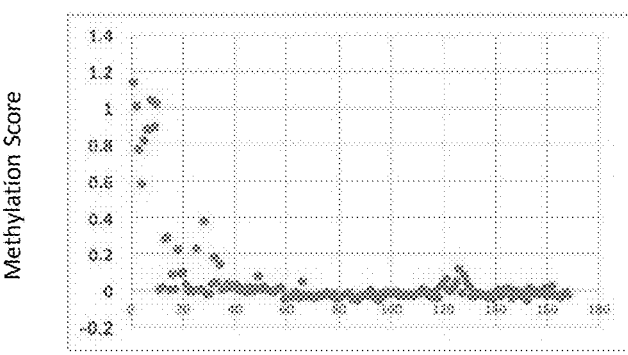

FIG. 19 is an illustration of a discovery of a polygenic DNA methylation marker for brain cancer (glioblastoma). Illustration A of FIG. 19 is a table listing the source and number of patient whose methylation data was used for discovery of a set of CGIDs for detection of brain cancer disclosed in the present invention using the BCD method (Table 13) and CGIDs for determining the specific origin of the cancer (Table 13). Illustration B at the bottom left panel (Detect/spec) shows the combined methylation score for these CGIDs (Table 13) for each of the tested people listed from 1-16 (6 normal and 10 brain cancer). The polygenic score categorically differentiates between people with brain cancer, 110 other cancers, normal tissues.

Figure 20:
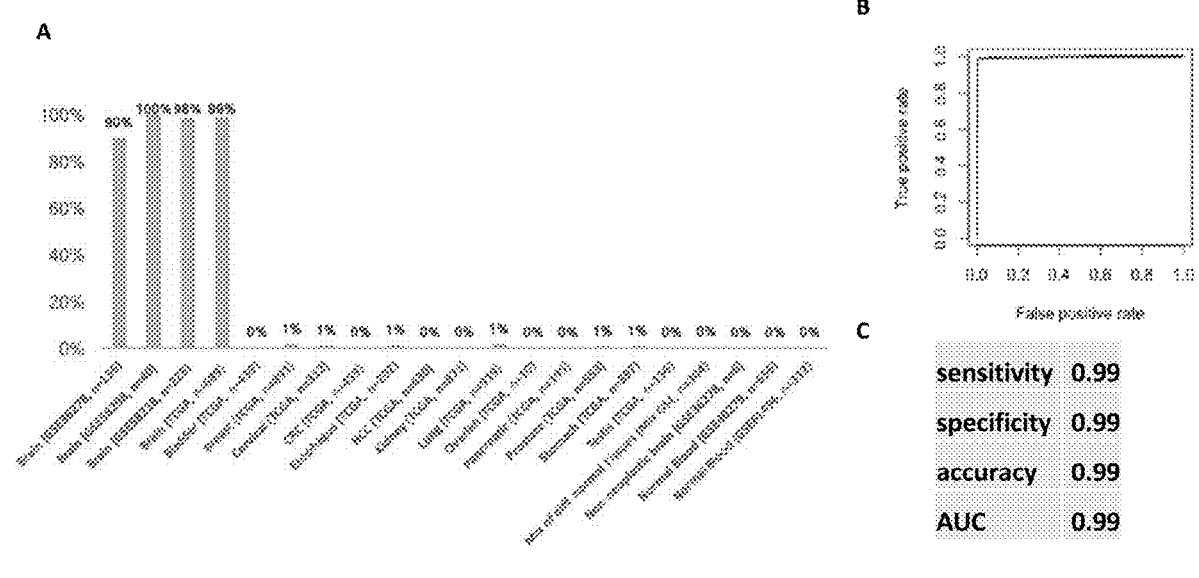

FIG. 20 is an illustration of a validation of the polygenic HKG-epiBrain-detect and spec markers accuracy and specificity for breast versus other cancers in TCGA methylation data (n=4854). Illustration A is a detection rate of the HKG-epiBrain detect/spec markers using DNA methylation data from patients with different cancers. Note the specificity for brain cancer. Illustration B is a ROC plot of the specificity and sensitivity of the HKGepiBrain-detect markers for brain cancer using DNA methylation data from 4854 patients in TCGA. Illustration C shows a sensitivity and specificity to brain cancer in TCGA data set (n=695).

Figure 21:
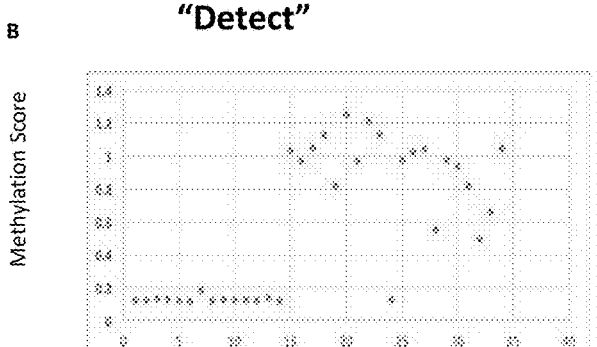
Figure 21:
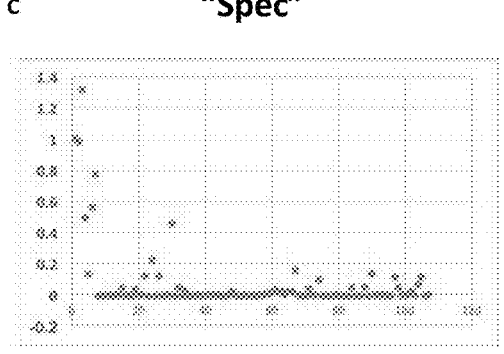

FIG. 21 is an illustration of a discovery of a polygenic DNA methylation marker for detection of gastric (stomach) cancer. Illustration A is a table listing the source and number of patients whose methylation data was used for discovery of a set of CGIDs for detection of gastric cancer disclosed in the present invention using the BCD method (Table 14) and CGIDs for determining the specific origin of the cancer (Table 15). Illustration B at the bottom left panel of FIG. 21 (Detect) shows the combined methylation score for these CGIDs (Table 14) for each of the tested people listed from 1-28 (14 normal and 20 gastric cancer). The polygenic score categorically differentiates between people with gastric cancer and normal tissue. Illustration C at the bottom right panel of FIG. 21 (Spec) shows the polygenic methylation scores for people who have 10 different tumors (n=100). In these embodiments, the markers categorically differentiate between cancers from other origins and gastric cancer.

Figure 22:
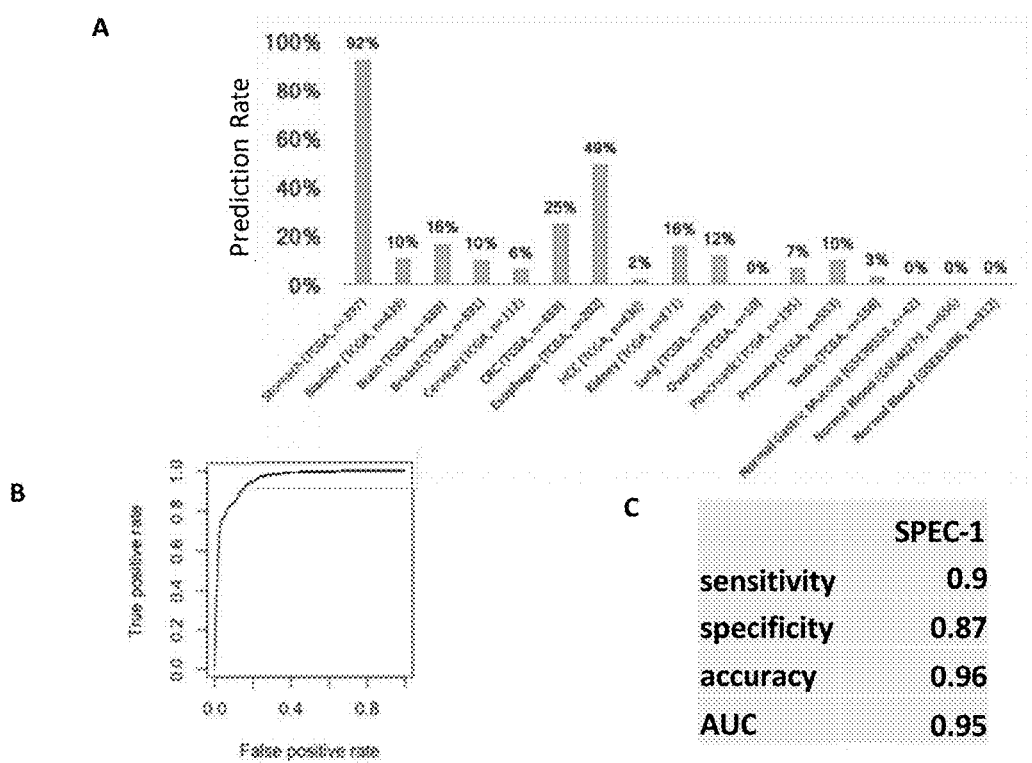

FIG. 22 is an illustration of a validation of the polygenic HKG-Stomach-detect and spec markers accuracy and specificity for gastric cancer versus other cancers in TCGA methylation data (n=4817). Illustration A is a detection rate of the HKG-epiStomach detect/spec markers using DNA methylation data from patients with different cancers. Of note is the specificity for gastric cancer. Illustration B is a ROC plot specificity and sensitivity of the HKG-epiStomach-detect spec 1 markers for stomach (gastric cancer) using DNA methylation data from 4420 patients in TCGA. Illustration C is a ROC plot of specificity and sensitivity the HKG-epiStomach-spec 1 markers for gastric cancer using DNA methylation data from 4854 patients in TCGA. Of note is that there is a significant cross reactivity with colorectal and esophageal cancer which attests to a shared origin.

Figure 23:
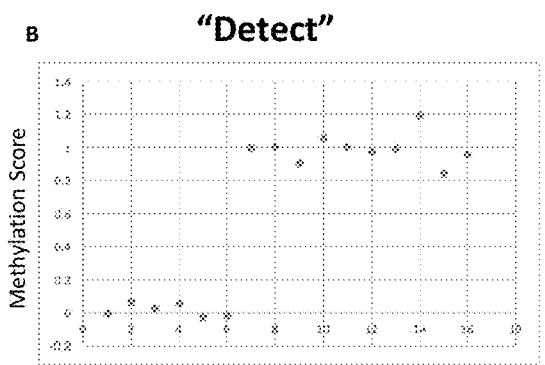
Figure 23:
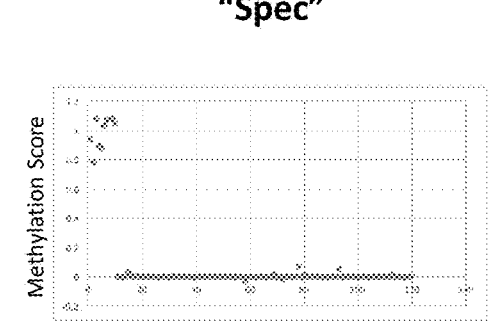

FIG. 23 is an illustration of a discovery of a polygenic DNA methylation marker for ovarian cancer. Illustration A is a table listing the source and number of patients whose methylation data was used for discovery of a set of CGIDs for detection of ovarian cancer disclosed in the present invention using the BCD method (Table 16) and CGIDs for determining the specific cancer of origin (Table 17). Illustration B at the bottom left panel of FIG. 23 (Detect) shows the combined methylation score for these CGIDs for each of the tested people listed from 1-15 (5 normal and 10 ovarian cancer). The polygenic score categorically differentiates between people with ovarian cancer and normal tissue. Illustration C at the bottom right panel of FIG. 23 shows the methylation score for the CGIDs detecting the specific tumor origin using data from people who have 11 different tumors (n=I10). In these embodiments, the markers categorically differentiate between cancers from other origins and ovarian cancer.

Figure 24:
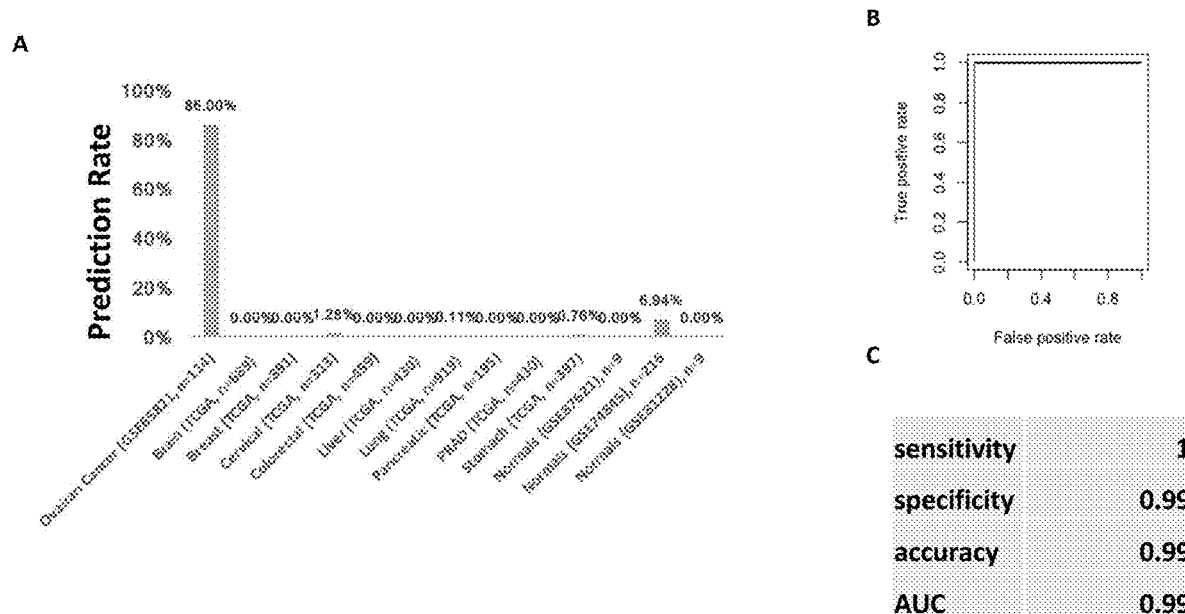

FIG. 24 is an illustration of a validation of the polygenic HKG-epiOvarian-detect and spec markers accuracy and specificity for cervical versus other cancers in TCGA methylation data (n=6522). Illustration A is a detection rate of the HKG-epiOvarian detect/spec markers using DNA methylation data from patients with different cancers. Note the specificity for ovarian cancer. Illustration B is a ROC plot specificity and sensitivity of the HKG-epiOvarian-detect and spec markers for ovarian cancer on DNA methylation data from 4723 patients in TCGA. Illustration C shows the sensitivity and specificity to ovarian cancer.

Figure 25:
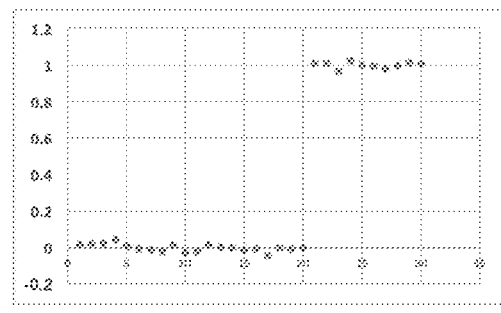
Figure 25:
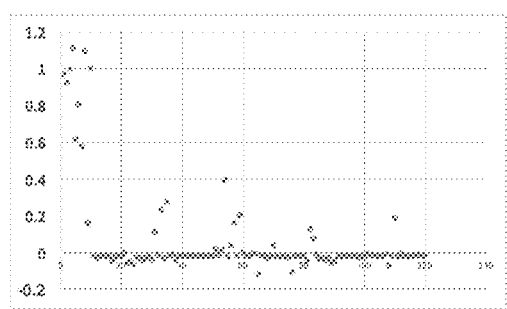

FIG. 25 is an illustration of a discovery of a polygenic DNA methylation marker for cervical cancer. Illustration A is a table listing the source and number of patients whose methylation data was used for discovery of a set of CGIDs for detection of cervical cancer disclosed in the present invention using the BCD method (Table 18) and CGs for determining the specific cancer of origin (Table 19). Illustration B at the bottom left panel of FIG. 25 (Detect) shows the combined methylation score for these CGIDs (Table 18) for each of the tested people listed from 1-30 (20 normal and 10 ovarian cancer). The polygenic score categorically differentiates between cervical cancer and normal tissue. Illustration C at the bottom right panel of FIG. 25 shows the methylation score for the CG IDs detecting the specific origin of the tumor (Table 19) using data from people who have 8 different tumors (n=80). In these embodiments, the markers categorically differentiate between cancers from other origins and cervical cancer, note however some measurable detection of colorectal cancer.

Figure 26:
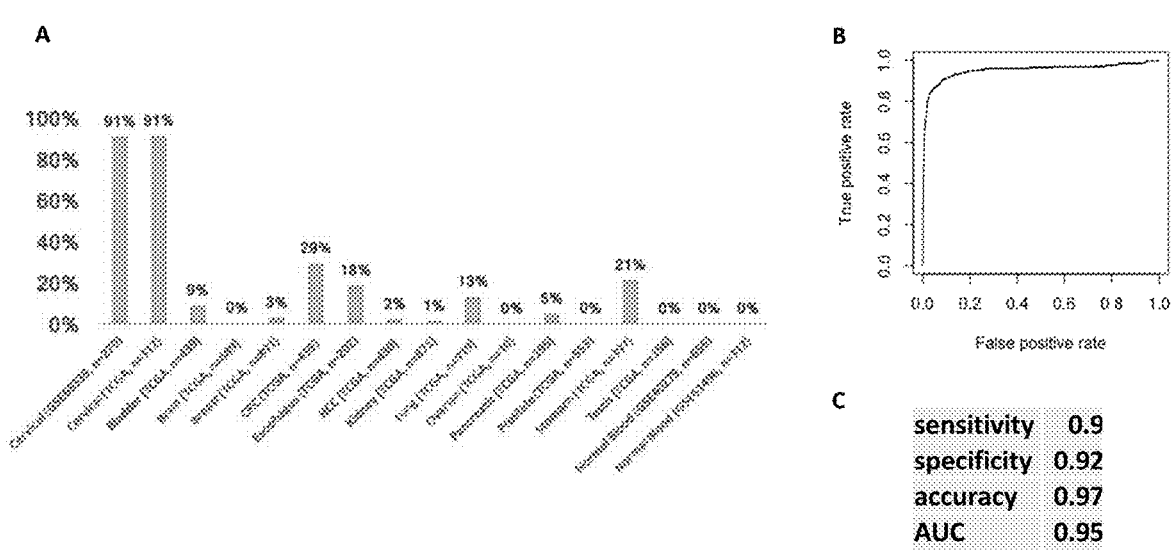

FIG. 26 is an illustration of a validation of the polygenic HKG-Cervix-detect and spec markers accuracy and specificity for cervix versus other cancers in TCGA methylation data (n=6522). Illustration A shows a detection rate of the HKG-Cervix detect/spec markers using DNA methylation data from patients with different cancers. Of note is the specificity for cervical cancer. Illustration B is a ROC plot of specificity and sensitivity of the HKG-Cervix-detect spec markers for cervical cancer using DNA methylation data from 4420 patients in TCGA. Illustration C shows a sensitivity and specificity to cervical cancer.

Figure 27:
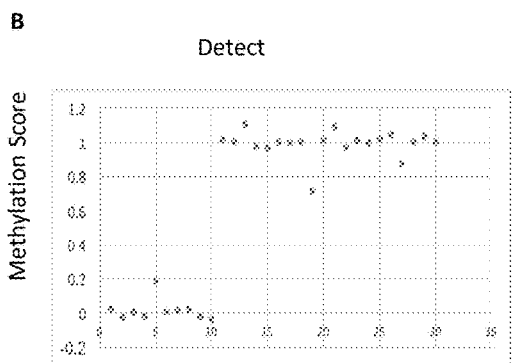
Figure 27:
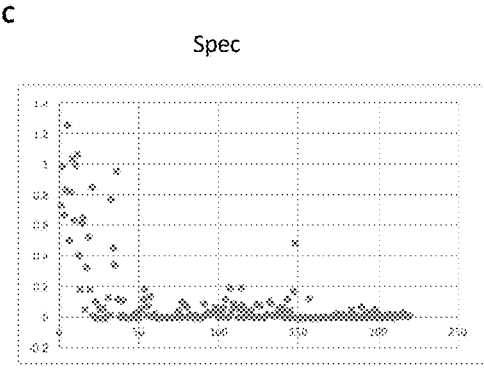

FIG. 27 is an illustration of a discovery of a polygenic DNA methylation marker for Head and Neck squamous cell Carcinoma (HNSC). Illustration A is a table listing the source and number of patients whose methylation data was used for discovery of a set of CG IDs for detection of HNSC disclosed in the present invention using the BCD method (Table 20) and CGs for determining the specific cancer of origin (Table 21). Illustration B at the bottom left panel of FIG. 27 shows the combined methylation score for these CG IDs (Table 20) for each of the tested people listed from 1-140 (10 cancer, 10 normal and 120 other cancers). Illustration C shows the polygenic score which categorically differentiates between HNSC and normal tissue samples in the embodiments as well as categorically differentiating between cancers from other origins and HNSC.

Figure 28:
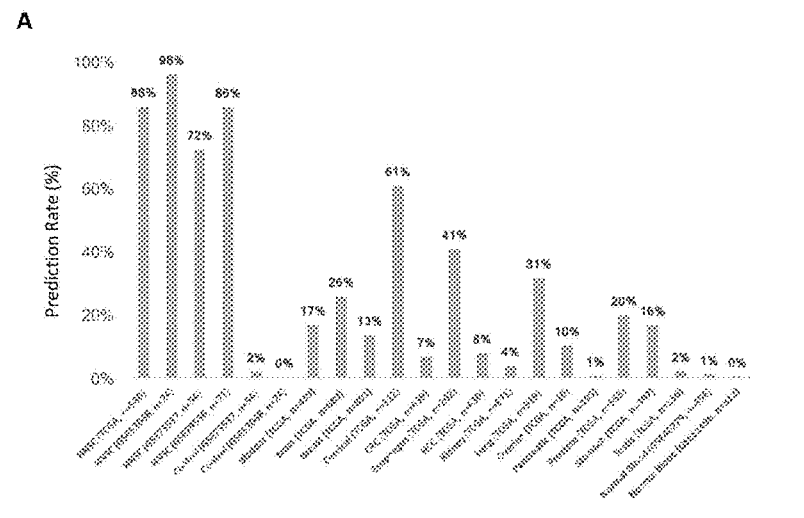
Figure 28:
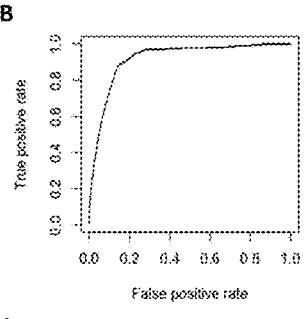

FIG. 28 is an illustration of a validation of the polygenic HKG-epiHNSC-detect/spec markers accuracy and specificity for HNSC versus other cancers in TCGA methylation data (n=4166). Illustration A is a detection rate of the HKG-epiHNSC detect/spec markers using DNA methylation data from patients with different cancers. Of note is the specificity for HNSC. Illustration B is a ROC plot of the specificity and sensitivity of HKG-epiHNSC-detect markers for HNSC on DNA methylation data from 4166 patients in TCGA. Illustration C shows the sensitivity and specificity for HNSC versus cancers from other origins.

Figure 29:
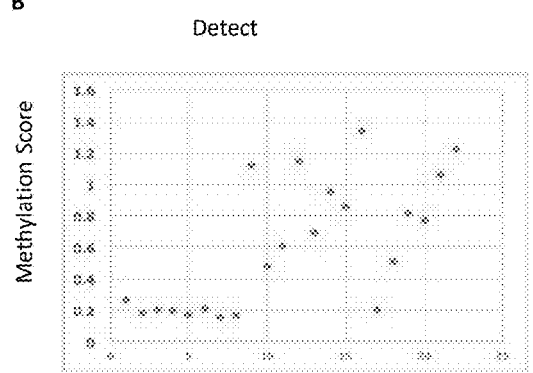
Figure 29:
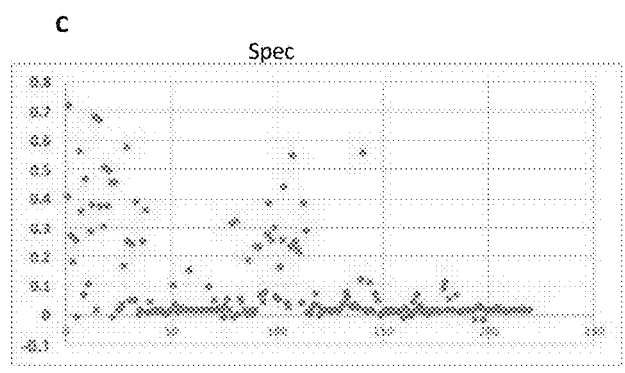

FIG. 29 is an illustration of a discovery of a polygenic DNA methylation marker for esophageal cancer. Illustration A is a table listing the source and number of patients whose methylation data was used for discovery of a set of CGIDs for detection of esophageal cancer disclosed in embodiments using the BCD method (Table 22) and CGIDs for determining the specific origin of the cancer (Table 23). Illustration B at the bottom left panel of FIG. 29 shows the combined methylation score for these CGIDs (Table 22) for each of the tested people listed from 1-15 (6 normal, 10 cancer). Illustration C shows the polygenic score categorically differentiating between esophageal cancer and normal tissue in the embodiments as well as categorically differentiating between cancers from other origins and esophageal cancer listed from 1-220 (20 cancer, 190 other cancer and 10 healthy blood).

Figure 30:
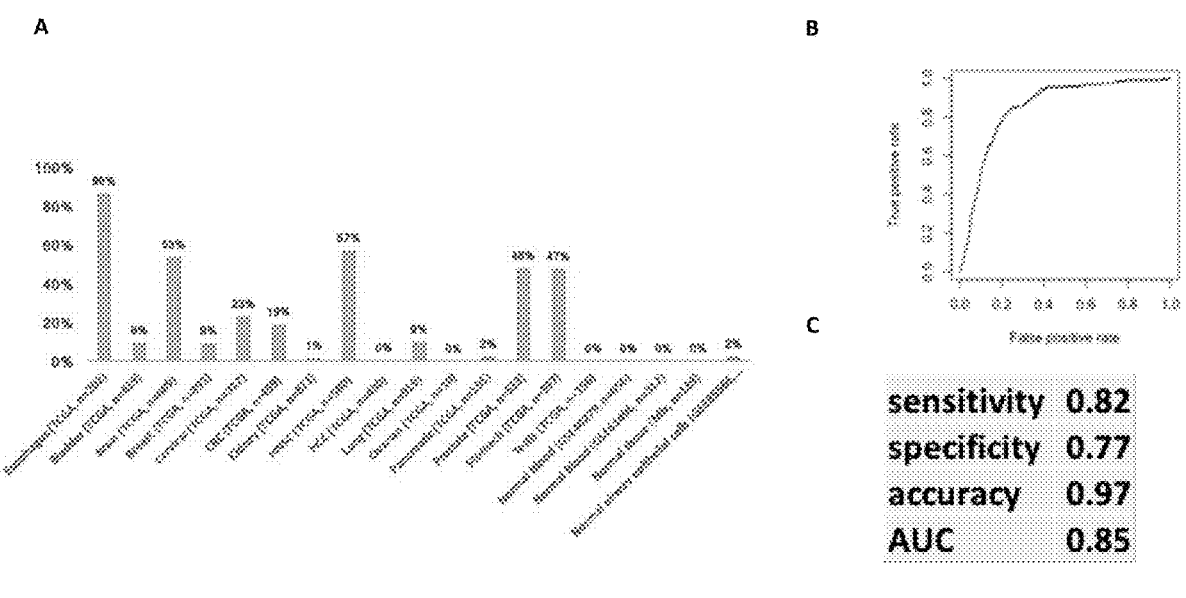

FIG. 30 is an illustration of a validation of the polygenic HKG-epiEsophageal—detect/spec markers accuracy and specificity for esophageal cancer versus other cancers in TCGA methylation data (n=7102). Illustration A shows a detection rate of the HKGepiEsophageal detect/spec markers using DNA methylation data from patients with different cancers. Of note is the specificity for esophageal cancer. Illustration B is a ROC plot of the specificity and sensitivity of the HKG-epiEsophageal-detect markers for HNSC on 4166 patient DNA methylation data in TCGA. Illustration C shows sensitivity and specificity to esophageal cancer versus cancers from other origins.

Figure 31:
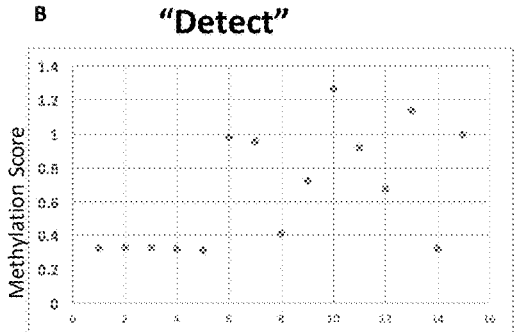
Figure 31:
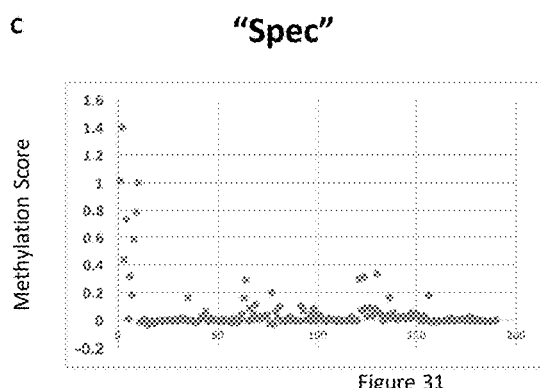

FIG. 31 is an illustration of a discovery of a polygenic DNA methylation marker for bladder cancer. Illustration A is a table listing the source and number of patients whose methylation data was used for discovery of a set of CGIDs for detection of bladder cancer disclosed in embodiments using the BCD method (Table 24) and CGIDs for determining the specific origin of the cancer (Table 25). Illustration B at the bottom left panel of FIG. 31 (Detect) shows the combined methylation score for these CGIDs (Table 24) for each of the tested people listed from 1-15 (5 normal and 10 bladder cancer). Illustration C at the bottom right panel of FIG. 31 shows the methylation score for the CGIDs (Table 25) detecting the specific origin of the tumor using data from people who have 13 different tumors (n=130). In these embodiments, the markers differentiate between cancers from other origins and bladder cancer. Also of note are some measurable detection of colorectal cancer with these markers.

Figure 32:
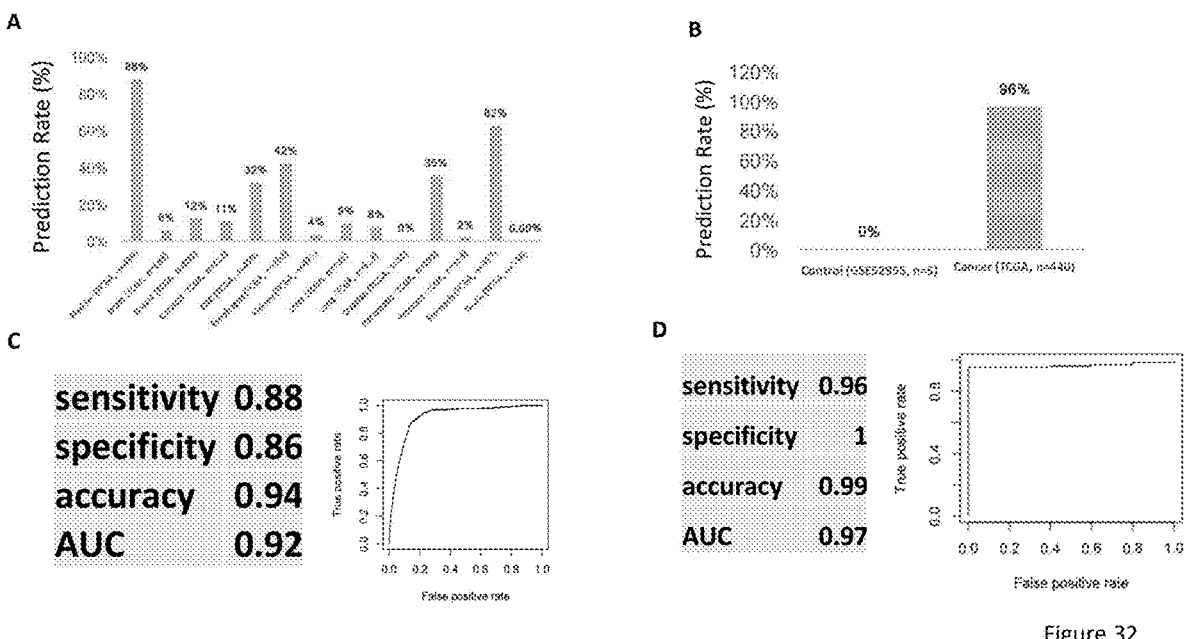

FIG. 32 is an illustration of a validation of accuracy and specificity of the polygenic HKG-epiBladder-detect and spec markers for bladder cancer versus other cancers in TCGA (n=4723). Illustration A shows a detection rate of the HKG-epiBladder spec (A) and detect markers (B) on DNA methylation data of patients with different cancers (A) and bladder cancer (B). Illustration C is a ROC plot of the specificity and sensitivity of HKG-epiBladder spec markers for bladder cancer using DNA methylation data from 4420 patients in TCGA. Illustration D is a ROC plot of the specificity and sensitivity of the HKG-epiBladder detect markers for bladder cancer (n=440).

Figure 33:
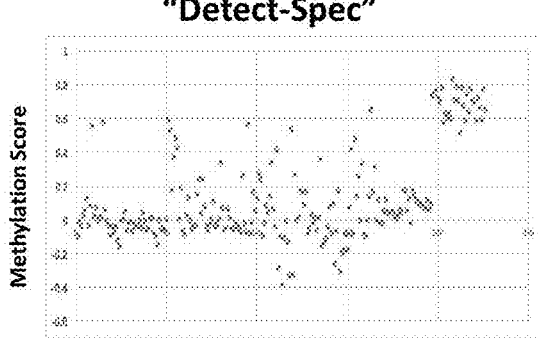

FIG. 33 is an illustration of a discovery of a polygenic DNA methylation marker for kidney cancer. Illustration A is a table listing the source and number of patients whose methylation data was used for discovery of a set of CGIDs for detection of kidney cancer disclosed in embodiments using the BCD (hypo) method and for determining the specific origin of the cancer (Table 26). Illustration B at the bottom left panel of FIG. 33 (Detect/spec) shows the combined methylation score for these CGIDs (Table 26) for each of the tested people listed from 1-226 (180 other cancers, 10 healthy blood, 6 normal kidney, 30 renal cancer). In these embodiments, the polygenic score categorically differentiates between kidney cancer, other cancers and normal blood.

Figure 34:
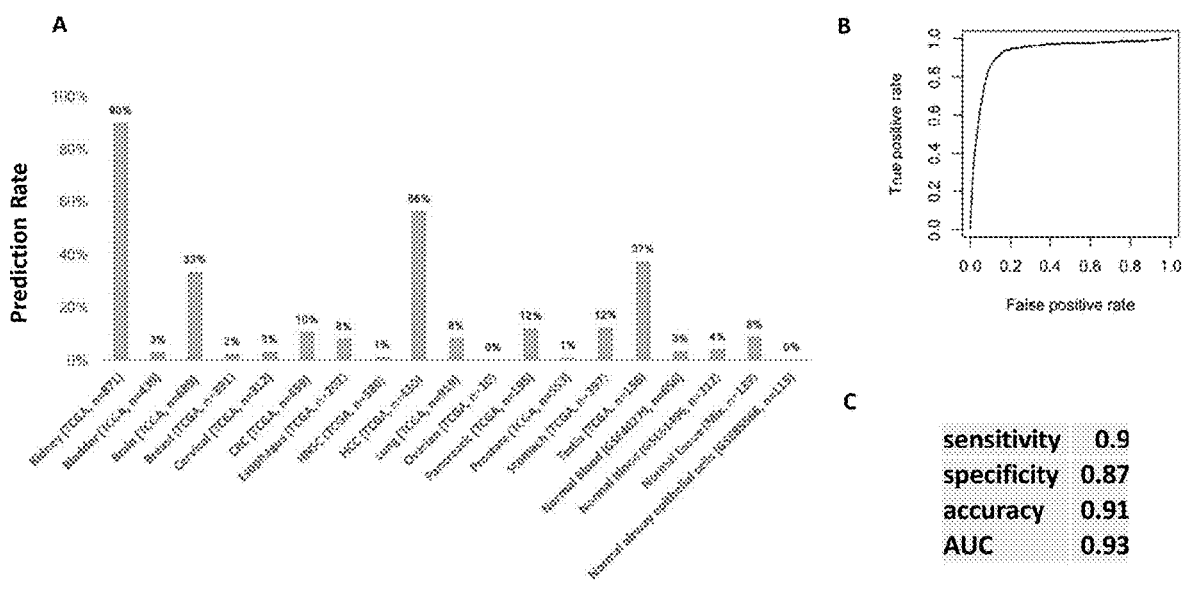

FIG. 34 is an illustration of a validation of the accuracy and specificity of polygenic HKG-epiKidney-detect and spec markers for kidney cancer versus other cancers and normal tissues using TCGA DNA methylation data (n=7102). Illustration A is the detection rate of the HKG-epiKidney detect/spec markers using DNA methylation data from different cancers. Of note is the specificity for kidney cancer. Illustration B is a ROC plot of the specificity and sensitivity of HKG-Cervix-detect spec markers for renal cancer using DNA methylation data from 6367 cancers in TCGA. Illustration C is a sensitivity and specificity to renal (kidney) cancer. Of additional note is a crossover with brain, HCC and testicular cancer.

Figure 35:
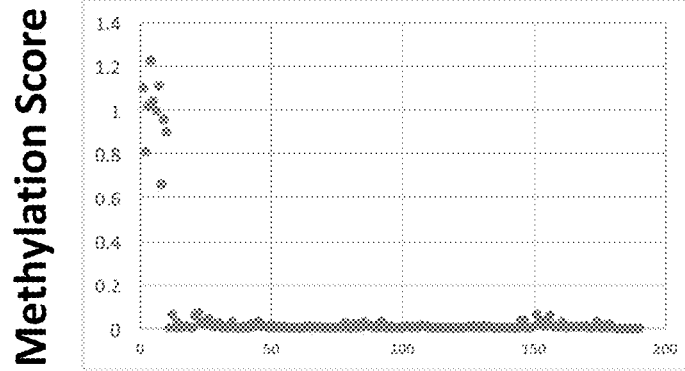

FIG. 35 is an illustration of a discovery of a polygenic DNA methylation marker for testicular cancer. Illustration A is a table listing the source and number of patients whose methylation data was used for discovery of a set of CGIDs for detection of testicular cancer disclosed in embodiments using the BCD (hypo) method and for determining the specific cancer of origin (Table 27). Illustration B at the bottom left panel of FIG. 35 (Detect/spec) shows the combined methylation score for these CG IDs (Table 27) for each of the tested people listed from 1-226 (10 testicular cancer, 180 other cancers, 10 normal blood). In these embodiments, the polygenic score categorically differentiates between testicular cancer and normal blood and other cancers.

Figure 36:
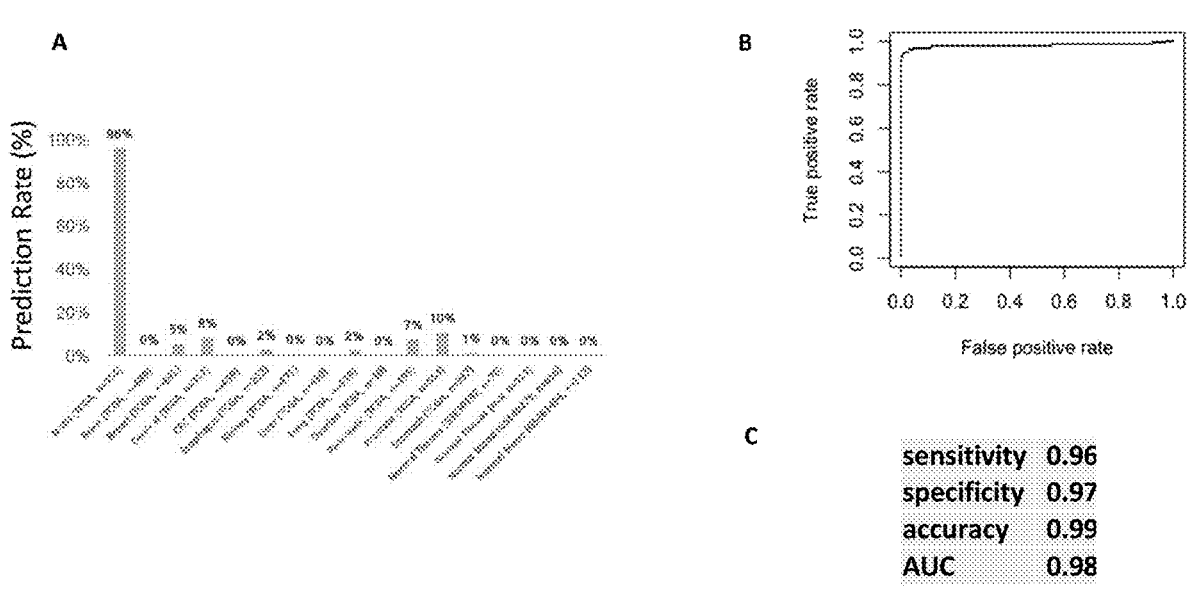

FIG. 36 is an illustration of a validation of the accuracy and specificity of the polygenic HKG-epiTestis-detect and spec markers for testicular cancer versus other normal tissues and cancers in TCGA methylation data (n=7102). Illustration A shows the detection rate of the HKG-epiTesstis detect/spec markers using DNA methylation data from patients with different cancers. Of note is the specificity for Testis cancer. Illustration B is a ROC plot of the specificity and sensitivity of HKG-epiTestis-detect spec markers for testicular cancer using DNA methylation data from 6367 patients in TCGA. Illustration C is the sensitivity and specificity to testicular cancer.

Figure 37:
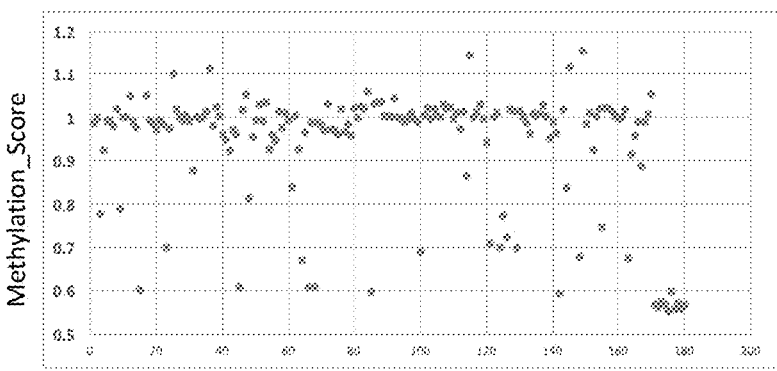

FIG. 37 is an illustration of a discovery of a Pan cancer polygenic DNA methylation marker for 13 common cancers. Illustration A is a table listing the source and number of patients whose methylation data was used for discovery of a set of CGIDs for detection of 13 common cancers (Table 28) (bladder cancer, brain cancer, breast cancer, cervical cancer, colorectal cancer CRC, esophageal cancer, liver cancer, lung cancer, ovarian cancer, pancreatic cancer, prostate cancer, and stomach cancer) disclosed in embodiments using the BCD method (Table 28). Illustration B shows the combined methylation score for these CGIDs for each of the tested people listed from 1-310 (180 cancer and 10 normal). In these embodiments, the polygenic score differentiates between cancers and normal tissue.

Figure 38:
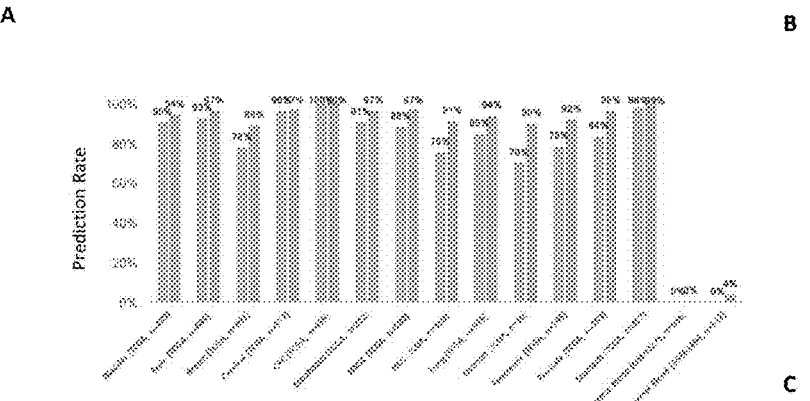
Figure 38:
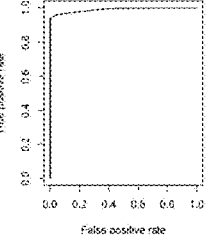

FIG. 38 is an illustration of a validation of the polygenic HKG epiPancancer markers accuracy and specificity in TCGA methylation data (n=7102). Illustration A shows Methylation scores calculated using the epiPancancer polygenic DNA methylation markers in patients with 13 different cancers using TGCA data. Illustration B is a ROC plot of the specificity and sensitivity of HKG-epiPancancer detect and spec markers using DNA methylation data from for all cancers from 4878 patients in TCGA. Illustration C is a ROC plot of the epiPancancer polygenic markers describing specificity and sensitivity for detection of 13 common cancers. Illustration D shows the overall sensitivity and specificity of the pan cancer markers for detecting cancer. In these embodiments, one or more colors are used, for example orange (weighted methylation score) and blue (detection of one BCD marker per sample is scored as a positive cancer).

Figure 39:
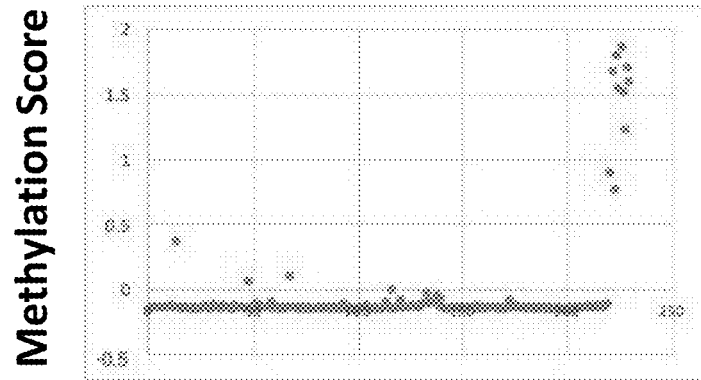

FIG. 39 is an illustration of a discovery of polygenic DNA methylation marker for Melanoma. Illustration A is a table listing the source and number of patients whose methylation data was used for discovery of a set of CGIDs for detection of melanoma (Table 45) disclosed in embodiments using the BCD method (Table 45). Illustration B is the combined methylation score for these CGIDs for each of the tested people listed from 1-220 (other cancers and normal blood) and 10 patients with melanoma. In these embodiments, the polygenic score differentiates between melanoma, other cancers and normal tissue.

Figure 40:
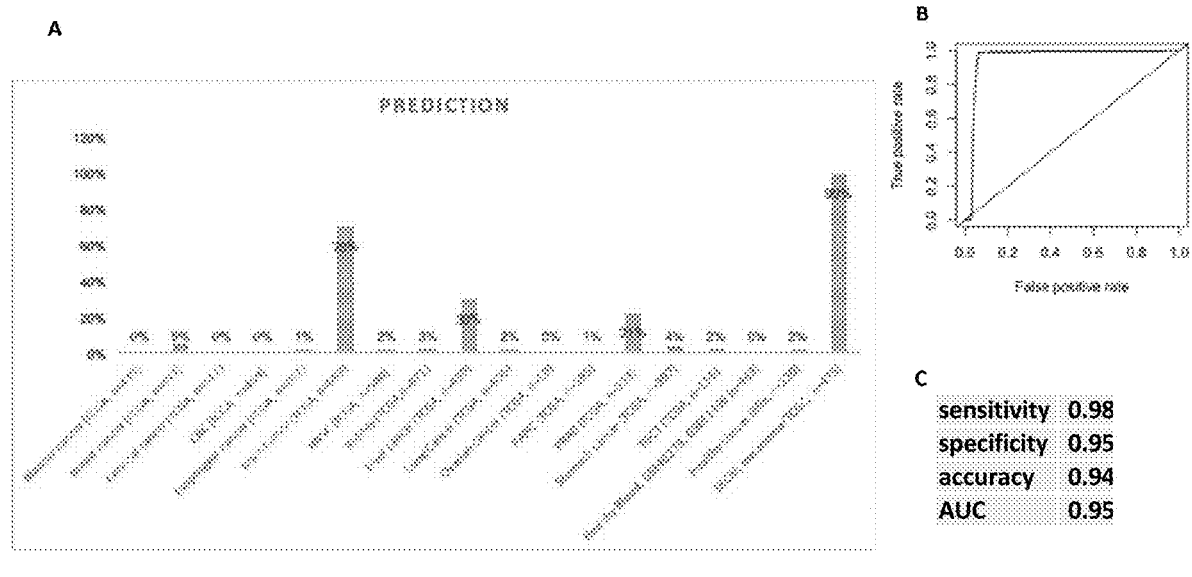

FIG. 40 is an illustration of a validation of the accuracy and specificity of the polygenic HKG-epiMelanoma-detect and spec markers for melanoma versus other normal tissues and cancers in TCGA methylation data (n=7102). Illustration A shows the detection rate of the HKG-epiMelanoma detect/spec markers using DNA methylation data from patients with different cancers. Of note is the specificity for melanoma (with overlapping detection of liver cancer brain and cancer and prostate cancer). Illustration B is a ROC plot of the specificity and sensitivity of HKG-Melanoma-detect spec markers for melanoma using DNA methylation data from 6367 patients in TCGA. Illustration C shows the sensitivity and specificity to melanoma.

FIG. 41 is an illustration of a discovery of polygenic DNA methylation marker for blood cancers (Acute Myeloid Leukemia (AML). Illustration A is a table listing the source and number of patients whose methylation data was used for discovery of a set of CGIDs for detection of blood cancer AML (Table 46) disclosed embodiments using the BCD method (Table 46). Illustration B is the combined methylation score for these CGIDs for each of the tested people listed from 1-10 (normal blood) and 10 patients with AML. In these embodiments, the polygenic score differentiates between AML and normal blood.

Figure 42:
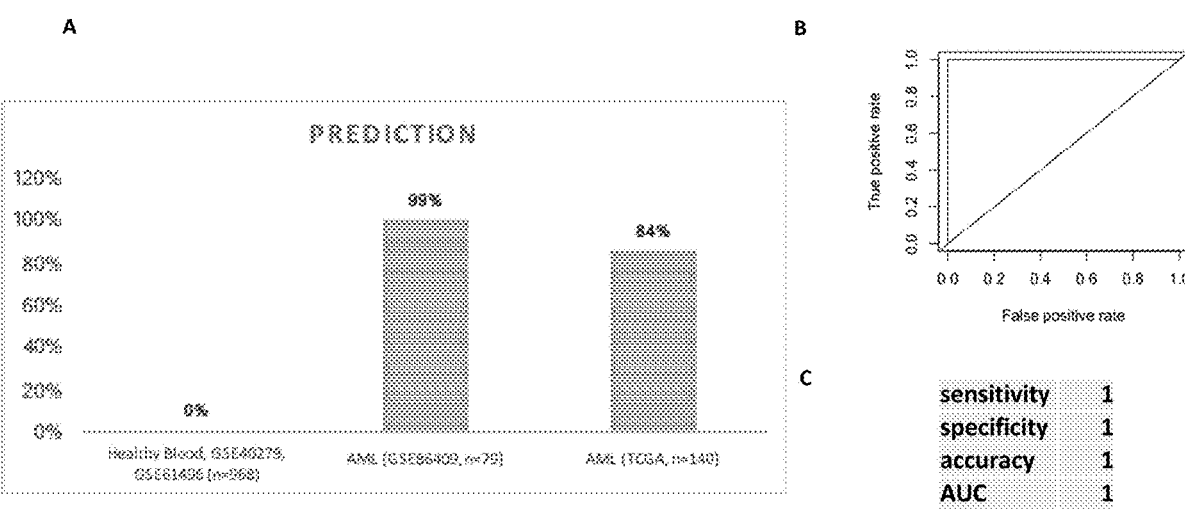

FIG. 42 is an illustration of a validation of the accuracy and specificity of the polygenic HKG-epiAML-detect and spec markers for AML in GSE86409 (n=79) and in TCGA (n-140) versus normal blood in GSE40279 and GSE61496 (n=968). Illustration A shows a detection rate of the HKG-epiAML detect/spec markers using DNA methylation data from patients with AML and healthy blood. Of note is the specificity for melanoma (with overlapping detection of liver cancer brain and cancer and prostate cancer). Illustration B is a ROC plot of the specificity and sensitivity of HKG-AML-detect spec markers for AML using DNA methylation data from GSE86409 (n=79), TCGA (n-140) GSE40279 and GSE61496 (n=968). Illustration C shows the sensitivity and specificity to AML.

Figure 43:
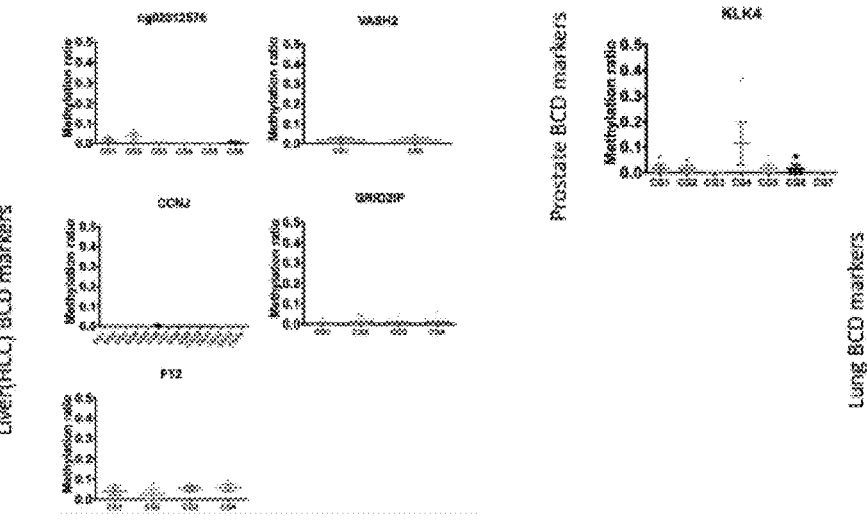
Figure 43:
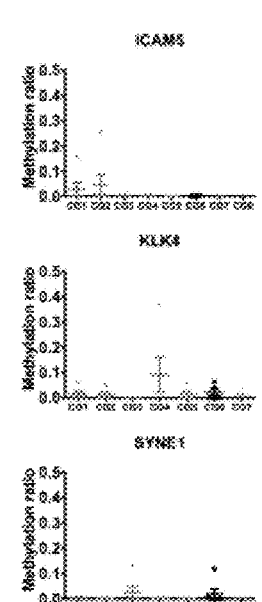

FIG. 43 is an illustration of a validation that the primers selected for detecting different cancers exhibit BCD properties ~0 methylation in plasma derived from normal people (each sample is a mixture of plasma from normal patients). The first PCR1 reaction targeting the specific CGs was performed using sequence targeted primers. Following a second PCR, the amplified fragments were purified and subjected to next generation sequencing. DNA methylation was quantified in each of the indicated CG ID positions.

Figure 44:
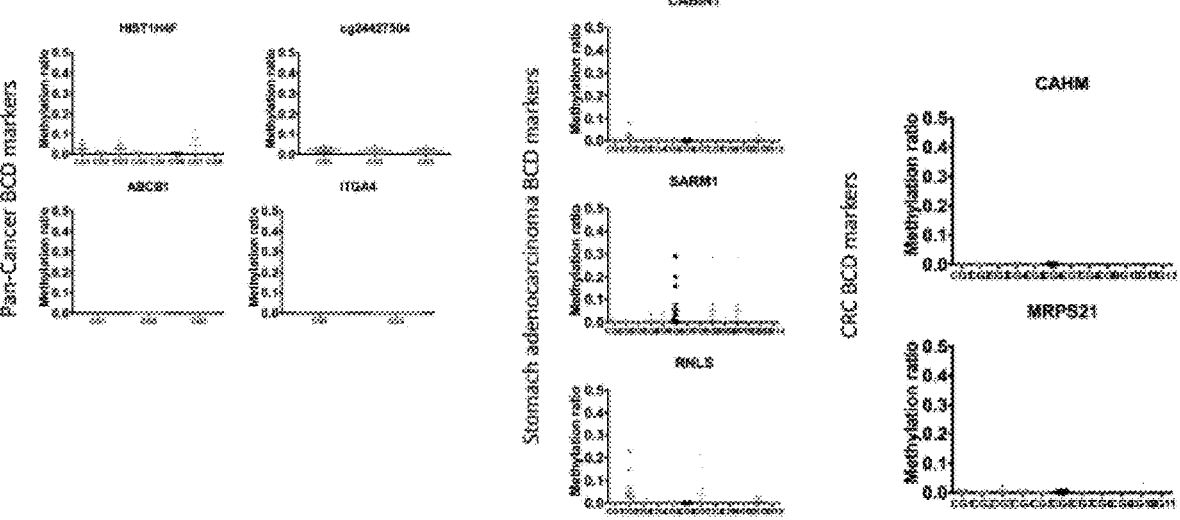

FIG. 44 is an illustration of a validation that the indicated primers selected for detecting different cancers exhibit BCD properties ~0 methylation in plasma derived from normal people (each sample is a mixture of plasma from normal patients).

Figure 45:
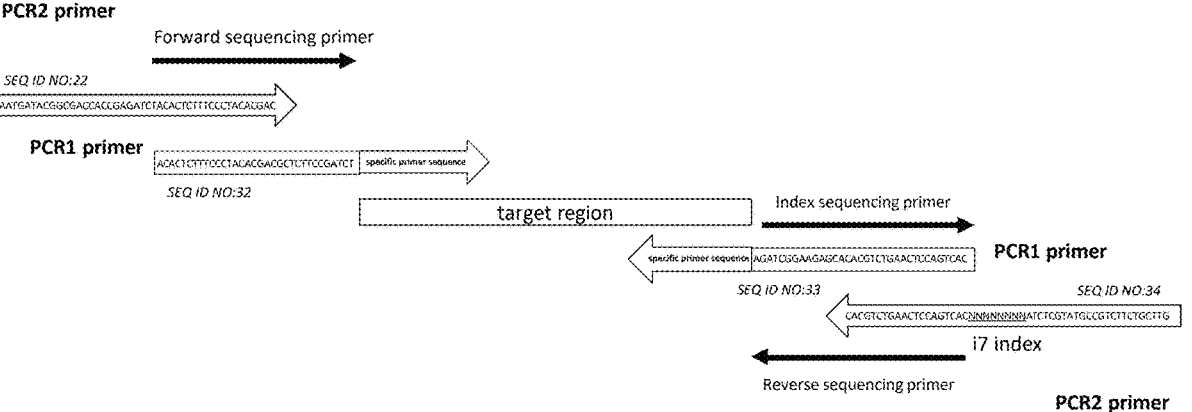

FIG. 45 is an illustration of a primer design for multiplex amplification and sequencing. The first PCR reaction targets the specific regions of interest, note PCR1 primer has complementary sequence to second PCR2 primers. The second set of primers introduces the index for each patient as well as the reverse and forward sequencing primers.

Figure 46:
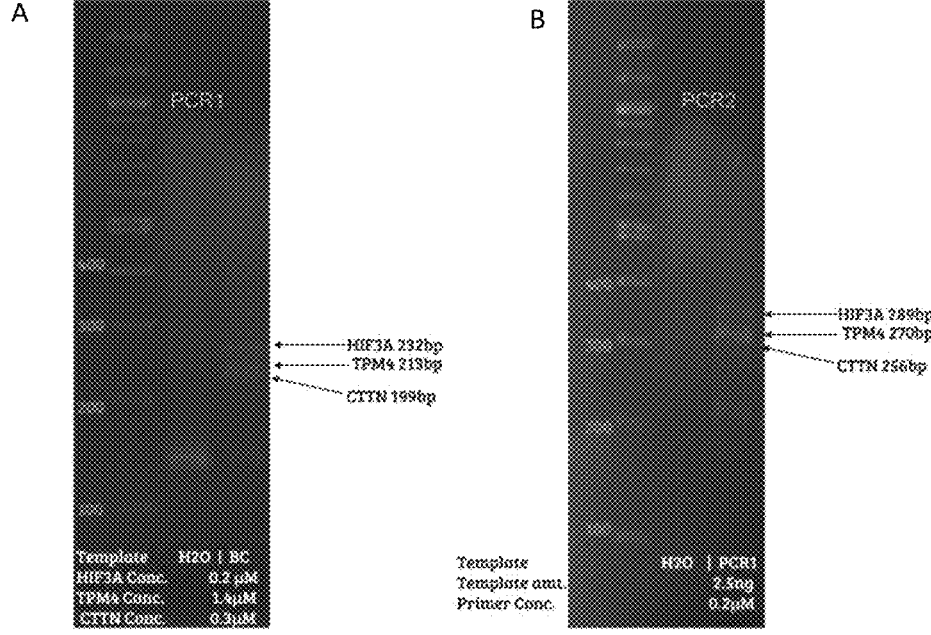

FIG. 46 is an illustration of an optimization of PCR conditions for detecting prostate cancer. A multiplex PCR1 reaction using varying primer concentrations as indicated DNA for the three markers of prostate cancer HIF3A 232 bp, TPM4 213 bp, and CTTN 199 bp is shown on the right panel.

Figure 47:
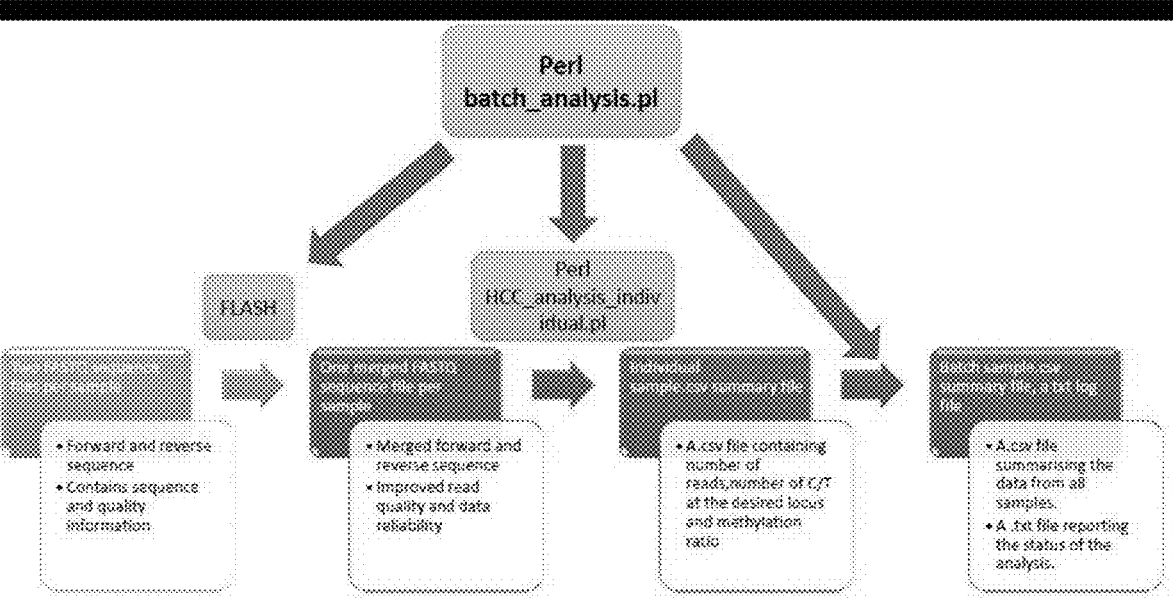

FIG. 47. is an illustration of a bioinformatics workflow for determining DNA methylation levels. PCR2 products are combined, quantified and purified and subjected to next generation sequencing on a Miseq Illumina sequencer. Sequence is demultiplexed, FASTQ files are generated for each patient and analyzed with the workflow shown in the scheme. DNA methylation scores are calculated for each patient.

DETAILED DESCRIPTION

All illustrations of the drawings are for the purpose of describing selected embodiments and are not intended to limit the scope of the claimed subject matter.

Embodiment 1. "Discovery of Categorically Unmethylated CGIDs Across Hundreds of Individuals in Normal Tissues and Blood DNA Cell free DNA originating in tumors is known to be found in body fluids such as plasma, urine and in feces. It is also established that DNA methylation profiles of CF tumor DNA are similar to tumor DNA (Dominguez-Vigil et al., 2018). A vast body of data has established that tumor DNA is differentially methylated compared to normal tissues (Luczak & Jagodzinski, 2006). Therefore, many groups have tried to delineate by logistic regressions CGID positions in DNA (CG IDs in the Illumina 450K manifest) that are differentially methylated between cancerous and its normal tissue of origin for example, liver cancer versus adjacent liver tissue. However, since these methods measure quantitative differences between cancer and untransformed tissue rather than categorical qualitative differences, these quantitative differences between tumor and normal tissue would be diluted and erased by CF DNA from normal tissue, leading to false negatives and reduced sensitivity. In addition, other tissues that were not included in the analysis might have a DNA methylation profile similar to tumor DNA and since most studies only compare the tumor DNA to its untransformed counterparts and not to other tissues, this could lead to false positives. Varying and unpredictable quantities of DNA from different tissues have been detected in CF DNA (Breitbach et al., 2014) and thus the measured DNA methylation reflects a composite of unknown and unpredictable mixture of tissue DNA from different sources and tumor DNA. Thousands of tumor samples have been subjected to genome wide DNA methylation analysis using Illumina 450K arrays and are found in the public domain (TCGA). Examining the profiles of methylation of many normal tissues as well as cancer tissues, the inventors noticed that there is a significant group of CGs in the genome that are completely unmethylated in all normal tissues but methylated in DNA from tumors. A subset of these sites is unmethylated across numerous individuals whose DNA methylation was profiled in the public domain. The inventors also noticed that in many cancers these robustly unmethylated sites become methylated in cancer. Thus, creating a qualitative "categorical difference" between tumor DNA and all other DNA that might be found in blood. Using deep next generation sequencing even few methylated molecules could be easily identified on a background of completely unmethylated copies.

Data Bases; Illumina 450K DNA Methylation Data

We used publicly available data bases of normalized beta values of methylation for –450,000 CG across the human genome from a large number of individuals deposited either in the Gene expression Omnibus (GEO) or The Cancer Genome Atlas TCGA public data bases. We used the following databases to derive the list of robustly unmethylated CG IDs in many normal tissues and blood DNA: GSE50192, GSE50192, GSE40279.

DNA from white blood cells is one of the main sources of CF DNA in plasma. The inventors first generated a list of 47981 CGIDS that are unmethylated in all individuals in 17 different somatic human tissues using Illumina 450K data in GSE50192 and the logical COUNTIF and IF functions in Excel:

$NmCGID_x = COUNTIF (betaCGID_x n_1 : n_t, ">0.1")$ $umCGID_x = IF(NmCGID_x = O, TRUE, FALSE)$ $NmCGID_x$ =number of normal subjects that have the $CGID_x$ methylated.

Figure 1:
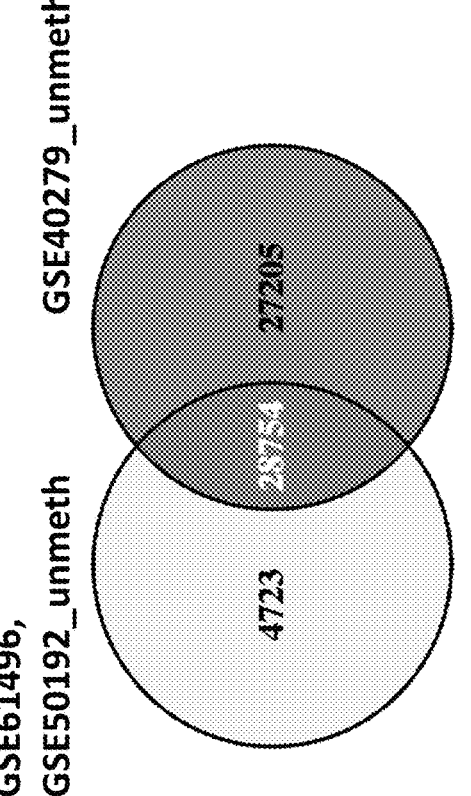
FIG. 1. shows a shortlist of completely unmethylated sites across blood samples and normal tissues in hundreds of individuals. Illustration A. shows CG IDs across 17 tissues that are unmethylated in all individuals (<0.1) in Illumina450K genome wide methylation arrays (GSE50192) were overlapped with unmethylated CG IDs in genome wide DNA methylation arrays of blood samples from 312 individuals (GSE61496) to generate a list of 33477 CG IDs. B illustrates shortlisting the most robustly unmethylated CG IDs the list of 33477 CG IDs from A was overlapped with unmethylated CG IDs in DNA methylation arrays of blood samples from 656 individuals (females and male) aged from 19 to 101 years (GSE40279). Combined, these analyses generated a list of high confidence 28754 CG IDs that are unmethylated across tissues and blood samples of many individuals across all age spans. These 28754 positions were used for discovery of sites that are categorically methylated in cancer but not in other tissues using the "binarycategorical differentiation (BCD)" method disclosed by the present inventive subject matter.
Figure 1:
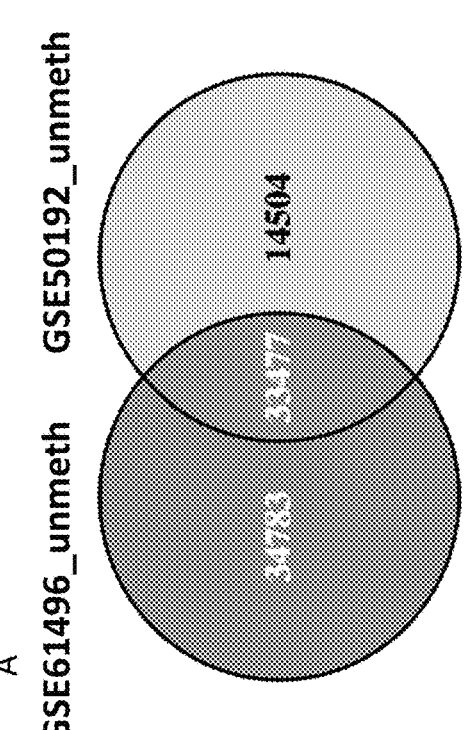

$umCGID_x$ =unmethylated $CGID_x$ in all subjects $betaCGID_x$ =the methylation values for a given $CGID_x$ x=any CGID on the Illumina 450k array $n_1$ =the first subject in the array, $n_t$ =the last subject in the array The inventors then generated a list of 68260 unmethylated CGIDs (UMCGIDs) in blood DNA from 312 individuals using the same criteria. The inventors then overlapped the list of 47981 and 68260 CG IDS and obtained a list of 33477 CG IDs that are unmethylated in both blood and somatic tissues across all individuals (FIG. 1A). To increase the robustness of this list of unmethylated CG IDs the inventors delineated a list of 60,379 CG IDs unmethylated CGIDs in Illumina 450K arrays of whole blood DNA from 656 individuals males and females aged from 19 to 101 years (GSE40279). These are robustly unmethylated sites in blood that are sex and age independent across hundreds of individuals. This list of 60,379 CG IDs was overlapped with the list of 33,477 CG IDs that are unmethylated both in somatic tissues and blood to generate a final list of 28,754 CG IDs which were used for discovery of categorical methylation markers for cancer. This list includes CG ID positions that are robustly unmethylated across tissues and individuals.

To identify DNA methylation positions that are categorically different between cancer and normal tissues the inventors examined whether any of these 28754 CG IDs are methylated in different cancers. The inventors noticed following examination of tumor DNA methylation data that methylation of a subset of these 28754 CG IDs is common in tumor DNA from individual patients. However, not all individuals have the same position methylated. Thus, a combination of CG IDs is required to detect cancer with high specificity. The inventors therefore discovered a polygenic combination of CG IDs for detection of cancers.

The inventors used 10 to 50 DNA methylation profiles from the public domain from either TCGA or GEO as a "discovery set" to discover a polygenic set of CGIDs whose methylation state is "categorically" different between tumor and normal tissues that could detect cancer with highest sensitivity and specificity. These CGIDs were then tested on hundreds of TCGA and GEO tumor DNA methylation array data as a "validation set" to validate the sensitivity and specificity of the polygenic DNA methylation markers for detecting cancer as disclosed in Embodiment 2.

Embodiment 2: Binary-Categorical Differentiation (BCD)" Method for Detecting Cancer in Cell Free DNA The following publicly available data bases of normalized beta values of methylation for −450,000 CGs (CG IDs) across the human genome were used to derive the list of cancer specific DNA methylation markers:

TABLE 29

| liver cancer | | | | |
|---|---|---|---|---|
| Disease Status | Source | Cohort | N | Detect/Spec |
| Normal Liver | GSE61258 | Discovery | 79 | Detect |
| HCC | TCGA | Discovery | 50 | Detect |
| HCC | TCGA | Discovery | 10 | Spec |
| Non-HCC cancers | TCGA | Discovery | 80 | Spec |
| HCC | GSE75041 | Validation | 66 | Detect |
| HCC | GSE76269 | Validation | 227 | Detect |
| HCC | TCGA | Validation | 430 | Detect |
| Bladder cancer | TCGA | Validation | 439 | Spec |
| Brain cancer | TCGA | Validation | 689 | Spec |
| Breast cancer | TCGA | Validation | 891 | Spec |
| Cervix cancer | TCGA | Validation | 312 | Spec |
| CRC cancer | TCGA | Validation | 459 | Spec |
| ESCA cancer | TCGA | Validation | 202 | Spec |
| Kidney cancer | TCGA | Validation | 871 | Spec |
| Lung cancer | TCGA | Validation | 919 | Spec |
| Ovarian cancer | TCGA | Validation | 10 | Spec |
| PANC cancer | TCGA | Validation | 195 | Spec |
| PRAD cancer | TCGA | Validation | 553 | Spec |

TABLE 29-continued

| liver cancer | | | | |
|---|---|---|---|---|
| Disease Status | Source | Cohort | N | Detect/Spec |
| Stomach cancer | TCGA | Validation | 397 | Spec |
| Testis cancer | TCGA | Validation | 156 | Spec |
| Normal Liver | GSE76269 | Validation | 10 | Spec |
| Normal Liver | GSE69852 | Validation | 6 | Spec |
| Normal Liver | GSE75041 | Validation | 10 | Spec |
| Normal Blood | GSE40279 | Validation | 656 | Spec |
| Normal Blood | GSE61496 | Validation | 312 | Spec |

TABLE 30

| lung cancer | | | | |
|---|---|---|---|---|
| Disease Status | Source | Cohort | N | Detect/Spec |
| Lung Cancer | GSE63704 | Discovery | 10 | Detect |
| Normal Lung | GSE66836 | Discovery | 10 | Detect |
| Lung Cancer | TCGA | Discovery | 10 | Spec |
| Non-lung cancers | TCGA | Discovery | 80 | Spec |
| Lung Cancer | GSE66836 | Validation | 164 | Detect |
| Lung Cancer | GSE63704 | Validation | 17 | Detect |
| Lung Cancer | GSE76269 | Validation | 56 | Detect |
| Lung Cancer | TCGA | Validation | 919 | Spec |
| Bladder Cancer | TCGA | Validation | 439 | Detect |
| Brain Cancer | TCGA | Validation | 689 | Spec |
| Breast Cancer | TCGA | Validation | 891 | Spec |
| Cervical Cancer | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Ovarian Cancer | TCGA | Validation | 10 | Spec |
| PANC | TCGA | Validation | 195 | Spec |
| PRAD | TCGA | Validation | 553 | Spec |
| Stomach Cancer | TCGA | Validation | 396 | Spec |
| Testis Cancer | TCGA | Validation | 156 | Spec |
| Normal Lung | GSE63704 | Validation | 112 | Detect |

TABLE 31

| prostate cancer | | | | |
|---|---|---|---|---|
| Disease Status | Source | Cohort | N | Detect/Spec |
| Control | GSE52955 | Discovery | 5 | Detect |
| PRAD | TCGA | Discovery | 10 | Detect |
| PRAD | TCGA | Discovery | 10 | Spec |
| Non-PRAD | TCGA | Discovery | 80 | Spec |
| PRAD | GSE73549 | Validation | 77 | Detect |
| PRAD | GSE52955 | Validation | 25 | Detect |
| PRAD | TCGA | Validation | 553 | Spec |
| Bladder | TCGA | Validation | 439 | Spec |
| Brain | TCGA | Validation | 689 | Spec |
| Breast | TCGA | Validation | 891 | Spec |
| Cervix | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney | TCGA | Validation | 871 | Spec |
| Lung | TCGA | Validation | 919 | Spec |
| Ovarian | TCGA | Validation | 10 | Spec |
| PANC | TCGA | Validation | 195 | Spec |
| Stomach | TCGA | Validation | 397 | Spec |
| Testis | TCGA | Validation | 156 | Spec |
| Normal Prostate | GSE73549 | Validation | 15 | Detect |
| Normal Prostate | GSE52955 | Validation | 5 | Detect |
| Normal Blood | GSE40279 | Validation | 656 | Spec |
| Normal Blood | GSE61496 | Validation | 312 | Spec |

TABLE 32 breast cancer

| Disease Status | Source | Cohort | N | Detect/Spec |
|---|---|---|---|---|
| Healthy | GSE60185 | Discovery | 17 | Detect |
| Breast Cancer | TCGA | Discovery | 10 | Detect |
| Breast Cancer | TCGA | Discovery | 10 | Spec |
| Non-breast cancers | TCGA | Discovery | 80 | Spec |
| Breast Cancer | GSE60185 | Validation | 239 | Detect |
| Breast Cancer | GSE75067 | Validation | 188 | Detect |
| Breast Cancer | TCGA | Validation | 891 | Detect |
| Bladder Cancer | TCGA | Validation | 439 | Spec |
| brain Cancer | TCGA | Validation | 689 | Spec |
| Cervical Cancer | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| Ovarian Cancer | TCGA | Validation | 10 | Spec |
| PANC | TCGA | Validation | 195 | Spec |
| PRAD | TCGA | Validation | 553 | Spec |
| Stomach Cancer | TCGA | Validation | 396 | Spec |
| Testis Cancer | TCGA | Validation | 156 | Spec |
| Healthy breast tissue | GSE101961 | Validation | 121 | Detect |
| Healthy breast tissue | GSE60185 | Validation | 17 | Detect |
| Normal adjasent tissue | GSE60185 | Validation | 29 | Detect |
| Normal Blood | GSE40279 | Validation | 656 | Spec |
| Normal Blood | GSE61496 | Validation | 312 | Spec |

TABLE 33 colorectal cancer CRC

| Disease Status | Source | Cohort | N | Detect/Spec |
|---|---|---|---|---|
| Control | GSE6550 | Discovery | 25 | Detect |
| CRC | TCGA | Discovery | 50 | Detect |
| CRC | TCGA | Discovery | 10 | Spec |
| Non-HCC | TCGA | Discovery | 80 | Spec |
| CRC | TCGA | Validation | 260 | Detect |
| HCC | TCGA | Validation | 459 | Detect |
| Bladder | TCGA | Validation | 439 | Spec |
| Brain | TCGA | Validation | 689 | Spec |
| Breast | TCGA | Validation | 891 | Spec |
| Cervix | TCGA | Validation | 312 | Spec |
| ESCA | TCGA | Validation | 202 | Spec |
| HCC | TCGA | Validation | 430 | Spec |
| Kidney | TCGA | Validation | 871 | Spec |
| Lung | TCGA | Validation | 919 | Spec |
| Ovarian | TCGA | Validation | 10 | Spec |
| PANC | TCGA | Validation | 195 | Spec |
| PRAD | TCGA | Validation | 553 | Spec |
| Stomach | TCGA | Validation | 397 | Spec |
| Testis | TCGA | Validation | 156 | Spec |
| Normal Colorectal | GSE6550 | Validation | 8 | Detect |
| Normal Blood | GSE40279 | Validation | 656 | Spec |
| Normal Blood | GSE61496 | Validation | 312 | Spec |

TABLE 34

Pancreatic cancer

| Disease Status | Source | Cohort | N | Detect/Spec |
|---|---|---|---|---|
| Healthy | GSE53051 | Discovery | 12 | Detect |
| Pancreatic Cancer | TCGA | Discovery | 20 | Detect |
| Pancreatic Cancer | TCGA | Discovery | 20 | Spec |
| Non-pancreatic | TCGA | Discovery | 100 | Spec |
| Pancreatic Cancer | E-MTAB-5 | Validation | 24 | Detect |
| Pancreatic Cancer | TCGA | Validation | 195 | Detect |
| Bladder Cancer | TCGA | Validation | 439 | Spec |
| brain Cancer | TCGA | Validation | 689 | Spec |
| Breast Cancer | TCGA | Validation | 891 | Spec |
| Cervical Cancer | TCGA | Validation | 312 | Spec |

TABLE 34-continued

Pancreatic cancer

| Disease Status | Source | Cohort | N | Detect/Spec |
|---|---|---|---|---|
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| Ovarian Cancer | TCGA | Validation | 10 | Spec |
| PRAD | TCGA | Validation | 553 | Spec |
| Stomach Cancer | TCGA | Validation | 396 | Spec |
| Testis Cancer | TCGA | Validation | 156 | Spec |
| Normal Blood | GSE40179 | Validation | 656 | Spec |
| Normal Blood | GSE61496 | Validation | 312 | Spec |

TABLE 35

Brain cancer

| Disease Status | Source | Cohort | N | Detect/Spec |
|---|---|---|---|---|
| Brain Cancer | TCGA | Discovery | 10 | Spec-Detect |
| Non-brain cancer | TCGA | Discovery | 158 | Spec-Detect |
| Brain Cancer | GSE36278 | Validation | 136 | Spec-Detect |
| Brain Cancer | GSE58298 | Validation | 40 | Spec-Detect |
| Brain Cancer | GSE58218 | Validation | 228 | Spec-Detect |
| Brain Cancer | TCGA | Validation | 689 | Spec-Detect |
| Bladder Cancer | TCGA | Validation | 439 | Spec-Detect |
| Breast Cancer | TCGA | Validation | 891 | Spec-Detect |
| Cervical Cancer | TCGA | Validation | 312 | Spec-Detect |
| CRC | TCGA | Validation | 459 | Spec-Detect |
| ESCA | TCGA | Validation | 202 | Spec-Detect |
| HCC | TCGA | Validation | 430 | Spec-Detect |
| Kidney Cancer | TCGA | Validation | 871 | Spec-Detect |
| Lung Cancer | TCGA | Validation | 919 | Spec-Detect |
| Ovarian Cancer | TCGA | Validation | 10 | Spec-Detect |
| PANC | TCGA | Validation | 195 | Spec-Detect |
| PRAD | TCGA | Validation | 553 | Spec-Detect |
| Stomach Cancer | TCGA | Validation | 396 | Spec-Detect |
| Testis Cancer | TCGA | Validation | 156 | Spec-Detect |
| Brain Cancer | GSE36278 | Validation | 6 | Spec-Detect |
| Normal Blood | GSE40279 | Validation | 656 | Spec-Detect |
| Normal Blood | GSE61496 | Validation | 312 | Spec-Detect |

TABLE 36

Stomach cancer

| Disease Status | Source | Cohort | N | Detect/Spec |
|---|---|---|---|---|
| Healthy | GSE99553 | Discovery | 14 | Detect |
| Stomach Cancer | TCGA | Discovery | 20 | Detect |
| Stomach Cancer | TCGA | Discovery | 7 | Spec |
| Non-stomach cancer | TCGA | Discovery | 100 | Spec |
| Stomach Cancer | TCGA | Validation | 396 | Detect |
| Bladder Cancer | TCGA | Validation | 439 | Spec |
| brain Cancer | TCGA | Validation | 689 | Spec |
| Breast Cancer | TCGA | Validation | 891 | Spec |
| Cervical Cancer | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| Ovarian Cancer | TCGA | Validation | 10 | Spec |
| PANC | TCGA | Validation | 195 | Spec |
| PRAD | TCGA | Validation | 553 | Spec |
| Testis Cancer | TCGA | Validation | 156 | Spec |
| Normal Tissue | GSE99553 | Validation | 42 | Detect |
| Normal Blood | GSE40179 | Validation | 656 | Spec |
| Normal Blood | GSE61496 | Validation | 312 | Spec |

TABLE 37

Ovarian cancer

| Disease Status | Source | Cohort | N | Detect/Spec |
|---|---|---|---|---|
| Healthy | GSE65821 | Discovery | 6 | Detect |
| Ovarian Cancer | TCGA | Discovery | 10 | Detect |
| Ovarian Cancer | TCGA | Discovery | 10 | Spec |
| Non-ovarian cancers | TCGA | Discovery | 110 | Spec |
| Ovarian Cancer | GSE65821 | Validation | 113 | Detect |
| Bladder Cancer | TCGA | Validation | 439 | Spec |
| brain Cancer | TCGA | Validation | 689 | Spec |
| Breast Cancer | TCGA | Validation | 891 | Detect |
| Cervical Cancer | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| PANC | TCGA | Validation | 195 | Spec |
| PRAD | TCGA | Validation | 553 | Spec |
| Stomach Cancer | TCGA | Validation | 396 | Spec |
| Testis Cancer | TCGA | Validation | 156 | Spec |
| Healthy ovarian tissue | GSE87621 | Validation | 9 | Detect |
| Healthy ovarian tissue | GSE74845 | Validation | 216 | Detect |
| Healthy ovarian tissue | GSE81228 | Validation | 10 | Detect |
| Normal Blood | GSE40279 | Validation | 656 | Spec |

TABLE 38

Cervical cancer

| Disease Status | Source | Cohort | N | Detect/Spec |
|---|---|---|---|---|
| Healthy | GSE46306 | Discovery | 20 | Detect |
| Cervical Cancer | TCGA | Discovery | 10 | Detect |
| Cervical Cancer | TCGA | Discovery | 10 | Spec |
| Non-cervical cancers | TCGA | Discovery | 110 | Spec |
| Cervical Cancer | GSE68339 | Validation | 270 | Detect |
| Cervical Cancer | TCGA | Validation | 312 | Detect |
| Bladder Cancer | TCGA | Validation | 439 | Spec |
| brain Cancer | TCGA | Validation | 689 | Spec |
| Breast Cancer | TCGA | Validation | 891 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| Ovarian Cancer | TCGA | Validation | 10 | Spec |
| PANC | TCGA | Validation | 195 | Spec |
| PRAD | TCGA | Validation | 553 | Spec |
| Stomach Cancer | TCGA | Validation | 396 | Spec |
| Testis Cancer | TCGA | Validation | 156 | Spec |
| Normal Blood | GSE40279 | Validation | 656 | Spec |
| Normal Blood | GSE61496 | Validation | 312 | Spec |

TABLE 39

HNSC

| Disease Status | Source | Cohort | N | Detect/Spec |
|---|---|---|---|---|
| HNSC | TCGA | Discovery | 20 | Detect |
| Control | GSE75537 | Discovery | 10 | Detect |
| HNSC | TCGA | Discovery | 20 | Spec |
| Non-HNSC | TCGA | Discovery | 190 | Spec |
| Healthy | GSE40279 | Discovery | 10 | Spec |
| HNSC | TCGA | Validation | 580 | Detect |
| Control | GSE52068 | Validation | 24 | Detect |
| HNSC | GSE75537 | Validation | 54 | Detect |
| HNSC | GSE79556 | Validation | 83 | Detect |
| Control | GSE75537 | Validation | 54 | Detect |
| HNSC | GSE52068 | Validation | 24 | Detect |
| Bladder | TCGA | Validation | 439 | Spec |
| Brain | TCGA | Validation | 689 | Spec |
| Breast | TCGA | Validation | 891 | Spec |

TABLE 39-continued

HNSC

| Disease Status | Source | Cohort | N | Detect/Spec |
|---|---|---|---|---|
| Cervix | TCGA | Validation | 312 | Spec |
| HCC | TCGA | Validation | 459 | Spec |
| ESCA | TCGA | Validation | 202 | Spec |
| HCC | TCGA | Validation | 430 | Spec |
| Kidney | TCGA | Validation | 871 | Spec |
| Lung | TCGA | Validation | 919 | Spec |
| Ovarian | TCGA | Validation | 10 | Spec |
| PANC | TCGA | Validation | 195 | Spec |
| PRAD | TCGA | Validation | 553 | Spec |
| Stomach | TCGA | Validation | 396 | Spec |
| Testis | TCGA | Validation | 156 | Spec |
| Normal Blood | GSE40279 | Validation | 656 | Spec |
| Normal Blood | GSE52068 | Validation | 312 | Spec |

TABLE 40

Esophageal cancer

| Disease Status | Source | Cohort | N | Detect/Spec |
|---|---|---|---|---|
| Esophageal Cancer | IGSE52826 | Discovery | 6 | Detect |
| ESCA | TCGA | Discovery | 10 | Detect |
| Non-esophageal cancer | TCGA | Discovery | 190 | Spec |
| Healthy blood | GSE40279 | Discovery | 10 | Spec |
| ESCA | TCGA | Discovery | 20 | Spec |
| Esophageal Cancer | TCGA | Validation | 202 | Detect |
| Bladder Cancer | TCGA | Validation | 439 | Spec |
| Brain Cancer | TCGA | Validation | 689 | Spec |
| Breast Cancer | TCGA | Validation | 891 | Spec |
| Cervical Cancer | TCGA | Validation | 312 | Spec |
| CRC Cancer | TCGA | Validation | 459 | Spec |
| Renal Cancer | TCGA | Validation | 871 | Spec |
| HNSC | TCGA | Validation | 580 | Spec |
| HCC | TCGA | Validation | 430 | Spec |
| Lung Cancer | TCGA | Validation | 919 | Spec |
| Ovarian Cancer | TCGA | Validation | 10 | Spec |
| Pancreatic Cancer | TCGA | Validation | 195 | Spec |
| Prostate Cancer | TCGA | Validation | 553 | Spec |
| Stomach Cancer | TCGA | Validation | 397 | Spec |
| Testis | TCGA | Validation | 156 | Spec |
| Normal Blood | GSE40279 | Validation | 656 | Spec |
| Normal Blood | GSE61496 | Validation | 312 | Spec |
| Normal tissues | Mix | Validation | 115 | Spec |
| Normal tissues | GSE85566 | Validation | 189 | Spec |

TABLE 41

Bladder cancer

| Disease Status | Source | Cohort | N | Detect/Spec |
|---|---|---|---|---|
| Bladder Cancer | TCGA | Discovery | 10 | Detect |
| Normal bladder | GSE52955 | Discovery | 5 | Detect |
| Bladder Cancer | TCGA | Discovery | 10 | Spec |
| Non-bladder cancers | TCGA | Discovery | 180 | Spec |
| Bladder Cancer | TCGA | Validation | 439 | Detect |
| Brain Cancer | TCGA | Validation | 689 | Spec |
| Breast Cancer | TCGA | Validation | 891 | Spec |
| Cervical Cancer | TCGA | Validation | 312 | Spec |
| CRC | TCGA | Validation | 459 | Spec |
| ESCA | TCGA | Validation | 202 | Spec |
| HCC | TCGA | Validation | 430 | Spec |
| Kidney Cancer | TCGA | Validation | 871 | Spec |
| Lung Cancer | TCGA | Validation | 919 | Spec |
| Ovarian Cancer | TCGA | Validation | 10 | Spec |
| PANC | TCGA | Validation | 195 | Spec |
| PRAD | TCGA | Validation | 553 | Spec |
| Stomach Cancer | TCGA | Validation | 396 | Spec |
| Testis Cancer | TCGA | Validation | 156 | Spec |
| Normal tissues | GSE50192 | Validation | 70 | Spec |

TABLE 41-continued

Bladder cancer

| Disease Status | Source | Cohort | N | Detect/Spec |
|---|---|---|---|---|
| Normal Blood | GSE40279 | Validation | 656 | Spec |
| Normal Blood | GSE61496 | Validation | 312 | Spec |

TABLE 42

Kidney cancer

| Disease Status | Source | Cohort | N | Detect/Spec |
|---|---|---|---|---|
| Control | GSE52955 | Discovery | 6 | Spec-Detect |
| Kidney Cancer | TCGA | Discovery | 30 | Spec-Detect |
| Healthy blood | GSE40279 | Discovery | 10 | Spec-Detect |
| Non-kidney cancer | TCGA | Discovery | 180 | Spec-Detect |
| Kidney | TCGA | Validation | 871 | Spec-Detect |
| Bladder | TCGA | Validation | 439 | Spec-Detect |
| Brain | TCGA | Validation | 689 | Spec-Detect |
| Breast | TCGA | Validation | 891 | Spec-Detect |
| Cervix | TCGA | Validation | 312 | Spec-Detect |
| CRC | TCGA | Validation | 459 | Spec-Detect |
| ESCA | TCGA | Validation | 202 | Spec-Detect |
| HNSC | TCGA | Validation | 580 | Spec-Detect |
| HCC | TCGA | Validation | 430 | Spec-Detect |
| Lung | TCGA | Validation | 919 | Spec-Detect |
| Ovarian | TCGA | Validation | 10 | Spec-Detect |
| PANC | TCGA | Validation | 195 | Spec-Detect |
| PRAD | TCGA | Validation | 553 | Spec-Detect |
| Stomach | TCGA | Validation | 397 | Spec-Detect |
| Testis | TCGA | Validation | 156 | Spec-Detect |
| Normal Blood | GSE40279 | Validation | 656 | Spec-Detect |
| Normal Blood | GSE61496 | Validation | 312 | Spec-Detect |
| Normal tissues | Mix | Validation | 189 | Spec-Detect |
| Normal tissues | GSE85566 | Validation | 115 | Spec-Detect |

TABLE 43

Testicular cancer

| Disease Status | Source | Cohort | N | Detect/Spec |
|---|---|---|---|---|
| Testicular Cancer | TCGA | Discovery | 10 | Spec-Detect |
| Healthy blood | GSE40279 | Discovery | 10 | Spec-Detect |
| Non-testis cancers | TCGA | Discovery | 170 | Spec-Detect |
| Testis Cancer | TCGA | Validation | 156 | Spec-Detect |
| Bladder Cancer | TCGA | Validation | 439 | Spec-Detect |
| Brain Cancer | TCGA | Validation | 689 | Spec-Detect |
| Breast Cancer | TCGA | Validation | 891 | Spec-Detect |
| Cervical Cancer | TCGA | Validation | 312 | Spec-Detect |
| CRC | TCGA | Validation | 459 | Spec-Detect |
| ESCA | TCGA | Validation | 202 | Spec-Detect |
| HCC | TCGA | Validation | 430 | Spec-Detect |
| Kidney Cancer | TCGA | Validation | 871 | Spec-Detect |
| Lung Cancer | TCGA | Validation | 919 | Spec-Detect |
| Ovarian Cancer | TCGA | Validation | 10 | Spec-Detect |
| PANC | TCGA | Validation | 195 | Spec-Detect |
| PRAD | TCGA | Validation | 553 | Spec-Detect |
| Stomach Cancer | TCGA | Validation | 396 | Spec-Detect |
| Normal tissues | GSE50192 | Validation | 70 | Spec-Detect |
| Normal tissues | Mix | Validation | 119 | Spec-Detect |
| Normal Blood | GSE40279 | Validation | 656 | Spec-Detect |
| Normal Blood | GSE61496 | Validation | 312 | Spec-Detect |

TABLE 44

Pan-cancer

| Disease Status | Source | Cohort | N | Detect/Spec |
|---|---|---|---|---|
| Healthy Blood | GSE40279 | Discovery | 10 | Detect |
| TCGA cancers | TCGA | Discovery | 170 | Detect |

TABLE 44-continued

Pan-cancer

| Disease Status | Source | Cohort | N | Detect/Spec |
|---|---|---|---|---|
| Bladder Cancer | TCGA | Validation | 439 | Detect |
| Brain Cancer | TCGA | Validation | 689 | Detect |
| Breast Cancer | TCGA | Validation | 891 | Detect |
| Cervical Cancer | TCGA | Validation | 312 | Detect |
| CRC Cancer | TCGA | Validation | 459 | Detect |
| Esophagus Cancer | TCGA | Validation | 202 | Detect |
| HNSC Cancer | TCGA | Validation | 580 | Detect |
| HCC Cancer | TCGA | Validation | 430 | Detect |
| Lung Cancer | TCGA | Validation | 919 | Detect |
| Ovarian Cancer | TCGA | Validation | 10 | Detect |
| Pancreatic Cancer | TCGA | Validation | 195 | Detect |
| Prostate Cancer | TCGA | Validation | 553 | Detect |
| Stomach Cancer | TCGA | Validation | 397 | Detect |
| Normal Blood | GSE40279 | Validation | 656 | Detect |
| Normal Blood | GSE61496 | Validation | 312 | Detect |

TABLE 45

Melanoma

| Disease Status | Source | Cohort | N | Detect/Spec |
|---|---|---|---|---|
| Bladder Cancer | TCGA | Validation | 439 | Detect/Spec |
| Brain Cancer | TCGA | Validation | 689 | Detect/Spec |
| Breast Cancecer | TCGA | Validation | 891 | Detect/Spec |
| Cervical Cancer | TCGA | Validation | 312 | Detect/Spec |
| CRC Cancer | TCGA | Validation | 459 | Detect/Spec |
| Esophagus Cancer | TCGA | Validation | 202 | Detect/Spec |
| HNSC Cancer | TCGA | Validation | 580 | Detect/Spec |
| HCC Cancer | TCGA | Validation | 430 | Detect/Spec |

TABLE 46

AML

| Disease Status | Source | Cohort | N | Detect/Spec |
|---|---|---|---|---|
| Normal Blood | GSE40279 | Validation | 656 | Detect/Spec |
| Normal Blood | GSE61496 | Validation | 312 | Detect/Spec |
| AML | GSE86409 | Validation | 79 | Detect/Spec |
| AML | TCGA | Validation | 140 | Detect/Spec |

BCD Method

The following are the steps of the Binary Categorical Differentiation method (BCD) invented by the inventors to discover polygenic DNA methylation markers for early prediction of different cancers.

We filtered the 28,754 CGIDs that are robustly unmethylated in normal tissues.

For the discovery cohort we delineated within the list of 28,754 CG IDs that are robustly unmethylated in normal tissues, CGIDs that are categorically methylated in a particular cancer and are not methylated in unaffected tissue and normal tissues using the COUNTIF and IF functions in Microsoft excel.

$NmcCGID_x$=COUNTIF (betaCGIDxCancer $n_1$:$n_i$,">0.2")

$NmnCGIDx$=COUNTIF (betaCGIDxNormal $n_1$:$n_i$, ">0.1")

$DMCGID_x$=IF((AND($NmcCGID_x$>0, $NmnCGID_x$=0)), "TRUE","FALSE")

DM $CGID_x$ were sorted from highest to lowest number

Up to 20 top TRUE DM $CGID_x$ positions were selected $NmcCGID_x$=Number of cancer patients with methylated $CGID_x$ Nmn=number of normal adjacent or similar tissue samples with methylated $CGID_x$ $betaCGID_x$=level of methylation of $CGID_x$ n=patient from 1 to I DM=differentially methylated $CGID_x$ The inventors noticed that testicular and kidney cancer exhibit pervasive lack of methylation at CG IDs that are highly methylated in all tissues. We therefore used a modification of the BCD method to discover categorically differentially methylated CG ID positions for testicular and kidney (renal) cancer which we term "BCDhypo"; categorically unmethylated in cancer and methylated in normal tissue. The following steps were used for discovery of Differentially hypomethylated CGID positions in testicular and kidney cancer.

For the discovery cohort we delineated hypomethylated CGIDs in testis or kidney that are fully methylated in normal tissues using the COUNTIF and IF functions in excel.

$NucCGID_x$=COUNTIF ($betaCGID_x$Cancer $n_1$:$n_i$,"<0.2")

$NunCGID_x$=COUNTIF ($betaCGID_x$Normal $n_1$:$n_i$,"<0.9")

$DHMCGID_x$=IF((AND($NucCGID_x$>0, $NunCGID_x$=0)), "TRUE","FALSE")

DHM CGID positions were sorted from highest to lowest number 20 top TRUE DHM sites were selected and subjected to penalized regression analysis $NucCGID_x$=Number of cancer patients with unmethylated CGID X $NunCGID_x$=number of normal tissue samples with unmethylated CGID X n=patient from 1 to i DHM=differentially hypomethylated CGID The inventors then performed on the top 20 DM (or DHM) CGIDx a penalized regression using the package penalized in R to delineate the minimal combination of CGIDx that predicts cancer at highest sensitivity and specificity. The polygenic combination of CGIDx was further tested in a multivariate linear regression equation to determine the regression coefficient between methylation levels of these CGIDs in the polygenic combination and cancer. The model was used to calculate a methylation score for each patient for a typical cancer.

$$Ms = \alpha + \Sigma_{i=1}^{n} \beta_i CG_i$$

Ms=methylation score, $\alpha$=intercept, $\beta_i$=coefficient for CG $ID_i$, $CG_i$=methylation level per CG in combination. 1 to i=number of CGs in combination.

Embodiment 3. Discovery of a Polygenic DNA Methylation Marker for Liver Cancer (HCC)

Figure 5:
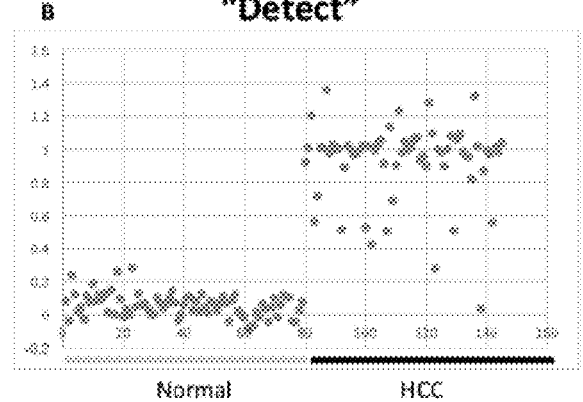
FIG. 5 is an illustration showing a discovery of a polygenic DNA methylation marker for early detection of liver cancer (HCC). Illustration A shows a table which lists the source and number of patients whose methylation data was used for the discovery of a set of 4 CGIDs for detection of HCC according to an embodiment using the BCD method (Table 1) and CG IDs for determining the specific cancer of origin (Table 2). Illustration B at the bottom left panel of FIG. 5 (Detect) shows the combined methylation score for these CG IDs (Table 1) for each of the tested people listed from 1-145 (79 normal and 66 HCC). The polygenic score categorically differentiates between people with HCC and normal liver tissue. Illustration C at the bottom right panel shows the methylation score for the 1 CGID detecting the specific tumor origin (Table 2) using data on 8 different tumors (Table 2). The markers categorically differentiate between cancers from other origins and HCC.
Figure 5:
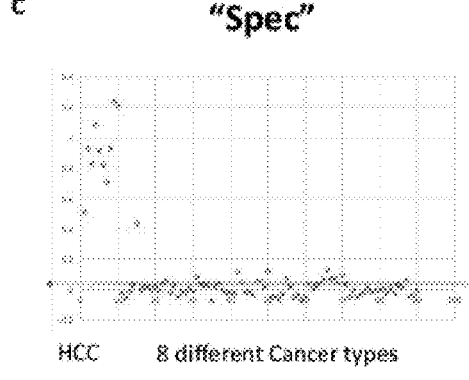

The inventors used normalized Illumina 450K DNA methylation data from GSE61258 (normal liver) and 66 randomly selected samples from the TCGA HCC collection of HCC DNA methylation data as a "training" cohort. The inventors first shortlisted in the "training cohort" dataset 28754 CGIDx that were discovered in embodiment 1 as sites that are robustly unmethylated across normal tissues and blood samples. The inventors then used the BCD method described in embodiment 2 to discover a polygenic set of binary categorical differentially methylated CGIDs that detect HCC with high sensitivity and specificity in the training cohort (FIG. 5B, Table 1) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types. The inventors used this training cohort to discover a polygenic set of differentially methylated CGIDs between HCC and other tumors (FIG. 5C, Table 2) (spec). A weighted DNA methylation score was developed for the CGIDs as described in embodiment 2.

Figure 6:
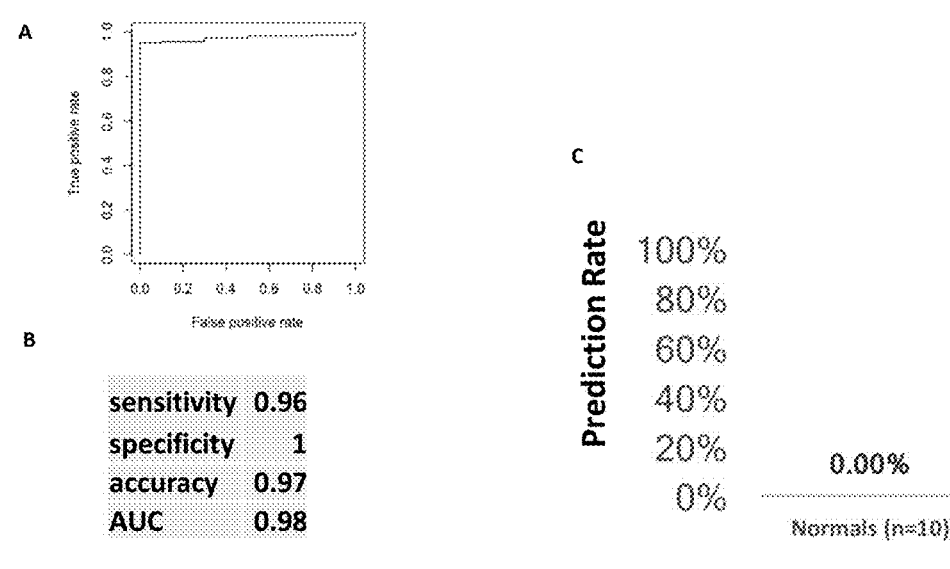
FIG. 6 is an illustration of a validation of a polygenic DNA methylation marker for HCC (spec) using DNA methylation data from GSE76269 (n=227). Illustration A is a ROC plot showing area under the curve for the HCC DNA methylation markers using 227 liver cancer patient DNA methylation data and 10 normal. Illustration B of FIG. 6 shows the sensitivity, specificity and accuracy of HCC detection. Illustration C shows the prediction rate of detection of HCC in the validation dataset.
Figure 7:
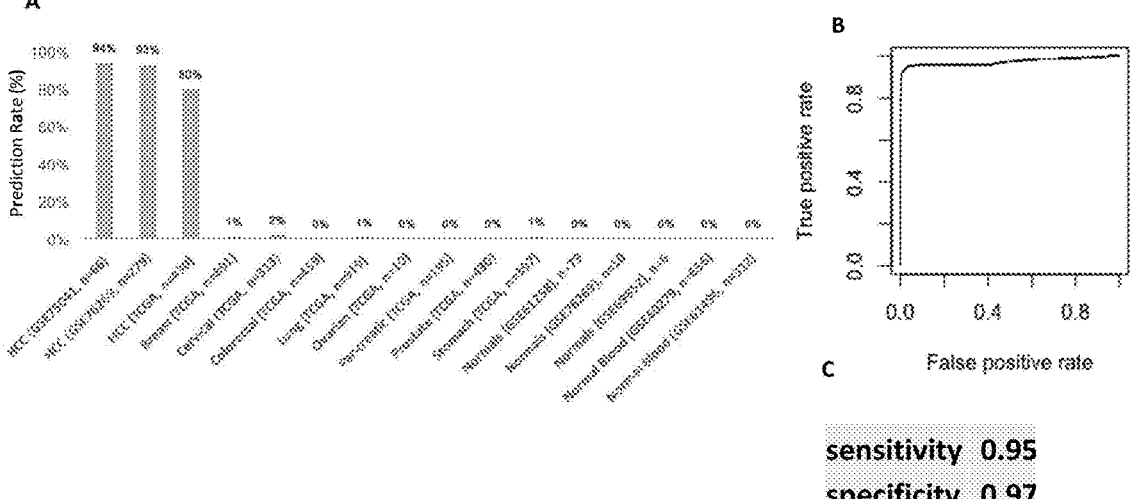
FIG. 7 is an illustration of a validation of the polygenic HKG-epiLiver-detect and spec markers accuracy and specificity for HCC versus other cancers in TCGA methylation data (n=4166). Illustration A of FIG. 7 shows a detection rate of the HKG-Liver detect/spec markers DNA methylation data of patients with different cancers. Note the almost perfect specificity for HCC. B. ROC plot of the HKG-Liver-detect markers specificity and sensitivity for HCC in 4166 patient DNA methylation data from TCGA. C. Sensitivity and specificity to HCC versus cancers from other origins.

Embodiment 4. Utility of HCC Polygenic DNA Methylation Markers for Detecting HCC The inventors then demonstrated that the weighted HCC DNA methylation score detected HCC in a "validation cohort" that included normalized Illumina 450K DNA methylation beta values from GSE76269 for 227 HCC patients for the CGIDs in Table 1. Using this method, 95% of the HCC samples were detected as HCC (FIG. 6C). A ROC curve presented in FIG. 6A reveals the specificity (1) and sensitivity (0.96) of this methylation score for detecting cancer. The inventors then demonstrated the utility of the combined spec and detect DNA methylation scores for detecting HCC and differentiating between HCC and other cancers using a "validation cohort" with methylation data from GSE75041 and TCGA for HCC and 8 other types of cancer. A ROC curve presented in FIG. 7B reveals the specificity (0.97) and sensitivity (0.95) of this methylation score for differentiating HCC from other normal tissue and other cancers. These DNA methylation markers and the calculated methylation score could be used for screening and early detection of cancer in people at risk as well as the general healthy population using different biomaterial from people such as tissue, feces, saliva, plasma and urine.

Embodiment 5. Discovery of a Polygenic DNA Methylation Marker for Lung Cancer The inventors used normalized Illumina 450K DNA methylation data for 10 people from GSE61258 (normal lung) and 10 randomly selected samples from the TCGA lung cancer collection of lung cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect lung cancer with high sensitivity and specificity (Samples included both adenocarcinoma and squamous cell carcinoma) in the training cohort (FIG. 8B, Table 3) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types. The inventors used this training cohort to discover a polygenic set of differentially methylated CGIDs between lung cancer and other tumors (FIG. 8C, Table 4) (spec). A weighted DNA methylation score was developed for the CGIDs as described in embodiment 2.

Embodiment 6. Utility of Lung Polygenic DNA Methylation Markers for Detecting Lung Cancer The inventors then demonstrated that the weighted lung cancer DNA methylation score and threshold developed in embodiment 3 (detect) detects lung cancer in a "validation cohort" that included normalized Illumina 450K DNA methylation beta values from GSE66836, GSE63704, GSE76269 and 919 lung cancer patients from TCGA. Using this method 96% of the lung cancer samples were detected as lung cancer (FIG. 9A). The inventors then demonstrated the utility of the combined spec and detect DNA methylation scores for differentiating between lung cancer and other cancers using a "validation cohort" with methylation data from GSE and TCGA for lung cancer and 8 other types of cancer (FIG. 9A). A ROC curve presented in FIG. 9B reveals the specificity (0.96) and sensitivity (0.84) of this methylation score for detecting lung cancer from other normal tissue and other cancers (FIG. 9C). These DNA methylation markers and the calculated methylation score could be used for early detection of cancer in people at risk as well as the general healthy population using different biomaterial from the patient from tissues, feces, saliva, plasma and urine.

Embodiment 7. Discovery of a Polygenic DNA Methylation Marker for Prostate Cancer The inventors used normalized Illumina 450K DNA methylation data for 5 people from GSE52955 (normal prostate) and 10 randomly selected samples from the TCGA prostate cancer collection of prostate cancer DNA methylation data as a "training" cohort. The inventors first shortlisted in the "training cohort" dataset 28754 CGIDs that were discovered in embodiment 1 as sites that robustly unmethylated across normal tissues and blood samples. The inventors then used the BCD method described in embodiment 2 to discover a polygenic set of binary categorical differentially methylated CGIDs that detect prostate cancer with high sensitivity and specificity in the training cohort (FIG. 10b, Table 5) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types. The inventors used this training cohort to discover a polygenic set of differentially methylated CGIDs between prostate cancer and other tumors (FIG. 10C, Table 6) (spec). A weighted DNA methylation score was developed for the CGIDs as described in embodiment 2.

Embodiment 8. Utility of Prostate Cancer Polygenic DNA Methylation Markers for Detecting Prostate Cancer The inventors then demonstrated that the weighted prostate cancer DNA methylation score and threshold developed in embodiment 3 (detect) detects prostate cancer in a "validation cohort" that included normalized Illumina 450K DNA methylation beta values from GSE73549, GSE2955, and 430 prostate cancer patients from TCGA. Using this method 99% of the prostate cancer samples were detected as prostate cancer (FIG. 11A). The inventors then demonstrated the utility of the combined spec and detect DNA methylation scores for differentiating between prostate cancer and other cancers using a "validation cohort" with methylation data from GSE and TCGA for prostate cancer and 8 other types of cancer (FIG. 11A). A ROC curve presented in FIG. 11B reveals the specificity (0.99) and sensitivity (0.98) of this methylation score for detecting prostate cancer from other normal tissue and other cancers (FIG. 11C). These DNA methylation markers and the calculated methylation score could be used for early detection of cancer in people at risk as well as the general healthy population using different biomaterial from the patient from tissues, feces, saliva, plasma and urine.

Embodiment 9. Discovery of a Polygenic DNA Methylation Marker for Breast Cancer The inventors used normalized Illumina 450K DNA methylation data for 17 people from GSE60185 (normal breast) and 10 randomly selected samples from the TCGA breast cancer collection of breast cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect breast cancer with high sensitivity and specificity in the training cohort (FIG. 12B, Table 7) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types. The inventors used this training cohort to discover a polygenic set of differentially methylated CGIDs between breast cancer and other tumors (FIG. 12C, Table 8) (spec). A weighted DNA methylation score was developed for the CGIDs as described in embodiment 2.

Embodiment 10. Utility of Breast Cancer Polygenic DNA Methylation Markers for Detecting Breast Cancer The inventors then demonstrated that the weighted breast cancer DNA methylation score and threshold developed in embodiment 9 (detect) detects breast cancer in a "validation cohort" that included 891 breast cancer patients using normalized Illumina 450K DNA methylation beta values from GSE60185, GSE75067, and from TCGA. Using this method 91% of the breast cancer samples were detected as breast cancer (FIG. 13A) and both DCIS and invasive cancers were detected. The inventors then demonstrated the utility of the combined spec and detect DNA methylation scores for differentiating between breast cancer and other cancers using a "validation cohort" with methylation data from GSE and TCGA for breast cancer and 8 other types of cancer (FIG. 14A). A ROC curve presented in FIG. 14B reveals the specificity (0.89) and sensitivity (0.87) of this methylation score for differentiating breast cancer from other normal tissue and other cancers (FIG. 14C). These DNA methylation markers and the calculated methylation score from the methylation values could be used for early detection of breast cancer in women at risk as well as the general healthy population using different biomaterial from the patient from tissues, feces, saliva, plasma and urine.

Embodiment 11. Discovery of a Polygenic DNA Methylation Marker for Colorectal Cancer (CRC)

The inventors used normalized Illumina 450K DNA methylation data for 25 people from GSE(32146) (normal) and 50 randomly selected samples from the TCGA colorectal cancer collection of colorectal cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect colorectal cancer with high sensitivity and specificity in the training cohort (FIG. 15B, Table 9) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types. The inventors used this training cohort to discover a polygenic set of differentially methylated CGIDs between colorectal cancer and other tumors (FIG. 15C, Table 10) (spec). A weighted DNA methylation score was developed for the CGIDs as described in embodiment 2.

Embodiment 12. Utility of Colorectal Cancer Polygenic DNA Methylation Markers for Detecting Colorectal Cancer The inventors then demonstrated that the weighted colorectal cancer DNA methylation score and threshold developed in embodiment 11 (detect) detects colorectal cancer in a "validation cohort" that included normalized Illumina 450K DNA methylation beta values from GSE69550 and 459 colorectal cancer patients from TCGA. Using this method 98% of the colorectal cancer samples were detected as colorectal cancer (FIG. 16A). The inventors then demonstrated the utility of the combined spec and detect DNA methylation scores for differentiating between colorectal cancer and other cancers using a "validation cohort" with methylation data from GSE and TCGA for colorectal cancer and 8 other types of cancer (FIG. 16A). A ROC curve presented in FIG. 16B reveals the specificity (0.96) and sensitivity (0.98) of this methylation score for detecting colorectal cancer from other normal tissues and other cancers (FIG. 16C). These DNA methylation markers and the calculated methylation score from the methylation values could be used for early detection of cancer in people at risk for CRC as well as the general healthy population using different biomaterial from the patient from tissues, feces, saliva, plasma and urine.

Embodiment 13. Discovery of a Polygenic DNA Methylation Marker for Pancreatic Cancer The inventors used normalized Illumina 450K DNA methylation data for 12 people from GSE53051 (normal) and 20 randomly selected samples from the TCGA collection of pancreatic cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect pancreatic cancer with high sensitivity and specificity in the training cohort (FIG. 17B, Table 11) (detect). A weighted DNA methylation score and a threshold value for cancer was developed for the CGIDs as described in embodiment 2. The inventors then generated a "training cohort" from 100 randomly selected DNA methylation samples from TCGA representing 10 different tumor types. The inventors used this training cohort to discover a polygenic set of differentially methylated CGIDs between pancreatic cancer and other tumors (FIG. 17C, Table 12) (spec). A weighted DNA methylation score was developed for the CGIDs as described in embodiment 2.

Embodiment 14. Utility of Pancreatic Cancer Polygenic DNA Methylation Markers for Detecting Pancreatic Cancer The inventors then demonstrated that the weighted pancreatic cancer DNA methylation score and threshold developed in embodiment 13 (detect) detects pancreatic cancer in a "validation cohort" that included normalized Illumina 450K DNA methylation beta values from 891 pancreatic cancer patients from TCGA. Using this method 86% of the pancreatic cancer samples were detected as pancreatic cancer (FIG. 18A). The inventors then demonstrated the utility of the combined spec and detect DNA methylation scores for differentiating between pancreatic cancer and other cancers using a "validation cohort" with methylation data from GSE and TCGA for pancreatic cancer and 9 other types of cancer (FIG. 18A). A ROC curve presented in FIG. 18B reveals the specificity (0.93) and sensitivity (0.86) of this methylation score for detecting pancreatic cancer and differentiating it from other normal tissue and other cancers (FIG. 18C). These DNA methylation markers and the calculated methylation scores from the methylation values could be used for early detection of cancer in people at risk as well as the general healthy population using different biomaterial from the patient from tissues, feces, saliva, plasma and urine.

Embodiment 15. Discovery of a Polygenic DNA Methylation Marker for Brain Cancer The inventors used normalized Illumina 450K DNA methylation data for 10 people from GSE65820 (normal) and 10 randomly selected samples from the TCGA collection of brain cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a set of binary categorical differentially methylated CGIDs that detect brain cancer with high sensitivity and specificity in the training cohort (FIG. 19B, Table 13) (detect). A weighted DNA methylation score and a threshold value for cancer was developed for the CGIDs as described in embodiment 2. The inventors then generated a "training cohort" from 110 randomly selected DNA methylation samples from TCGA representing 11 different tumor types. The inventors used this training cohort and discovered that the detect CGID also differentiates between brain cancer and other tumors (FIG. 19C, Table 13) (detect-spec). A weighted DNA methylation score was developed for the CGIDs as described in embodiment 2.

Embodiment 16. Utility of Brain Cancer Polygenic DNA Methylation Markers for Detecting Brain Cancer The inventors then demonstrated that the weighted brain cancer DNA methylation score and threshold developed in embodiment 15 (detect) detects brain cancer in a "validation cohort" that included normalized Illumina 450K DNA methylation beta values from 689 brain cancer patients from TCGA, 40 patients from GSE58298 and 136 patients from GSE36278. Using this method 91-97% of the brain cancer samples were detected as brain cancer (FIG. 20A). The inventors then demonstrated the utility of the same CGIDs for differentiating between brain cancer and other cancers using a "validation cohort" with methylation data from GSE and TCGA for brain cancer and 9 other types of cancer (FIG. 20A). A ROC curve presented in FIG. 22B reveals the specificity (1) and sensitivity (0.97) of this methylation score for detecting brain cancer from other normal tissue and other cancers (FIG. 20C). These DNA methylation markers and the calculated methylation score from the methylation values could be used for early detection of cancer in people at risk as well as the general healthy population using different biomaterial from the patient from tissues, feces, saliva, plasma and urine.

Embodiment 17. Discovery of a Polygenic DNA Methylation Marker for Stomach Cancer The inventors used normalized Illumina 450K DNA methylation data for 18 people from GSE99553 (normal) and 10 randomly selected samples from the TCGA collection of stomach cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect stomach cancer with high sensitivity and specificity in the training cohort (FIG. 21B, Table 14) (detect). A weighted DNA methylation score and a threshold value for cancer was developed for the CGIDs as described in embodiment 2. The inventors then generated a "training cohort" from 100 randomly selected DNA methylation samples from TCGA representing 11 different tumor types. The inventors used this training cohort to discover a polygenic set of differentially methylated CGIDs between stomach cancer and other tumors (FIG. 21C, Table 15) (spec). A weighted DNA methylation score was developed for the CGIDs as described in embodiment 2.

Embodiment 18. Utility of Stomach Cancer Polygenic DNA Methylation Markers for Detecting Stomach Cancer The inventors then demonstrated that the weighted stomach cancer DNA methylation score and threshold developed in embodiment 17 (detect) detects stomach cancer in a "validation cohort" that included normalized Illumina 450K DNA methylation beta values from 397 stomach cancer patients from TCGA. Using this method, 88% of the stomach cancer samples were detected as stomach cancer (FIG. 23A). The inventors then demonstrated the utility of the combined spec and detect DNA methylation scores for differentiating between stomach cancer and other cancers using a "validation cohort" with methylation data from GSE and TCGA for stomach cancer and 10 other types of cancer (FIG. 23A). A ROC curve presented in FIG. 22B reveals the specificity (0.9 for) and sensitivity (0.9) of this methylation score for detecting stomach cancer from other normal tissues and other cancers (FIG. 22C). These DNA methylation markers and the calculated methylation score from the methylation values could be used for screening and early detection of cancer in people at risk as well as the general healthy population using different biomaterial from the patient from tissues, feces, saliva, plasma and urine.

Figure 2:
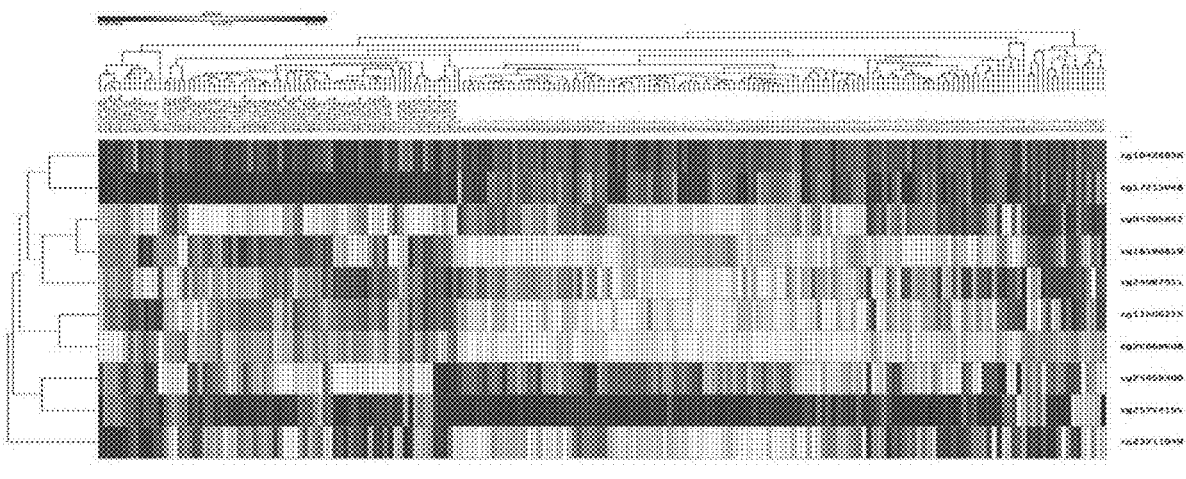
FIG. 2 is an illustration showing the Lack of Tissue specificity of current Circulating DNA markers for HCC. The illustrated heatmap shows 10 CG IDs shortlisted in Xu et al., (Xu et al., 2017) as biomarkers of HCC and methylation levels for these sites in other normal tissues. Several of the CG IDs proposed as specific biomarkers of HCC are methylated in other tissues are well and show varying levels of methylation in blood DNA. (blue 0 methylation dark red 100% methylation)
Figure 2A:
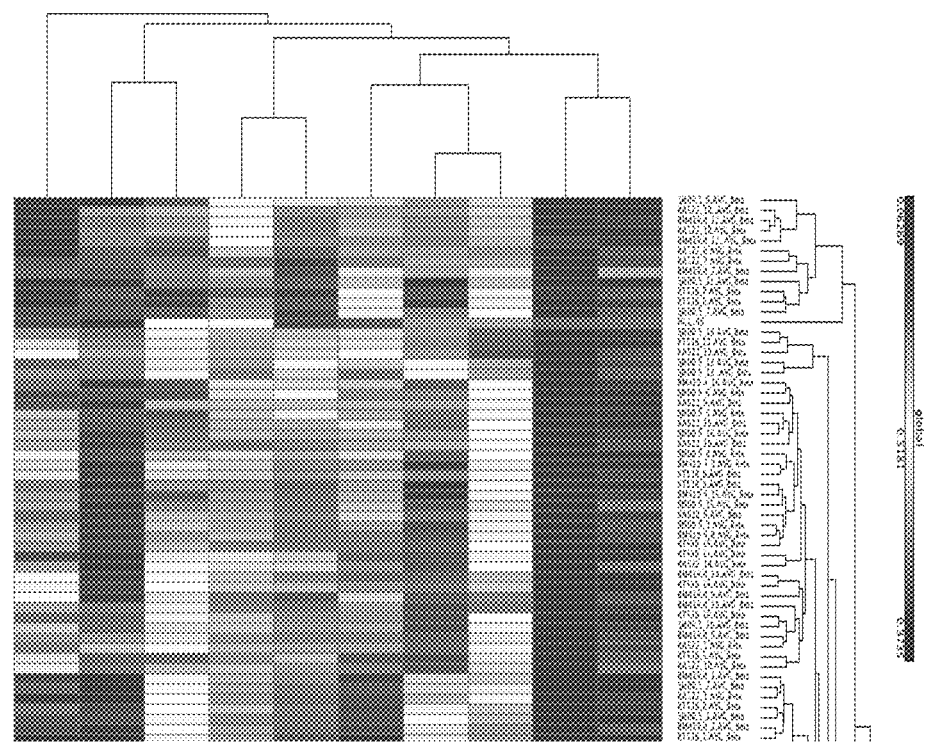
Figure 2B:
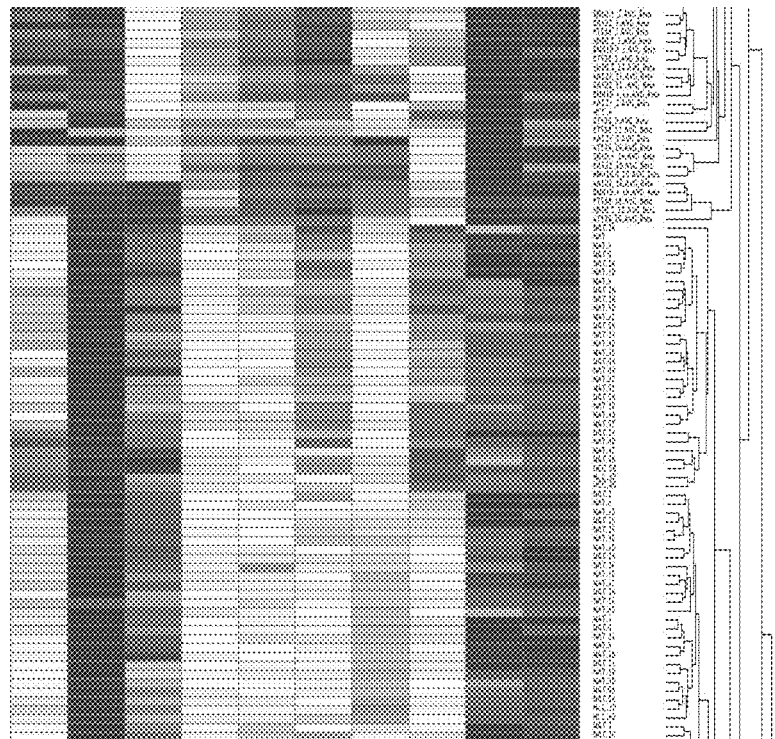
Figure 2C:
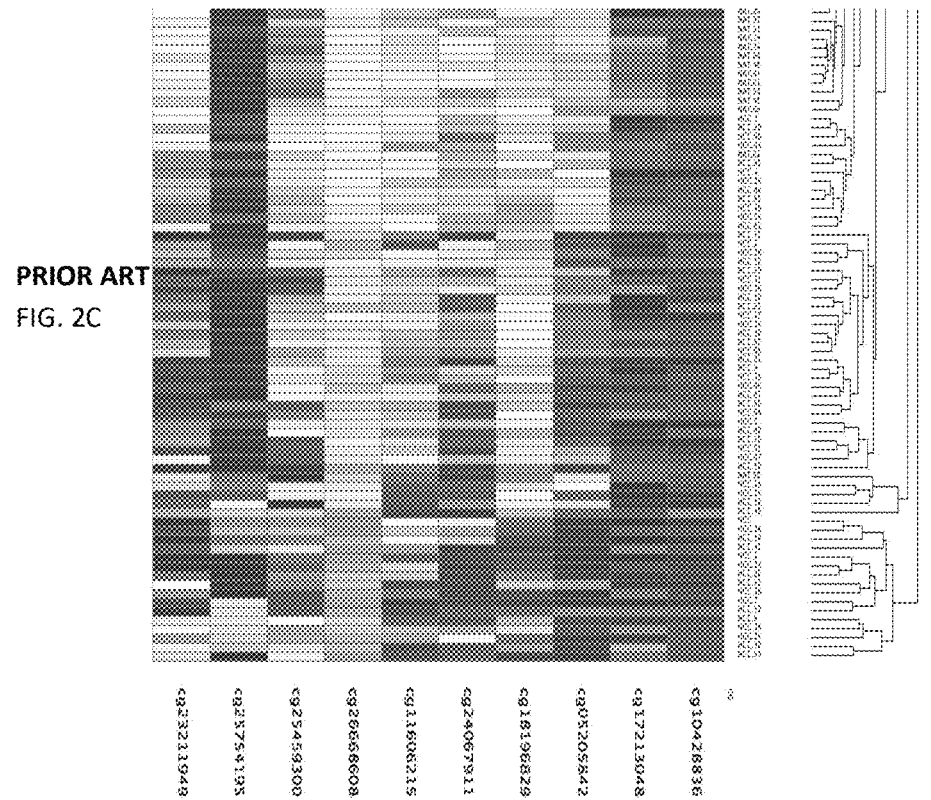
Figure 3:
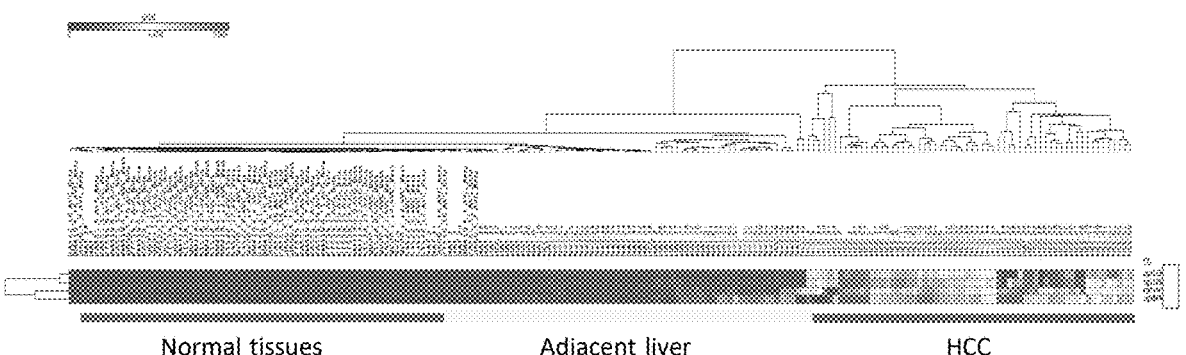
FIG. 3 is an illustration showing the specificity of HCC DNA methylation markers discovered using the BCD method for cancer DNA. The illustrated heatmap shows 4 CG IDs selected as HCC DNA methylation markers by the BCD method described herein. Methylation levels are categorically different between cancer (HCC) and normal tissues and blood, whereby the sites are unmethylated in all individuals in blood and other tissues and measurably methylated in HCC.
Figure 3A:
Figure 3A:
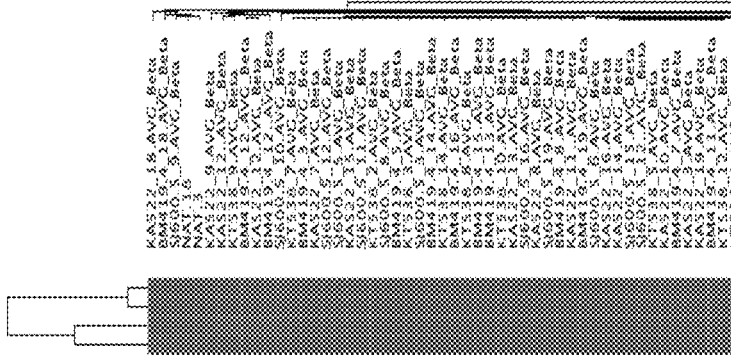
Figure 3B:
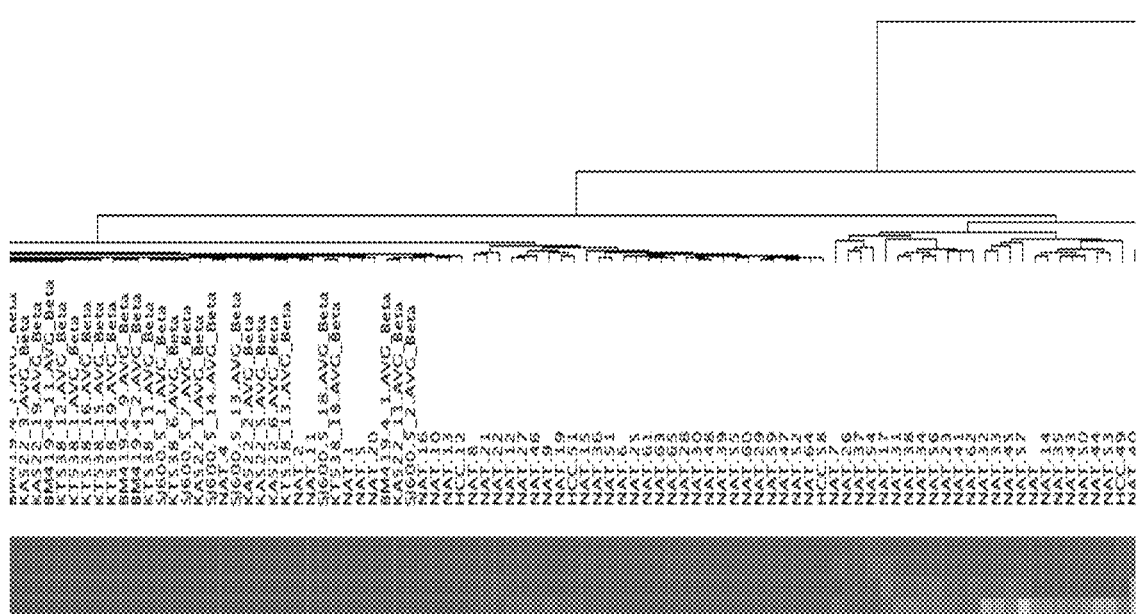
Figure 3C:
Figure 3C:
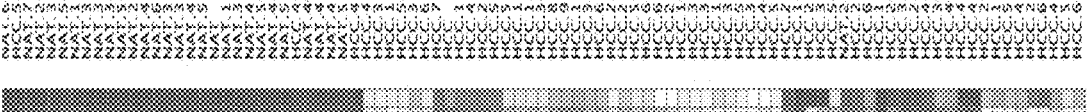
Figure 3C:
Figure 4:
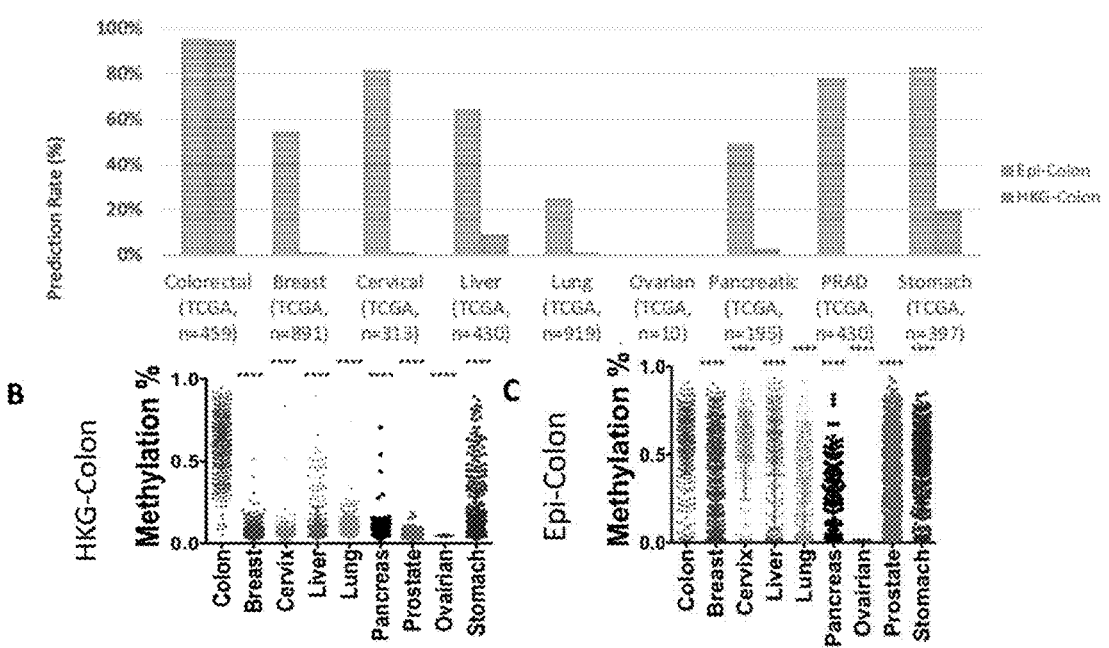
FIG. 4 is an illustration showing the lack of cancer tissue of origin specificity of current DNA methylation markers for colorectal cancer and comparison with the "detect-spec" method according to embodiments of the inventive subject matter. Illustration A shows the CG sites in Sept9 gene as included in the "Epi-colon" CF DNA methylation marker for colorectal cancer (sold by Epigenomics Inc.) which can be used to detect many other cancers utilizing methylation data from the TCGA collection of cancer DNA methylation data and thus lack specificity for colorectal cancer (HKG-Colon (HKG-epiCRC), blue). The markers disclosed in the present inventive subject matter for detection of colorectal cancer (Table 9) discovered using the BCD method (HKG-Colon orange) (Table 10) are highly specific for colorectal cancer when tested against other common solid tumors cancers. Illustrations B and C are scatter-plots of DNA methylation values for tumor DNA from different individuals with different cancers using either the HKG-Colon (HKG-epiCRC) (B) or Epi-Colon (C) DNA methylation markers. Of note are the tight and categorical differences in DNA methylation between colorectal cancer and other cancers using the HKG-epiCRC markers (B) versus the scattered heterogenous profile of Epi-Colon markers (C).
Figure 4A:
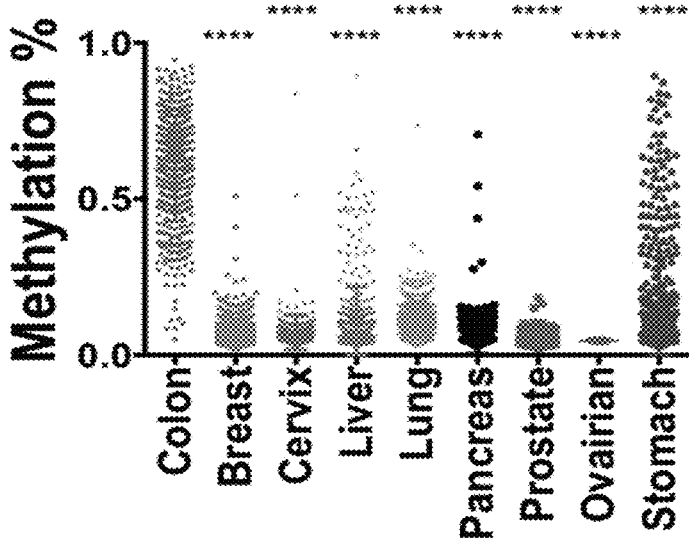
Figure 4B:
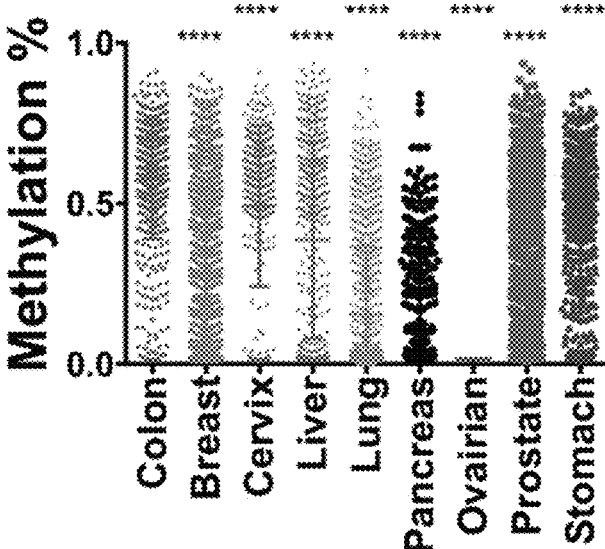

Embodiment 19. Discovery of a Polygenic DNA Methylation Marker for Ovarian Cancer The inventors used normalized Illumina 450K DNA methylation data for 5 people from GSE65820 (normal) and 10 randomly selected samples from the TCGA collection of ovarian cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect ovarian cancer with high sensitivity and specificity in the training cohort (FIG. 23B, Table 16) (detect). A weighted DNA methylation score and a threshold value for cancer was developed for the CGIDs as described in embodiment 2. The inventors then generated a "training cohort" from 100 randomly selected DNA methylation samples from TCGA representing 10 different tumor types and blood. The inventors used this training cohort to discover a polygenic set of differentially methylated CGIDs between ovarian cancer and other tumors (FIG. 2C, Table 17) (spec). A weighted DNA methylation score was developed for the CGIDs as described in embodiment 2.

Embodiment 20. Utility of Ovarian Cancer Polygenic DNA Methylation Markers for Detecting Ovarian Cancer The inventors then demonstrated that the weighted ovarian cancer DNA methylation score and threshold developed in embodiment 19 (detect) detects ovarian cancer in a "validation cohort" that included normalized Illumina 450K DNA methylation beta values from 114 ovarian cancer patients from TCGA. Using this method 86% of the ovarian cancer samples were detected as ovarian cancer (FIG. 24A). The inventors then demonstrated the utility of the spec DNA methylation scores for differentiating between ovarian cancer and other cancers using a "validation cohort" with methylation data from GSE and TCGA for ovarian cancer and 9 other types of cancer (FIG. 24A). A ROC curve presented in FIG. 24B reveals the specificity (0.99) and sensitivity (1) of this methylation score for differentiating ovarian cancer from other normal tissue and other cancers (FIG. 24C). These DNA methylation markers and the calculated methylation score from the methylation values could be used for early detection of cancer in people at risk as well as the general healthy population using different biomaterial from the patient from tissues, feces, saliva, plasma and urine.

Embodiment 21. Discovery of a Polygenic DNA Methylation Marker for Cervical Cancer The inventors used normalized Illumina 450K DNA methylation data for 20 people from GSE46306 (normal) and 10 randomly selected samples from the TCGA collection of cervix cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect cervical cancer with high sensitivity and specificity in the training cohort (FIG. 25B, Table 18) (detect). A weighted DNA methylation score and a threshold value for cancer was developed for the CGIDs as described in embodiment 2. The inventors then generated a "training cohort" from 80 randomly selected DNA methylation samples from TCGA representing 8 different tumor types and blood. The inventors used this training cohort to discover a polygenic set of differentially methylated CGIDs between cervical cancer and other tumors (FIG. 25C, Table 19) (spec). A weighted DNA methylation score was developed for the CGIDs as described in embodiment 2.

Embodiment 22. Utility of Cervical Cancer Polygenic DNA Methylation Markers for Detecting Cervical Cancer The inventors then demonstrated that the weighted cervical cancer DNA methylation score and threshold developed in embodiment 21 (detect) detects cervical cancer in a "validation cohort" that included normalized Illumina 450K DNA methylation beta values from 313 cervical cancer patients from TCGA. Using this method 91% of the cervical cancer samples were detected as cervical cancer (FIG. 26A). The inventors then demonstrated the utility of the spec DNA methylation scores for differentiating between cervical cancer and other cancers using a "validation cohort" with methylation data from GSE and TCGA for cervical cancer and 9 other types of cancer (FIG. 26A). A ROC curve presented in FIG. 26B reveals the specificity (0.9) and sensitivity (0.9) of this methylation score for detecting cervical cancer and differentiating it from other normal tissue and other cancers (FIG. 26C). These DNA methylation markers and the calculated methylation scores from the methylation values could be used for early detection of cancer in people at risk as well as the general healthy population using different biomaterial from the patient from tissues, feces, saliva, plasma and urine.

Embodiment 23. Discovery of a Polygenic DNA Methylation Marker for Head and Neck Squamous Carcinoma (HNSC)

The inventors used normalized Illumina 450K DNA methylation data for 10 people from GSE(52068) (normal) and 10 randomly selected samples from the TCGA cancer collection of HNSC DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect HNSC with high sensitivity and specificity in the training cohort (FIG. 27B, Table 20) (detect). A weighted DNA methylation score and a threshold value for cancer was developed for the CGIDs as described in embodiment 2. The inventors then generated a "training cohort" from 80 randomly selected DNA methylation samples from TCGA representing 12 different tumor types. The inventors used this training cohort to discover a polygenic set of differentially methylated CGIDs between HNSC and other tumors (FIG. 27C, Table 21) (spec).

Embodiment 24. Utility of Head and Neck Squamous Carcinoma (HNSC) Polygenic DNA Methylation Markers for Detecting HNSC The inventors then demonstrated that the weighted HNSC DNA methylation score and threshold developed in embodiment 23 (detect) detects HNSC in a "validation cohort" that included normalized Illumina 450K DNA methylation beta values from GSE52068 and. Using this method 88%-96% of the HNSC samples were detected (FIG. 28A). The inventors then demonstrated the utility of the DNA methylation detect scores for differentiating between HNSC and other cancers using a "validation cohort" with methylation data from GSE and TCGA for HNSC and 12 other types of cancer (FIG. 28A). A ROC curve presented in FIG. 28B reveals the specificity (0.86) and sensitivity (0.88) of this methylation score for differentiating HNSC from other normal tissue and other cancers (FIG. 28C). The markers also detect several other cancers (at relatively high sensitivity and is thus of limited specificity for these cancers). These DNA methylation markers and the calculated methylation score from the methylation values could be used for early detection of cancer in people at risk as well as the general healthy population using different biomaterial from the patient from tissues, feces, saliva, plasma and urine.

Embodiment 25. Discovery of a Polygenic DNA Methylation Marker for ESOPHAGEAL CANCER The inventors used normalized Illumina 450K DNA methylation data for 10 people from GSE(52068) (normal) and 10 randomly selected samples from the TCGA cancer collection of esophageal cancer DNA methylation data as a "training" cohort. The inventors first shortlisted in the "training cohort" dataset 28754 CGIDs that were discovered in embodiment 1 as sites that are robustly unmethylated across normal tissues and blood samples. The inventors then used the BCD method described in embodiment 2 to discover a polygenic set of binary categorical differentially methylated CGIDs that detect esophageal cancer with high sensitivity and specificity in the training cohort (FIG. 29B, Table 22) (detect). A weighted DNA methylation score and a threshold value for cancer was developed for the CGIDs as described in embodiment 2. The inventors then generated a "training cohort" from 80 randomly selected DNA methylation samples from TCGA representing 12 different tumor types. The inventors used this training cohort to discover a polygenic set of differentially methylated CGIDs between esophageal cancer and other tumors (FIG. 29C, Table 23) (spec).

Embodiment 26. Utility of ESOPHAGEAL CANCER Polygenic DNA Methylation Markers for Detecting ESOPHAGEAL CANCER The inventors then demonstrated that the weighted esophageal cancer DNA methylation score and threshold developed in embodiment 25 (detect) detects esophageal cancer in a "validation cohort" that included normalized Illumina 450K DNA methylation beta values from GSE52068 and. Using this method 88%-96% of the esophageal cancer samples were detected (FIG. 30A). The inventors then demonstrated the utility of the detect DNA methylation scores for differentiating between esophageal cancer and other cancers using a "validation cohort" with methylation data from GSE and TCGA for esophageal cancer and 12 other types of cancer (FIG. 30A). A ROC curve presented in FIG. 30B reveals the specificity (0.86) and sensitivity (0.88) of this methylation score for differentiating esophageal cancer from other normal tissue and other cancers (FIG. 30C). The markers also detect several other cancers (at relatively high sensitivity and are thus of limited specificity for these cancers). These DNA methylation markers and the calculated methylation score from the methylation values could be used for early detection of cancer in people at risk as well as the general healthy population using different biomaterial from the patient from tissues, feces, saliva, plasma and urine.

Embodiment 27. Discovery of a Polygenic DNA Methylation Marker for Bladder Cancer The inventors used normalized Illumina 450K DNA methylation data for 5 people from GSE52955 (normal) and 10 randomly selected samples from the TCGA collection of bladder cancer DNA methylation data as a "training" cohort. The inventors first shortlisted in the "training cohort" dataset 28754 CGIDs that were discovered in embodiment 1 as sites that robustly unmethylated across normal tissues and blood samples. The inventors then used the BCD method described in embodiment 2 to discover a polygenic set of binary categorical differentially methylated CGIDs that detects bladder cancer with high sensitivity and specificity in the training cohort (FIG. 31B, Table 24) (detect). A weighted DNA methylation score and a threshold value for cancer was developed for the CGIDs as described in embodiment 2. The inventors then generated a "training cohort" from 80 randomly selected DNA methylation samples from TCGA representing 13 different tumor types and normal blood. The inventors used this training cohort to discover a polygenic set of differentially methylated CGIDs between bladder cancer and other tumors (FIG. 31C, Table 25) (spec). A weighted DNA methylation score was developed for the CGIDs as described in embodiment 2.

Embodiment 28. Utility of Bladder Cancer Polygenic DNA Methylation Markers for Detecting Bladder Cancer The inventors then demonstrated that the weighted bladder cancer DNA methylation score and threshold developed in embodiment 27 (detect) detects bladder cancer in a "validation cohort" that included normalized Illumina 450K DNA methylation beta values from 439 bladder cancer patients from TCGA. Using this method 96% of the bladder cancer samples were detected as bladder cancer (FIG. 32B). The inventors then demonstrated the utility of the spec DNA methylation scores for differentiating between bladder cancer and other cancers using a "validation cohort" with methylation data from GSE and TCGA for bladder cancer and 13 other types of cancer (FIG. 32B). A ROC curve presented in FIG. 32C reveals the specificity (0.86) and sensitivity (0.88) of this methylation score for detecting bladder cancer from other normal tissue and other cancers (FIG. 32C). There is cross detection at reasonably high rates however of stomach, pancreatic esophageal and colorectal cancer. These DNA methylation markers and the calculated methylation scores from the methylation values could be used for early detection of cancer in people at risk as well as the general healthy population using different biomaterial from the patient from tissues, feces, saliva, plasma and urine.

Embodiment 29. Discovery of a Polygenic DNA Methylation Marker for Kidney Cancer The inventors used normalized Illumina 450K DNA methylation data for kidney (renal) cancer from 10 people from GSE52955 (normal) and 10 randomly selected samples per cancer from 13 cancers in the TCGA dataset as a "training" cohort as well as normal tissues and blood (GSE40279, GSE 52955). The inventors first shortlisted in the "training cohort" dataset 28754 CGIDs that were discovered in embodiment 1 as sites that are robustly unmethylated across normal tissues and blood samples. The inventors then used the BCD hypo method described in embodiment 2 to discover a polygenic set of binary categorical differentially methylated CGIDs that detect kidney cancer with high sensitivity and specificity in the training cohort and are specific for kidney cancer against other cancers "Detect-Spec" (FIG. 33B, Table 26) (detect-spec). A weighted DNA methylation score and a threshold value for cancer was developed for the CGIDs as described in embodiment 2.

Embodiment 30. Utility of Kidney Cancer Polygenic DNA Methylation Markers for Detecting Kidney Cancer The inventors demonstrated that the weighted kidney cancer DNA methylation score and threshold developed in embodiment 27 ("Detect-Spec") detects kidney cancer in a "validation cohort" that included normalized Illumina 450K DNA methylation beta values from 871 kidney cancer patients from TCGA and differentiate kidney cancer from other cancers. Using this method 90% of the kidney cancer samples were detected as kidney cancer (FIG. 34A). The inventors then demonstrated the utility of the "DetectSpec" DNA methylation scores for differentiating between kidney cancer and other cancers using a "validation cohort" with methylation data from GSE and TCGA for kidney cancer and 13 other types of cancer (FIG. 34A). A ROC curve presented in FIG. 34B reveals the specificity (0.87) and sensitivity (0.91) of this methylation score for detecting kidney cancer from other normal tissue and other cancers (FIG. 34C) (high crossover with HCC, brain and testis). These DNA methylation markers and the calculated methylation score from the methylation values could be used for early detection of kidney cancer in people at risk as well as the general healthy population using different biomaterial from the patient from tissues, feces, saliva, plasma and urine.

Embodiment 31. Discovery of a Polygenic DNA Methylation Marker for Testicular Cancer The inventors used normalized Illumina 450K DNA methylation data for testicular cancer from 10 people from GSE46306 (normal) and 10 randomly selected samples per cancer from 13 cancers in the TCGA dataset as a "training" cohort as well as normal tissues and blood (GSE40279, GSE 61496). The inventors first shortlisted in the "training cohort" dataset 28754 CGIDs that were discovered in embodiment 1 as sites that robustly unmethylated across normal tissues and blood samples. The inventors then used the BCD hypo method described in embodiment 2 to discover a polygenic set of binary categorical differentially methylated CGIDs that detect testicular cancer with high sensitivity and specificity in the training cohort and are specific for testicular cancer against other cancers "Detect-Spec" (FIG. 35B, Table 27) (detect-spec). A weighted DNA methylation score and a threshold value for cancer was developed for the CGIDs as described in embodiment 2.

Embodiment 32. Utility of Testicular Cancer Polygenic DNA Methylation Markers for Detecting Testis Cancer The inventors then demonstrated that the weighted testicular cancer DNA methylation score and threshold developed in embodiment 31 ("Detect-Spec") detects testicular cancer in a "validation cohort" that included normalized Illumina 450K DNA methylation beta values from 156 testicular cancer patients from TCGA and differentiate testicular cancer from other cancer. Using this method 96% of the testicular cancer samples were detected as testicular cancer (FIG. 36A). The inventors then demonstrated the utility of the "Detect-Spec" DNA methylation scores for differentiating between testicular cancer and other cancers using a "validation cohort" with methylation data from GSE and TCGA for testicular cancer and 13 other types of cancer (FIG. 36A). A ROC curve presented in FIG. 36B reveals the specificity (0.97) and sensitivity (0.96) of this methylation score for detecting testicular cancer from other normal tissue and other cancers (FIG. 36C). These DNA methylation markers and the calculated methylation score from the methylation values could be used for early detection of cancer in people at risk as well as the general healthy population using different biomaterial from the patient from tissues, feces, saliva, plasma and urine.

Embodiment 33. Discovery of a Polygenic Pan-Cancer DNA Methylation Marker for 13 Common Solid Tumors The inventors used normalized Illumina 450K DNA methylation data for 10 randomly selected samples per cancer from 13 cancers (bladder cancer, brain cancer, breast cancer, cervical cancer, colorectal cancer, esophageal cancer, HNSC, liver cancer, lung cancer, ovarian cancer, pancreatic cancer, prostate cancer, stomach cancer) in the TCGA dataset as a "training" cohort as well as normal tissues and blood from TCGA an GEO. The inventors then performed a penalized regression on the combined list of CGIDs for detection of 10 different cancer listed in tables x-y and shortlisted CGIDs that detect any of the 10 common cancers at high sensitivity and specificity (FIG. 37B, Table 28) (detect). A weighted DNA methylation score and a threshold value for cancer was developed for the CGIDs as described in embodiment 2.

Embodiment 34. Utility of Pan-Cancer Polygenic DNA Methylation Markers for Detecting Cancer The inventors then demonstrated that the weighted cancer DNA methylation score and threshold developed in embodiment 33 ("Detect") detects 13 common cancers (bladder cancer, brain cancer, breast cancer, cervical cancer, colorectal cancer, esophageal cancer, HNSC, liver cancer, lung cancer, ovarian cancer, pancreatic cancer, prostate cancer, stomach cancer) in a "validation cohort" that included normalized Illumina 450K DNA methylation beta values from 3644 cancer patients from TCGA from other normal tissues. Using this method 90-95% of cancer samples were detected (FIG. 38A). A ROC curve presented in FIG. 38B reveals the specificity (0.99) and sensitivity (0.95) of this methylation score for detecting 13 cancers from other normal tissue (FIG. 38C). These DNA methylation markers and the calculated methylation score from the methylation values could be used for early detection of cancer in people at risk as well as the general healthy population using different biomaterial from the patient from tissues, feces, saliva, plasma and urine.

Embodiment 35. Discovery of a Polygenic DNA Methylation Marker for Detection of Melanoma The inventors used normalized Illumina 450K DNA methylation data for 10 randomly selected melanoma samples and 220 samples from other cancers (bladder cancer, brain cancer, breast cancer, cervical cancer, colorectal cancer, esophageal cancer, HNSC, liver cancer, lung cancer, ovarian cancer, pancreatic cancer, prostate cancer, stomach cancer) and normal blood in the TCGA and GEO datasets as a "training" cohort. The inventors then performed a penalized regression on the combined list of CGIDs for detection of melanoma and shortlisted CGIDs that detect melanoma at high sensitivity and specificity (FIG. 39, Table 28) (detect-spec). A weighted DNA methylation score and a threshold value for melanoma was developed for the CGIDs as described in embodiment 2.

Embodiment 36. Utility of Melanoma Polygenic DNA Methylation Marker for Detecting Melanoma The inventors then demonstrated that the weighted melanoma DNA methylation score and threshold developed in embodiment 35 ("Detect-spec") detects melanoma in a "validation cohort" that included normalized Illumina 450K DNA methylation beta values from 475 melanoma patients from TCGA from other cancer and normal tissues. Using this method 98% of melanoma samples were detected (FIG. 40A). A ROC curve presented in FIG. 40B reveals the specificity (0.98) and sensitivity (0.95) of this methylation score for detecting melanoma from other normal tissue and other cancers (FIG. 40C). These DNA methylation markers and the calculated methylation score from the methylation values could be used for early detection of melanoma in people at risk as well as the general healthy population using different biomaterial from the patient from tissues, feces, saliva, plasma and urine.

Embodiment 37. Discovery of a Polygenic DNA Methylation Marker for Detection of Acute Myeloid Leukemia (AML)

The inventors used normalized Illumina 450K DNA methylation data for 10 randomly selected AML samples and 10 normal blood samples in the GEO datasets as a "training" cohort. The inventors then performed a penalized regression on the combined list of CGIDs for detection of AML and shortlisted CGIDs that detect melanoma at high sensitivity and specificity (FIG. 41, Table 27) (detect-spec). A weighted DNA methylation score and a threshold value for melanoma was developed for the CGIDs as described in embodiment 2.

Embodiment 38. Utility of Acute Myeloid Leukemia (AML) Polygenic DNA Methylation Markers for Detecting AML in Blood DNA The inventors then demonstrated that the weighted melanoma DNA methylation score and threshold developed in embodiment 37 ("Detect-spec") detects AML in a "validation cohort" that included normalized Illumina 450K DNA methylation beta values from 79 AML patients from GEO and 140 patients from TGCA and normal blood. Using this method 100% of AML samples were detected (FIG. 42A). A ROC curve presented in FIG. 42B reveals the specificity (1) and sensitivity (1) of this methylation score for detecting AML from blood (FIG. 42C). These DNA methylation markers and the calculated methylation score from the methylation values could be used for early detection of AML in people at risk as well as the general healthy population using blood DNA.

Embodiment 39. Bisulfite Conversion, Multiplex Amplification and Next Generation Sequencing and Calculation of a Methylation Score for Predicting Prostate Cancer Blood was collected in 9-ml tubes containing K3-EDTA and processed within 1 h. Fresh blood samples were centrifuged at 1000 g for 10 min at 4° C. The supernatant was carefully transferred to a Falcon tube without disturbing the cellular layer and centrifuged again for 10 min for complete removal of any residual cells and frozen at −80 C. Plasma samples are thawed, and DNA is extracted by several available methods and commercially available kits for plasma DNA extraction such as Qiagen kit for plasma DNA or EZ DNA direct extraction method. DNA is purified using commercially available methods such as on AMPure XP magnetic beads and purified DNA is treated with sodium bisulfite using for example the EZ DNA bisulfite treatment kit. A library of targeted sequences is generated by two step PCR reactions (FIG. 40). The first PCR reaction targets the specific CGIDs from table 5 and 6, note PCR1 primer has complementary sequence to second PCR2 primers (FIG. 40). The inventors used human bisulfite converted genomic DNA from HEK293 cells to amplify concurrently three sequences of DNA that contain CGIDs that detect prostate cancer from HIF3A (232 base pairs region), TPM4 (213 base pairs region), and CTTN (199 base pairs region) in a multiplexed PCR reaction using the following primers in a standard Taq polymerase reaction: For CGID cg02879662:

```
forward primer:
5'ACACTCTTTCCCTACACgACgCTCTT

CCgATCTNNNNNGGTAGGAGTTTTGGG

AATTGG3' (SEQ ID NO: 16)
``` and

```
reverse primer:
5'gTgACTggAgTTCAgACgTgTgCTCTT

CCgATCTCCACCCCTACAATCCCTAA3' (SEQ ID NO: 17)

For CGID cg16232979;
forward primer:
5'ACACTCTTTCCCTACACgACgCTCTTCC gATCTNNNNNYGGTTTYGGGTTTYGTATT3' (SEQ ID NO: 18)
```

```
and reverse primer:
5'gTgACTggAgTTCAgACgTgTgCTCTTCCg

ATCTACRCAAAAATATAAATCRACRATC3' (SEQ ID NO: 19)

For CGID: cg14041701 and
cg14498227; forward primer:
5'ACACTCTTTCCCTACACgACgCTCTTCCgA

TCTNNNNNGTTTTGYGTTTYGGATTTGGGTT3' (SEQ ID NO: 20)

and reverse primer:
5'gTgACTggAgTTCAgToACgTgTgCTCTT

CCgATCTCATAAACAACACCTTTAAATAAA

CACTAAA3'. (SEQ ID NO: 21)
```

The amplified fragments were fractionated on an agarose gel
   To barcode the samples, we use a second PCR reaction with the following primers:

```
        Forward primer:
        5'AATgATACggCgACCACCgAgATCTACACT

CTTTCCCTACACgAC3' (SEQ ID NO: 22)

Barcoding primer (reverse):
        5'CAAgCAgAAgACggCATACgAgATAGTCAT

CGgTgACTggAgTTCAgACgTg3' (SEQ ID NO: 23)
```

(bold bases are the index; 200 variations of this index are used. The second set of primers introduces the index for each patient as well as the reverse and forward sequencing primers. A multiplex PCR1 reaction for the three markers of prostate cancer HIF3A 232 bp, TPM4 213 bp, and CTTN 199 bp is shown on the right panel using varying primer concentrations as indicated in FIG. 41.

Embodiment 40: Utility of the Method of Bisulfite Conversion, Multiplex Amplification And Next Generation Sequencing and Calculation of a Methylation Score for Predicting Cancer The inventors demonstrate that embodiment 35 could be used for high throughput prediction of prostate cancer and other cancers using plasma samples from hundreds of patients at the same time. Indexed amplification of highly predictive CG IDs and a streamlined method for calculating a methylation score that is indicative of cancer could be used for early detection of prostate cancer and any other cancer.

Embodiment 41. Demonstration that the Biomarkers Selected Exhibit True BCD Properties Are Totally Hypomethylated in Plasma from Healthy People Plasma DNA was extracted from plasma prepared from 40 healthy individuals and was subjected to targeted amplification with cancer specific primers for the following cancers: liver, prostate, lung (FIG. 43) and stomach, pan cancer and CRC (FIG. 44) followed by barcoding using a second set of amplifications (PCR 2) and next generation sequencing as described in embodiments 39 and 40. All CGs exhibited very low levels of methylation in plasma from healthy people (FIGS. 43 and 44).

Embodiment 42. Bioinformatics Work-Flow for Determining DNA Methylation Levels

PCR2 products are combined quantified and purified and subjected to next generation sequencing on a Miseq Illumina sequencer. Sequence is demultiplexed using Illumina software for indexed sequencing, FASTQ files are generated for each patient. A Perl text editing script is used to count Ts and Cs in the FASTQ files per patient per CG IDS and quantify the fraction of methylated Cs in a CG ID in a patient by dividing the number of C/C+T. (see scheme in FIG. 42). The output CSV file is used for calculating the methylation score (Ms) for each patient using the equation:

$$Ms = \alpha + \Sigma_{i=1}^{n} \beta_i CG_i$$

when α=intercept β=coefficient for CG ID i, CG=methylation level per CG in the combination of CG IDs from 1 to n. n=number of CGs in combination. MS=methylation score.
Applications of the Inventive Subject Matter
   The applications of the inventive subject matter are in the field of molecular diagnostics and early prediction of cancer in general. Any person skilled in the art could use the present inventive subject matter to derive similar noninvasive biomarkers for early prediction of other cancers and other diseases that are accompanied by cell death and shedding of cell free DNA into the system such as neurological diseases, diabetes, heart disease such as cirrhosis and damage to heart tissue in cardiovascular disease. The present inventive subject matter provides a path to finding exquisite methylation markers of specific cell types and tissues using the BCD and BCDhypo method. Also disclosed are methods and biomarkers for early prediction of a wide range of cancers that could be used by anyone skilled in the art to detect cancer early and dramatically enhance survival rates and cure from cancer. The methods disclosed by the present invention could be used by anyone skilled in the art for routine yearly screening of healthy populations, to identify people who are starting to develop cancer and to treat them immediately and prevent the dire personal social and economic consequences of cancer mortality and morbidity, as well as for monitoring "high risk" people and monitoring response to therapy in patients undergoing treatment to detect recurrence or metastasis. Adoption of the present invention described here for routine health care management by health providers and health check-up facilities will have a vast impact on reducing the burden of cancer as well as health care costs.

The fact that the inventive subject matter includes a number of different dependent claims does not mean that one cannot use a combination of these claims for predicting cancer. The embodiments disclosed herein for measuring and statistically analyzing and predicting cancer should not be considered limiting. Various other modifications will be apparent to those skilled in the art to measure DNA methylation in cancer patients such as Illumina EPIC arrays, capture array sequencing, next generation sequencing, methylation specific PCR, epityper, restriction enzyme-based analyses and other methods found in the public domain. Similarly, there are numerous statistical methods in the public domain in addition to those listed here to use the inventive subject matter for prediction of cancer in patient samples.

Although the inventive subject matter has been explained in relation to its embodiments including one or more preferred embodiments, it is to be understood that many other possible modifications and variations can be made without departing from the spirit and scope of the claimed subject matter.

---

What is claimed is:

1. A method of diagnosing hepatocellular carcinoma (HCC) liver cancer, the method comprising the steps of extracting cell free (CF) DNA from a biological material of a patient, measuring DNA methylation levels of CG identifiers (IDs) in the extracted CF DNA from the following subsets using DNA pyrosequencing methylation assays or using multiplexed amplification targeted bisulfite sequencing on a next generation sequencer, calculating a cancer methylation score from said DNA methylation levels for each of detection of HCC liver cancer (detect) and differentiation from other tumors (spec), and comparing each methylation score with a corresponding methylation score threshold value for each of detection and differentiation of HCC, wherein if the methylation score for detection of HCC is above the methylation score threshold value for detection of HCC, the patient is diagnosed as having HCC and if the methylation score for differentiation of HCC is above the methylation score threshold value for differentiation of HCC, the patient is diagnosed as having a HCC tumor, wherein the subsets comprise a subset for calculating the cancer methylation score for detect comprised of cg02012576, cg03768777, cg24804544, and cg05739190 and a subset for calculating the cancer methylation score for spec comprised of cg14126493.

2. The method of claim 1, wherein the step of calculating the methylation score for each of detection and differentiation of HCC liver cancer comprises the use of a multivariate linear regression equation.

3. The method of claim 2, wherein the multivariate linear regression equation is:

$$Ms = \alpha + \Sigma_{i=1}^{n}\beta_i CG_i$$

wherein Ms is the methylation score for detection of HCC or the methylation score for differentiation of HCC, a is an intercept, $\beta$ is a coefficient for CG, CG is the methylation level per CG ID in combination and i is a number of CG IDs in combination.

4. The method of claim 1, further comprising a step of using a Receiver operating characteristics (ROC) assay to define the methylation score threshold for differentiating HCC by using measurements of DNA methylation combinations.

5. The method of claim 1, wherein the biological material is saliva, urine, plasma, feces, tissue swabs, or a combination thereof.

6. The method of diagnosing hepatocellular carcinoma (HCC) liver cancer of claim 1, wherein the measuring of DNA methylation levels further comprises measuring DNA methylation levels of CG identifiers (IDs) in the extracted CF DNA from the following tables:

| Liver_detect | | | | | |
| --- | --- | --- | --- | --- | --- |
| cg00370303 | cg10900437 | | cg16460359 | cg04035559 | cg17419241 |
| cg00931619 | cg11223367 | | cg16977570 | cg04085025 | cg18607529 |
| cg05040544 | cg19289599 | cg06233293 | | cg26523670 | cg09992116 |
| cg05739190 | cg24599205 | | | | |

| Liver_spec | | | | | |
| --- | --- | --- | --- | --- | --- |
| cg12137206 | | cg06105778 | cg22076972 | cg13341720 | cg03705926 |
| cg09363194 | cg07036412 | cg02702614 | cg10181419 | cg05876864 | cg11068343 |
| cg17167468 | cg15375239 | cg00026222 | cg17283781 | cg16147221 | cg26386472 |
| cg14570307 | cg06207432 | cg07610192 | cg03422204 | cg11684022 | cg23693289 |
| cg21107197 | cg04920951 | cg20385508 | cg25296314 | cg20707679 | cg26703661 |
| cg00456086 | cg05009389 | cg19388016 | cg08460435 | cg04739306 | cg04221886 |
| cg26797073 | cg04109768 | cg05337743 | cg00483503 | cg18668780 | cg10604002 |
| cg27650175 | cg05684891 | cg26026416 | cg00177496 | cg14221460 | cg16551483 |
| cg13438961 | cg24432073 | cg21059834 | cg23305567 | cg04809136 | cg21105227. |

\* \* \* \* \*

```
                        SEQUENCE LISTING

<160> NUMBER OF SEQ ID NOS: 31

<210> SEQ ID NO 1
<211> LENGTH: 23
<212> TYPE: DNA
<213> ORGANISM: Artificial sequence
<220> FEATURE:
<223> OTHER INFORMATION: Reverse (biotinylated) primer used with DNA
      pyrosequencing methylation assays for CGID cg02012576

<400> SEQUENCE: 1
accactaccc caacccaacc cta                                        23

<210> SEQ ID NO 2
<211> LENGTH: 16
<212> TYPE: DNA
<213> ORGANISM: Homo sapiens

<400> SEQUENCE: 2
ggttttagga tgtttg                                                16

<210> SEQ ID NO 3
<211> LENGTH: 29
<212> TYPE: DNA
<213> ORGANISM: Artificial sequence
<220> FEATURE:
<223> OTHER INFORMATION: Forward primer used with DNA pyrosequencing
      methylation assays for CG ID cg02012576

<400> SEQUENCE: 3
ggtagttagg aagtttagag gttgtagta                                  29

<210> SEQ ID NO 4
<211> LENGTH: 29
<212> TYPE: DNA
<213> ORGANISM: Artificial Sequence
<220> FEATURE:
<223> OTHER INFORMATION: Forward primer used with DNA pyrosequencing
      methylation assays for CG ID cg03768777 (VASH2)

<400> SEQUENCE: 4 agaataaat tagagaatgg gatatggaa                                   29

<210> SEQ ID NO 5
```

-continued

```
<211> LENGTH: 20
<212> TYPE: DNA
<213> ORGANISM: Artificial sequence
<220> FEATURE:
<223> OTHER INFORMATION: Reverse (biotinylated) primer used with DNA
      pyrosequencing methylation assays for CG ID cg03768777 (VASH2)

<400> SEQUENCE: 5
acaactccaa aatcctacct                                              20

<210> SEQ ID NO 6
<211> LENGTH: 18
<212> TYPE: DNA
<213> ORGANISM: Homo sapiens

<400> SEQUENCE: 6
gaatgggata tggaatga                                                18

<210> SEQ ID NO 7
<211> LENGTH: 25
<212> TYPE: DNA
<213> ORGANISM: Artificial sequence
<220> FEATURE:
<223> OTHER INFORMATION: Forward primer used with DNA pyrosequencing
      methylation assays for CG ID cg05739190 (CCNJ)

<400> SEQUENCE: 7
gtttaggagt tgggttttag ttgag                                        25

<210> SEQ ID NO 8
<211> LENGTH: 22
<212> TYPE: DNA
<213> ORGANISM: Artificial sequence
<220> FEATURE:
<223> OTHER INFORMATION: Reverse (biotinylated) primer used with DNA
      pyrosequencing methylation assays for CG ID cg05739190 (CCNJ)

<400> SEQUENCE: 8
accccaccct aactccctta cc                                           22

<210> SEQ ID NO 9
<211> LENGTH: 16
<212> TYPE: DNA
<213> ORGANISM: Homo sapiens

<400> SEQUENCE: 9
tgggttttag ttgagg                                                  16

<210> SEQ ID NO 10
<211> LENGTH: 23
<212> TYPE: DNA
<213> ORGANISM: Artificial sequence
<220> FEATURE:
<223> OTHER INFORMATION: Forward (biotinylated) primer used with DNA
      pyrosequencing methylation assays for use with cg24804544
      (GRID2IP)

<400> SEQUENCE: 10
gggtagggga gggttttgaa ata                                          23

<210> SEQ ID NO 11
<211> LENGTH: 23
<212> TYPE: DNA
<213> ORGANISM: Artificial sequence
<220> FEATURE:
<223> OTHER INFORMATION: Reverse primer used with DNA pyrosequencing
      methylation assays for use with cg24804544 (GRID2IP)
```

-continued

<400> SEQUENCE: 11 taacccccc tccaacctca ttc                                          23

<210> SEQ ID NO 12
<211> LENGTH: 16
<212> TYPE: DNA
<213> ORGANISM: Homo sapiens

<400> SEQUENCE: 12
cacccaactt ctcaat                                                 16

<210> SEQ ID NO 13
<211> LENGTH: 29
<212> TYPE: DNA
<213> ORGANISM: Artificial sequence
<220> FEATURE:
<223> OTHER INFORMATION: Forward (biotinylated) primer used with DNA
      pyrosequencing methylation assays for use with CGID cg02012576
      (HPX)

<400> SEQUENCE: 13
atttttatgg gtattagttt tagggagaa                                   29

<210> SEQ ID NO 14
<211> LENGTH: 30
<212> TYPE: DNA
<213> ORGANISM: Artificial sequence
<220> FEATURE:
<223> OTHER INFORMATION: Reverse (biotinylated) primer used with DNA
      pyrosequencing methylation assays for use with CGID cg02012576
      (HPX)

<400> SEQUENCE: 14
ccaaaactat cctataacct ctacaactca                                  30

<210> SEQ ID NO 15
<211> LENGTH: 15
<212> TYPE: DNA
<213> ORGANISM: Homo sapiens

<400> SEQUENCE: 15
accattacca cccct                                                  15

<210> SEQ ID NO 16
<211> LENGTH: 59
<212> TYPE: DNA
<213> ORGANISM: Artificial sequence
<220> FEATURE:
<223> OTHER INFORMATION: Forward primer used with polygenic multiplexed
      amplicon bisulfite sequencing DNA methylation assays for use with
      CGID cg02879662 in 5' to 3' direction
<220> FEATURE:
<221> NAME/KEY: misc_feature
<222> LOCATION: (34)..(38)
<223> OTHER INFORMATION: n is a, c, g, or t

<400> SEQUENCE: 16
acactctttc cctacacgac gctcttccga tctnnnnngg taggagtttt gggaattgg    59

<210> SEQ ID NO 17
<211> LENGTH: 53
<212> TYPE: DNA
<213> ORGANISM: Artificial sequence
<220> FEATURE:
<223> OTHER INFORMATION: Reverse primer used with polygenic multiplexed
      amplicon bisulfite sequencing DNA methylation assays for use with CGID cg02879662 in 5' to 3' direction

<400> SEQUENCE: 17
gtgactggag ttcagacgtg tgctcttccg atctccaccc ctacaatccc taa          53

<210> SEQ ID NO 18
<211> LENGTH: 57
<212> TYPE: DNA
<213> ORGANISM: Artificial sequence
<220> FEATURE:
<223> OTHER INFORMATION: Forward primer used with polygenic multiplexed
      amplicon bisulfite sequencing DNA methylation assays for use with
      CGID cg16232979 in 5' to 3' direction
<220> FEATURE:
<221> NAME/KEY: misc_feature
<222> LOCATION: (34)..(38)
<223> OTHER INFORMATION: n is a, c, g, or t

<400> SEQUENCE: 18
acactctttc cctacacgac gctcttccga tctnnnnnyg gtttygggtt tygtatt       57

<210> SEQ ID NO 19
<211> LENGTH: 58
<212> TYPE: DNA
<213> ORGANISM: Artificial sequence
<220> FEATURE:
<223> OTHER INFORMATION: Reverse primer used with polygenic multiplexed
      amplicon bisulfite sequencing DNA methylation assays for use with
      CGID cg16232979 in 5' to 3' direction

<400> SEQUENCE: 19
gtgactggag ttcagacgtg tgctcttccg atctacrcaa aaatataaat cracratc      58

<210> SEQ ID NO 20
<211> LENGTH: 61
<212> TYPE: DNA
<213> ORGANISM: Artificial sequence
<220> FEATURE:
<223> OTHER INFORMATION: Forward primer used with polygenic multiplexed
      amplicon bisulfite sequencing DNA methylation assays for use with
      CG IDs cg14041701 and cg14498227 in 5' to 3' direction
<220> FEATURE:
<221> NAME/KEY: misc_feature
<222> LOCATION: (34)..(38)
<223> OTHER INFORMATION: n is a, c, g, or t

<400> SEQUENCE: 20
acactctttc cctacacgac gctcttccga tctnnnnngt tttgygttty ggatttgggt    60
t                                                                    61

<210> SEQ ID NO 21
<211> LENGTH: 64
<212> TYPE: DNA
<213> ORGANISM: Artificial sequence
<220> FEATURE:
<223> OTHER INFORMATION: Reverse primer used with polygenic multiplexed
      amplicon bisulfite sequencing DNA methylation assays for use with
      CG IDs cg14041701 and cg14498227 in 5' to 3' direction

<400> SEQUENCE: 21
gtgactggag ttcagacgtg tgctcttccg atctcataaa caacacctttt aaataaacac   60 taaa                                                                 64

<210> SEQ ID NO 22
<211> LENGTH: 45
<212> TYPE: DNA
<213> ORGANISM: Artificial sequence -continued

```
<220> FEATURE:
<223> OTHER INFORMATION: Forward primer used with polygenic multiplexed
      amplicon bisulfite sequencing DNA methylation assays for use with
      barcoding CG IDs cg14041701 and cg14498227 listed in 5' to 3'
      direction

<400> SEQUENCE: 22
aatgatacgg cgaccaccga gatctacact ctttccctac acgac                          45

<210> SEQ ID NO 23
<211> LENGTH: 52
<212> TYPE: DNA
<213> ORGANISM: Artificial sequence
<220> FEATURE:
<223> OTHER INFORMATION: Reverse primer used with polygenic multiplexed
      amplicon bisulfite sequencing DNA methylation assays for use with
      barcoding CG IDs cg14041701 and cg14498227 listed in 5' to 3'
      direction

<400> SEQUENCE: 23
caagcagaag acggcatacg agatagtcat cggtgactgg agttcagacg tg                  52

<210> SEQ ID NO 24
<211> LENGTH: 59
<212> TYPE: DNA
<213> ORGANISM: Artificial sequence
<220> FEATURE:
<223> OTHER INFORMATION: Forward primer used with bisulfite conversion,
      multiplex amplification and next generation sequencing and
      calculation of a methylation score for predicting prostate cancer
      for use with CGID cg02879662 listed in 5' to 3' direction
<220> FEATURE:
<221> NAME/KEY: misc_feature
<222> LOCATION: (34)..(38)
<223> OTHER INFORMATION: n is a, c, g, or t

<400> SEQUENCE: 24
acactctttc cctacacgac gctcttccga tctnnnnngg taggagtttt gggaattgg           59

<210> SEQ ID NO 25
<211> LENGTH: 53
<212> TYPE: DNA
<213> ORGANISM: Artificial sequence
<220> FEATURE:
<223> OTHER INFORMATION: Reverse primer used with bisulfite conversion,
      multiplex amplification and next generation sequencing and
      calculation of a methylation score for predicting prostate cancer
      for use with CGID cg02879662 listed in 5' to 3' direction

<400> SEQUENCE: 25
gtgactggag ttcagacgtg tgctcttccg atctccaccc ctacaatccc taa                 53

<210> SEQ ID NO 26
<211> LENGTH: 57
<212> TYPE: DNA
<213> ORGANISM: Artificial sequence
<220> FEATURE:
<223> OTHER INFORMATION: Forward primer used with bisulfite conversion,
      multiplex amplification and next generation sequencing and
      calculation of a methylation score for predicting prostate cancer
      for use with CGID cg16232979 listed in 5' to 3' direction
<220> FEATURE:
<221> NAME/KEY: misc_feature
<222> LOCATION: (34)..(38)
<223> OTHER INFORMATION: n is a, c, g, or t

<400> SEQUENCE: 26
acactctttc cctacacgac gctcttccga tctnnnnnyg gtttygggtt tygtatt            57
```

-continued

```
<210> SEQ ID NO 27
<211> LENGTH: 58
<212> TYPE: DNA
<213> ORGANISM: Artificial sequence
<220> FEATURE:
<223> OTHER INFORMATION: Reverse primer used with bisulfite conversion,
      multiplex amplification and next generation sequencing and
      calculation of a methylation score for predicting prostate cancer
      for use with CGID cg16232979 listed in 5' to 3' direction

<400> SEQUENCE: 27
gtgactggag ttcagacgtg tgctcttccg atctacrcaa aaatataaat cracratc        58

<210> SEQ ID NO 28
<211> LENGTH: 61
<212> TYPE: DNA
<213> ORGANISM: Artificial sequence
<220> FEATURE:
<223> OTHER INFORMATION: Forward primer used with bisulfite conversion,
      multiplex amplification and next generation sequencing and
      calculation of a methylation score for predicting prostate cancer
      for use with CGIDs cg14041701 and cg14498227 listed in 5' to 3'
      direction
<220> FEATURE:
<221> NAME/KEY: misc_feature
<222> LOCATION: (34)..(38)
<223> OTHER INFORMATION: n is a, c, g, or t

<400> SEQUENCE: 28
acactctttc cctacacgac gctcttccga tctnnnnngt tttgygtttty ggatttgggt      60 t                                                                       61

<210> SEQ ID NO 29
<211> LENGTH: 64
<212> TYPE: DNA
<213> ORGANISM: Artificial Sequence
<220> FEATURE:
<223> OTHER INFORMATION: Reverse primer used with bisulfite conversion,
      multiplex amplification and next generation sequencing and
      calculation of a methylation score for predicting prostate cancer
      for use with CGIDs cg14041701 and cg14498227 listed in 5' to 3'
      direction

<400> SEQUENCE: 29
gtgactggag ttcagacgtg tgctcttccg atctcataaa caacacctttt aaataaacac      60 taaa                                                                    64

<210> SEQ ID NO 30
<211> LENGTH: 45
<212> TYPE: DNA
<213> ORGANISM: Artificial Sequence
<220> FEATURE:
<223> OTHER INFORMATION: Barcoding forward primer used with second PCT
      reaction to barcode the samples for use with CGIDs cg14041701 and
      cg14498227 listed in 5' to 3' direction

<400> SEQUENCE: 30
aatgatacgg cgaccaccga gatctacact ctttccctac acgac                       45

<210> SEQ ID NO 31
<211> LENGTH: 52
<212> TYPE: DNA
<213> ORGANISM: Artificial Sequence
<220> FEATURE:
<223> OTHER INFORMATION: Barcoding reverse primer used with second PCT
      reaction to barcode the samples for use with CGIDs cg14041701 and
      cg14498227 listed in 5' to 3' direction
```

-continued

```
<400> SEQUENCE: 31
caagcagaag acggcatacg agatagtcat cggtgactgg agttcagacg tg                    52
```